US012698333B2

(12) United States Patent
Quintarelli et al.

(10) Patent No.: US 12,698,333 B2
(45) Date of Patent: Aug. 4, 2026

(54) CAR-CD123 VECTOR AND USES THEREOF

(71) Applicant: OSPEDALE PEDIATRICO BAMBINO GESU', Rome (IT)

(72) Inventors: Concetta Quintarelli, Rome (IT); Biagio De Angelis, Rome (IT); Franco Locatelli, Rome (IT)

(73) Assignee: OSPEDALE PEDIATRICO BAMBINO GESU', Rome (IT)

( * ) Notice: Subject to any disclaimer, the term of this patent is extended or adjusted under 35 U.S.C. 154(b) by 1162 days.

(21) Appl. No.: 17/629,681

(22) PCT Filed: Jul. 24, 2020

(86) PCT No.: PCT/EP2020/071053
§ 371 (c)(1),
(2) Date: Jan. 24, 2022

(87) PCT Pub. No.: WO2021/014022
PCT Pub. Date: Jan. 28, 2021

(65) Prior Publication Data
US 2022/0251224 A1 Aug. 11, 2022

(30) Foreign Application Priority Data

Jul. 25, 2019 (EP) .................................... 19188360

(51) Int. Cl.
| | |
|---|---|
| C07K 16/28 | (2006.01) |
| A61K 39/00 | (2006.01) |
| A61K 40/11 | (2025.01) |
| A61K 40/15 | (2025.01) |
| A61K 40/31 | (2025.01) |
| A61K 40/42 | (2025.01) |
| A61P 35/02 | (2006.01) |
| C07K 14/705 | (2006.01) |
| C07K 19/00 | (2006.01) |
| C12N 5/0783 | (2010.01) |
| C12N 15/00 | (2006.01) |

(52) U.S. Cl.
CPC .......... *C07K 16/2866* (2013.01); *A61K 40/11* (2025.01); *A61K 40/15* (2025.01); *A61K 40/31* (2025.01); *A61K 40/4211* (2025.01); *A61K 40/4217* (2025.01); *A61P 35/02* (2018.01); *C07K 14/7051* (2013.01); *C12N 5/0636* (2013.01); *C12N 5/0646* (2013.01); *A61K 2239/29* (2023.05); *A61K 2239/31* (2023.05); *A61K 2239/38* (2023.05); *A61K 2239/48* (2023.05)

(58) Field of Classification Search
None
See application file for complete search history.

(56) References Cited

U.S. PATENT DOCUMENTS

| | | | | |
|---|---|---|---|---|
| 2015/0093401 A1* | 4/2015 | Pule | ........................ | A61P 35/00 435/375 |
| 2016/0046718 A1* | 2/2016 | Wilson | .................... | A61P 35/00 424/139.1 |
| 2016/0058857 A1* | 3/2016 | Spencer | ............... | C12N 9/6472 435/325 |
| 2016/0152723 A1* | 6/2016 | Chen | .................. | C07K 16/2896 435/254.2 |
| 2017/0260277 A1* | 9/2017 | Forman | .............. | C07K 14/7051 |
| 2019/0106492 A1* | 4/2019 | Schneider | ............ | C12N 5/0636 |

FOREIGN PATENT DOCUMENTS

| | | | | |
|---|---|---|---|---|
| EP | 3293199 A1 | 3/2018 | | |
| WO | 2011/056894 A2 | 5/2011 | | |
| WO | WO-2011146862 A1 * | 11/2011 | .............. | A61P 35/00 |
| WO | 2014/144622 A2 | 9/2014 | | |
| WO | 2014/197638 A2 | 12/2014 | | |
| WO | 2016/044811 A1 | 3/2016 | | |
| WO | 2016/201065 A1 | 12/2016 | | |
| WO | 2016/201394 A1 | 12/2016 | | |
| WO | 2017/075147 A1 | 5/2017 | | |
| WO | 2019/113509 A2 | 6/2019 | | |

OTHER PUBLICATIONS

Al Qaraghuli et al. Antibody-protein binding and conformational changes: identifying allosteric signalling pathways to engineer a better effector response. Nature Scientific Reports 10:13969 (2020). (Year: 2020).*

Fenton et al. Rheostat positions: A new classification of protein positions relevant to pharmacogenomics. Medicinal Chemistry Research 29:1133-1146 (2020). (Year: 2020).*

Bhattacharya et al. Impact of genetic variation on three dimensional structure and function of proteins. PLoS One 12(3): e0171355; (2017). (Year: 2017).*

Rabia et al. Understanding and overcoming trade-offs between antibody affinity, specificity, stability and solubility. Biochemical Engineering Journal 137:365-374; (2018). (Year: 2018).*

JPO, Notice of Reasons for Refusal, mailed Jul. 22, 2024, in connection with related Japanese patent application No. 2022-505250, with English translation, 13 pages.

Budde Le et al., "Truncated Cell-Surface CD19 as a Conditional Suicide Switch for Adoptive T Cell Immunotherapy", Blood, 2013, vol. 122, p. 1660.

(Continued)

*Primary Examiner* — Bridget E Bunner
*Assistant Examiner* — Regina M DeBerry
(74) *Attorney, Agent, or Firm* — Lucas & Mercanti, LLP

(57) ABSTRACT

The present invention relates to a chimeric antigen receptor (CAR) molecule containing, from the N-terminus to the C-terminus: a) an extracellular domain and transmembrane domain of human CD19, b) an antigen binding domain, c) a spacer domain, d) a transmembrane domain, and e) a cytoplasmatic domain, preferably wherein the CAR is a CD123 specific CAR (CD123 CAR) and the antigen binding domain includes a VL and/or VH from a monoclonal anti-CD123 antibody, more preferably the antigen binding domain includes a single chain variable fragment (scFv) that specifically binds to CD123.

7 Claims, 17 Drawing Sheets

Figure 1:
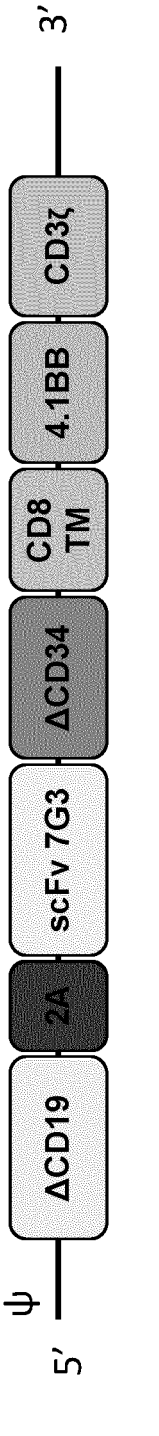

Specification includes a Sequence Listing.

(56) References Cited

OTHER PUBLICATIONS

Lihua Elizabeth Budde et al, "Truncated Cell-Surface CD19 as a Conditional Suicide Switch for Adoptive T Cell Immunotherapy", Nov. 15, 2013 (Nov. 15, 2013), p. 1660, (6 pages), Retrieved from the Internet: URL:https://ashpublications.org/blood/article/122/21/1660/12377/Truncated-Cell-Surface-CD19-As-a-Conditional, XP055739781 [retrieved on Oct. 14, 2020].

A. Mardiros et al, "T cells expressing CD123-specific chimeric antigen receptors exhibit specific cytolytic effector functions and antitumor effects against human acute myeloid leukemia", Blood, vol. 122, No. 18, Oct. 31, 2013 (Oct. 31, 2013), pp. 3138-3148, XP055607043.

X. Wang et al, "A transgene-encoded cell surface polypeptide for selection, in vivo tracking, and ablation of engineered cells", Blood, vol. 118, No. 5, Aug. 4, 2011 (Aug. 4, 2011), p. 1255-1263, XP055062819.

Paulina J. Paszkiewicz et al, "Targeted antibody-mediated depletion of murine CD19 Car T cells permanently reverses B cell aplasia", Journal of Clinical Investigation, vol. 126, No. 11, Nov. 1, 2016 (Nov. 1, 2016), p. 4262-4272, XP055510326.

Tey et al, "Inducible Caspase 9 Suicide Gene to Improve the Safety of Allodepleted T Cells after Haploidentical Stem Cell Transplantation", Biology of Blood and Marrow Transplantation, Kluge Carden Jennings Publishing, Charlottesville, VA, US, vol. 13, No. 8, Jul. 18, 2007 (Jul. 18, 2007), p. 913-924, XP022157037.

Lihua E. Budde et al, "Combining a CD20 Chimeric Antigen Receptor and an Inducible Caspase 9 Suicide Switch to Improve the Efficacy and Safety of T Cell Adoptive Immunotherapy for Lymphoma", Plos One, vol. 8, No. 12, Dec. 17, 2013 (Dec. 17, 2013), p. 1-10, XP055213511.

Ohad Hammer, "CD19 as an attractive target for antibody-based therapy", MABS, vol. 4, No. 5, Sep. 1, 2012 (Sep. 1, 2012), p. 571-577, XP055320679.

Xiuqi Wu et al, "A Fusion Receptor as a Safety Switch, Detection, and Purification Biomarker for Adoptive Transferred T Cells", Molecular Therapy, vol. 25, No. 10, Oct. 1, 2017 (Oct. 1, 2017), p. 2270-2279, KP055661114.

Tiziano Ingegnere et al, "Human CAR NK Cells: A New Non-viral Method Allowing High Efficient Transfection and Strong Tumor Cell Killing", Frontiers in Immunology, vol. 10, Apr. 30, 2019 (Apr. 30, 2019), p. 957, (10 pages), XP055740362.

ISA/EP, "PCT International Search Report and Written Opinion", which was issued in connection with PCT Application No. PCT/EP2020/071053, and mailed Oct. 27, 2020 (20 pages).

Gill, Saar et al. "Preclinical targeting of human acute myeloid leukemia and myeloablation using chimeric antigen receptor-modified T cells." Blood vol. 123(15) (2014): 2343-54.

* cited by examiner

```
SEQUENCE LISTING

<160> NUMBER OF SEQ ID NOS: 51

<210> SEQ ID NO 1
<211> LENGTH: 333
<212> TYPE: PRT
<213> ORGANISM: Homo sapiens

<400> SEQUENCE: 1

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30
```

-continued

```
Asn Ala Val Leu Gln Cys Leu Lys Gly Thr Ser Asp Gly Pro Thr Gln
    35              40                  45

Gln Leu Thr Trp Ser Arg Glu Ser Pro Leu Lys Pro Phe Leu Lys Leu
    50              55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
            165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
    195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
            245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
            325                 330

<210> SEQ ID NO 2
<211> LENGTH: 20
<212> TYPE: PRT
<213> ORGANISM: Artificial Sequence
<220> FEATURE:
<223> OTHER INFORMATION: 2A peptide

<400> SEQUENCE: 2

Arg Gly Arg Gly Arg Gly Ser Leu Leu Thr Cys Gly Asp Val Glu Glu
1               5                   10                  15

Asn Pro Gly Pro
            20

<210> SEQ ID NO 3
<211> LENGTH: 21
<212> TYPE: PRT
<213> ORGANISM: Artificial Sequence
<220> FEATURE:
```

<223> OTHER INFORMATION: signal

<400> SEQUENCE: 3

Met Glu Phe Gly Leu Ser Trp Leu Phe Leu Val Ala Ile Leu Lys Gly
1               5                   10                  15

Val Gln Cys Ser Arg
            20

<210> SEQ ID NO 4
<211> LENGTH: 114
<212> TYPE: PRT
<213> ORGANISM: Artificial Sequence
<220> FEATURE:
<223> OTHER INFORMATION: 7G3 VL

<400> SEQUENCE: 4

Asp Phe Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys Arg

<210> SEQ ID NO 5
<211> LENGTH: 118
<212> TYPE: PRT
<213> ORGANISM: Artificial Sequence
<220> FEATURE:
<223> OTHER INFORMATION: 7G3 VH

<400> SEQUENCE: 5

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ser Ser Thr Ala Tyr
65                  70                  75                  80

Met His Leu Asn Ser Leu Thr Ser Glu Asp Ser Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val
        115

<210> SEQ ID NO 6

```
<211> LENGTH: 16
<212> TYPE: PRT
<213> ORGANISM: Artificial Sequence
<220> FEATURE:
<223> OTHER INFORMATION: trackable marker

<400> SEQUENCE: 6

Glu Leu Pro Thr Gln Gly Thr Phe Ser Asn Val Ser Thr Asn Val Ser
1               5                   10                  15

<210> SEQ ID NO 7
<211> LENGTH: 42
<212> TYPE: PRT
<213> ORGANISM: Artificial Sequence
<220> FEATURE:
<223> OTHER INFORMATION: spacer

<400> SEQUENCE: 7

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40

<210> SEQ ID NO 8
<211> LENGTH: 21
<212> TYPE: PRT
<213> ORGANISM: Homo sapiens

<400> SEQUENCE: 8

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 9
<211> LENGTH: 16
<212> TYPE: PRT
<213> ORGANISM: Homo sapiens

<400> SEQUENCE: 9

Leu Tyr Cys Asn His Arg Asn Arg Arg Arg Val Cys Lys Cys Pro Arg
1               5                   10                  15

<210> SEQ ID NO 10
<211> LENGTH: 42
<212> TYPE: PRT
<213> ORGANISM: Homo sapiens

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 11
<211> LENGTH: 112
<212> TYPE: PRT
<213> ORGANISM: Homo sapiens

<400> SEQUENCE: 11
```

-continued

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 12
<211> LENGTH: 869
<212> TYPE: PRT
<213> ORGANISM: Artificial Sequence
<220> FEATURE:
<223> OTHER INFORMATION: deltaCD19-2A-CAR.CD123-4.1BB-zeta CAR

<400> SEQUENCE: 12

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255
```

-continued

```
Gly Lys Tyr Tyr Cys His Arg Gly Asn Leu Thr Met Ser Phe His Leu
        260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Arg Gly Arg
                325                 330                 335

Gly Arg Gly Ser Leu Leu Thr Cys Gly Asp Val Glu Glu Asn Pro Gly
            340                 345                 350

Pro Met Glu Phe Gly Leu Ser Trp Leu Phe Leu Val Ala Ile Leu Lys
        355                 360                 365

Gly Val Gln Cys Ser Arg Asp Phe Val Met Thr Gln Ser Pro Ser Ser
        370                 375                 380

Leu Thr Val Thr Ala Gly Glu Lys Val Thr Met Ser Cys Lys Ser Ser
385                 390                 395                 400

Gln Ser Leu Leu Asn Ser Gly Asn Gln Lys Asn Tyr Leu Thr Trp Tyr
                405                 410                 415

Leu Gln Lys Pro Gly Gln Pro Pro Lys Leu Leu Ile Tyr Trp Ala Ser
            420                 425                 430

Thr Arg Glu Ser Gly Val Pro Asp Arg Phe Thr Gly Ser Gly Ser Gly
        435                 440                 445

Thr Asp Phe Thr Leu Thr Ile Ser Ser Val Gln Ala Glu Asp Leu Ala
        450                 455                 460

Val Tyr Tyr Cys Gln Asn Asp Tyr Ser Tyr Pro Tyr Thr Phe Gly Gly
465                 470                 475                 480

Gly Thr Lys Leu Glu Ile Lys Arg Gly Gly Gly Ser Gly Gly Gly Gly
            485                 490                 495

Glu Val Gln Leu Gln Gln Ser Gly Pro Glu Leu Val Lys Pro Gly Ala
            500                 505                 510

Ser Val Lys Met Ser Cys Lys Ala Ser Gly Tyr Thr Phe Thr Asp Tyr
            515                 520                 525

Tyr Met Lys Trp Val Lys Gln Ser His Gly Lys Ser Leu Glu Trp Ile
        530                 535                 540

Gly Asp Ile Ile Pro Ser Asn Gly Ala Thr Phe Tyr Asn Gln Lys Phe
545                 550                 555                 560

Lys Gly Lys Ala Thr Leu Thr Val Asp Arg Ser Ser Ser Thr Ala Tyr
                565                 570                 575

Met His Leu Asn Ser Leu Thr Ser Glu Asp Ser Ala Val Tyr Tyr Cys
            580                 585                 590

Thr Arg Ser His Leu Leu Arg Ala Ser Trp Phe Ala Tyr Trp Gly Gln
        595                 600                 605

Gly Thr Leu Val Thr Val Ser Ala Gly Ser Glu Leu Pro Thr Gln Gly
        610                 615                 620

Thr Phe Ser Asn Val Ser Thr Asn Val Ser Pro Ala Pro Arg Pro Pro
625                 630                 635                 640

Thr Pro Ala Pro Thr Ile Ala Ser Gln Pro Leu Ser Leu Arg Pro Glu
                645                 650                 655

Ala Cys Arg Pro Ala Ala Gly Gly Ala Val His Thr Arg Gly Leu Asp
            660                 665                 670
```

-continued

```
Phe Ala Cys Asp Ile Tyr Ile Trp Ala Pro Leu Ala Gly Thr Cys Gly
        675             680             685

Val Leu Leu Leu Ser Leu Val Ile Thr Leu Tyr Cys Asn His Arg Asn
        690             695             700

Arg Arg Arg Val Cys Lys Cys Pro Arg Val Asp Lys Arg Gly Arg Lys
705             710             715             720

Lys Leu Leu Tyr Ile Phe Lys Gln Pro Phe Met Arg Pro Val Gln Thr
            725             730             735

Thr Gln Glu Glu Asp Gly Cys Ser Cys Arg Phe Pro Glu Glu Glu Glu
            740             745             750

Gly Gly Cys Glu Leu Arg Val Lys Phe Ser Arg Ser Ala Asp Ala Pro
            755             760             765

Ala Tyr Gln Gln Gly Gln Asn Gln Leu Tyr Asn Glu Leu Asn Leu Gly
        770             775             780

Arg Arg Glu Glu Tyr Asp Val Leu Asp Lys Arg Arg Gly Arg Asp Pro
785             790             795             800

Glu Met Gly Gly Lys Pro Arg Arg Lys Asn Pro Gln Glu Gly Leu Tyr
            805             810             815

Asn Glu Leu Gln Lys Asp Lys Met Ala Glu Ala Tyr Ser Glu Ile Gly
            820             825             830

Met Lys Gly Glu Arg Arg Arg Gly Lys Gly His Asp Gly Leu Tyr Gln
            835             840             845

Gly Leu Ser Thr Ala Thr Lys Asp Thr Tyr Asp Ala Leu His Met Gln
        850             855             860

Ala Leu Pro Pro Arg
865
```

```
<210> SEQ ID NO 13
<211> LENGTH: 999
<212> TYPE: DNA
<213> ORGANISM: Homo sapiens

<400> SEQUENCE: 13
atgccaccac ctcgcctgct gttctttctg ctgttcctga cacctatgga ggtgcgacct      60
gaggaaccac tggtcgtgaa ggtcgaggaa ggcgacaatg ccgtgctgca gtgcctgaaa     120
ggcacttctg atgggccaac tcagcagctg acctggtcca gggagtctcc cctgaagcct     180
tttctgaaac tgagcctggg actgccagga ctggaatcc acatgcgccc tctggctatc      240
tggctgttca tcttcaacgt gagccagcag atgggaggat ctacctgtg ccagccagga      300 ccaccatccg agaaggcctg gcagcctgga tggaccgtca cgtggaggg gtctggagaa      360 ctgtttaggt ggaatgtgag tgacctggga ggactgggat gtgggctgaa gaaccgctcc     420
tctgaaggcc caagttcacc ctcagggaag ctgatgagcc caaaactgta cgtgtgggcc     480
aaagatcggc ccgagatctg ggagggagaa cctccatgcc tgccacctag agacagcctg     540
aatcagagtc tgtcacagga tctgacaatg gccccgggt ccactctgtg gctgtcttgt      600
ggagtcccac ccgacagcgt gtccagaggc cctctgtcct ggacccacgt gcatcctaag     660
gggccaaaaa gtctgctgtc actggaactg aaggacgatc ggcctgccag agacatgtgg     720
gtcatggaga ctggactgct gctgccacga gcaaccgcac aggatgctgg aaaatactat     780
tgccaccggg gcaatctgac aatgtccttc atctggaga tcactgcaag gcccgtgctg      840
tggcactggc tgctgcgaac cggaggatgg aaggtcagtg ctgtgacact ggcatatctg     900
atctttgccc tgtgctccct ggtgggcatt ctgcatctgc agagagccct ggtgctgcgg     960
```

```
agaaagagaa agagaatgac tgacccaaca agaaggttt                           999
```

```
<210> SEQ ID NO 14
<211> LENGTH: 60
<212> TYPE: DNA
<213> ORGANISM: Artificial Sequence
<220> FEATURE:
<223> OTHER INFORMATION: 2A peptide

<400> SEQUENCE: 14
cgcggccgcg gccgagggag cctgctgaca tgtggcgatg tggaggaaaa cccaggacca    60
```

```
<210> SEQ ID NO 15
<211> LENGTH: 63
<212> TYPE: DNA
<213> ORGANISM: Artificial Sequence
<220> FEATURE:
<223> OTHER INFORMATION: signal peptide

<400> SEQUENCE: 15
atggagtttg actttcttg gttgtttttg gtggcaattc tgaagggtgt ccagtgtagc     60
agg                                                                  63
```

```
<210> SEQ ID NO 16
<211> LENGTH: 342
<212> TYPE: DNA
<213> ORGANISM: Artificial Sequence
<220> FEATURE:
<223> OTHER INFORMATION: 7G3 VL

<400> SEQUENCE: 16
gactttgtaa tgacccaatc tccaagctct cttacggtaa cggcaggaga gaaagtcacc    60
atgtcatgta aatccagtca atccctcttg aactcaggca accagaaaaa ttatcttacg   120
tggtatcttc aaaagccggg gcaacccca aaactcctga tctactgggc atcaaccagg    180
gagtccggcg tccccgaccg ctttacgggg agtggaagtg aaccgatttt accccttact   240
atcagcagcg tacaagcgga agacttggct gtgtattatt gtcaaaatga ttattcatat   300
ccctatactt tcggtggagg gactaaactt gaaattaaac ga                      342
```

```
<210> SEQ ID NO 17
<211> LENGTH: 24
<212> TYPE: DNA
<213> ORGANISM: Artificial Sequence
<220> FEATURE:
<223> OTHER INFORMATION: flex

<400> SEQUENCE: 17
ggcggaggaa gcggaggtgg gggc                                           24
```

```
<210> SEQ ID NO 18
<211> LENGTH: 354
<212> TYPE: DNA
<213> ORGANISM: Artificial Sequence
<220> FEATURE:
<223> OTHER INFORMATION: VH 7G3

<400> SEQUENCE: 18
gaagtccagt tgcaacaatc tggccctgag ttggtaaagc ccggagcctc tgtgaagatg    60
agttgtaagg cttcagggta tacatttaca gactattata tgaaatgggt caaacaatct   120
cacggtaaat ccttggagtg gattggcgat attatcccga gtaacggtgc cacgttctac   180
aaccagaagt tcaagggcaa ggcaacactg acggtagacc gcagcagcag cacggcgtat   240
```

-continued atgcacctga actcattgac ttcagaggat agtgcagttt actactgtac tcggagtcat        300
ttgctgagag cgagttggtt cgcctattgg ggtcagggca cactcgttac cgta             354

<210> SEQ ID NO 19
<211> LENGTH: 12
<212> TYPE: DNA
<213> ORGANISM: Artificial Sequence
<220> FEATURE:
<223> OTHER INFORMATION: link

<400> SEQUENCE: 19
tctgcaggat cc                                                            12

<210> SEQ ID NO 20
<211> LENGTH: 48
<212> TYPE: DNA
<213> ORGANISM: Homo sapiens

<400> SEQUENCE: 20
gaacttccta ctcaggggac tttctcaaac gttagcacaa acgtaagt                    48

<210> SEQ ID NO 21
<211> LENGTH: 21
<212> TYPE: DNA
<213> ORGANISM: Artificial Sequence
<220> FEATURE:
<223> OTHER INFORMATION: spacer

<400> SEQUENCE: 21
cccgccccaa gacccccac a                                                   21

<210> SEQ ID NO 22
<211> LENGTH: 126
<212> TYPE: DNA
<213> ORGANISM: Homo sapiens

<400> SEQUENCE: 22
cccgccccaa gacccccac acctgcgccg accattgctt ctcaacccct gagtttgaga        60
cccgaggcct gccggccagc tgccggcggg gccgtgcata caagaggact cgatttcgct      120
tgcgac                                                                  126

<210> SEQ ID NO 23
<211> LENGTH: 63
<212> TYPE: DNA
<213> ORGANISM: Homo sapiens

<400> SEQUENCE: 23
atctatatct gggcacctct cgctggcacc tgtggagtcc ttctgctcag cctggttatt        60
act                                                                      63

<210> SEQ ID NO 24
<211> LENGTH: 48
<212> TYPE: DNA
<213> ORGANISM: Homo sapiens

<400> SEQUENCE: 24
ctgtactgta atcaccggaa tcgccgccgc gtttgtaagt gtcccagg                    48

<210> SEQ ID NO 25
<211> LENGTH: 126
<212> TYPE: DNA

<213> ORGANISM: Homo sapiens

<400> SEQUENCE: 25
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 26
<211> LENGTH: 339
<212> TYPE: DNA
<213> ORGANISM: Homo sapiens

<400> SEQUENCE: 26
agagtgaagt tcagcaggag cgcagacgcc cccgcgtacc agcagggcca gaaccagctc      60
tataacgagc tcaatctagg acgaagagag gagtacgatg tttttggacaa gagacgtggc     120 cgggaccctg agatggggg gaaagccgaga aggaagaacc ctcaggaagg cctgtacaat      180
gaactgcaga aagataagat ggcggaggcc tacagtgaga ttgggatgaa aggcgagcgc     240 cggagggggca aggggcacga tggcctttac caggggtctca gtacagccac caaggacacc     300
tacgacgccc ttcacatgca ggccctgccc cctcgctag                            339

<210> SEQ ID NO 27
<211> LENGTH: 8
<212> TYPE: PRT
<213> ORGANISM: Artificial Sequence
<220> FEATURE:
<223> OTHER INFORMATION: linker

<400> SEQUENCE: 27

Gly Gly Gly Ser Gly Gly Gly Gly
1               5

<210> SEQ ID NO 28
<211> LENGTH: 4
<212> TYPE: PRT
<213> ORGANISM: Artificial Sequence
<220> FEATURE:
<223> OTHER INFORMATION: linker

<400> SEQUENCE: 28

Ser Ala Gly Ser
1

<210> SEQ ID NO 29
<211> LENGTH: 2610
<212> TYPE: DNA
<213> ORGANISM: Artificial Sequence
<220> FEATURE:
<223> OTHER INFORMATION: nucleotide sequence encoding CD123 chimeric
     antigen receptor

<400> SEQUENCE: 29
atgccaccac ctcgcctgct gttctttctg ctgttcctga cacctatgga ggtgcgacct      60
gaggaaccac tggtcgtgaa ggtcgaggaa ggcgacaatg ccgtgctgca gtgcctgaaa     120
ggcacttctg atgggccaac tcagcagctg acctggtcca gggagtctcc cctgaagcct      180
tttctgaaac tgagcctggg actgccagga ctgggaatcc acatgcgccc tctggctatc     240
tggctgttca tcttcaacgt gagccagcag atggaggat tctacctgtg ccagccagga     300
ccaccatccg agaaggcctg gcagcctgga tggaccgtca cgtggagggg gtctggagaa     360

```
ctgtttaggt ggaatgtgag tgacctggga ggactgggat gtgggctgaa gaaccgctcc    420
tctgaaggcc caagttcacc ctcagggaag ctgatgagcc caaaactgta cgtgtgggcc    480
aaagatcggc ccgagatctg ggagggagaa cctccatgcc tgccacctag agacagcctg    540
aatcagagtc tgtcacagga tctgacaatg gcccccgggt ccactctgtg gctgtcttgt    600
ggagtcccac ccgacagcgt gtccagaggc cctctgtcct ggacccacgt gcatcctaag    660
gggccaaaaa gtctgctgtc actggaactg aaggacgatc ggcctgccag agacatgtgg    720
gtcatggaga ctggactgct gctgccacga gcaaccgcac aggatgctgg aaaatactat    780
tgccaccggg gcaatctgac aatgtccttc catctggaga tcactgcaag gcccgtgctg    840
tggcactggc tgctgcgaac cggaggatgg aaggtcagtg ctgtgacact ggcatatctg    900
atcttttgcc tgtgctccct ggtgggcatt ctgcatctgc agagagccct ggtgctgcgg    960
agaaagagaa agagaatgac tgacccaaca agaaggtttc gcggccgcgg ccgagggagc    1020
ctgctgacat gtggcgatgt ggaggaaaac ccaggaccaa tggagtttgg actttcttgg    1080
ttgtttttgg tggcaattct gaagggtgtc cagtgtagca gggactttgt aatgacccaa    1140
tctccaagct ctcttacggt aacggcagga gagaaagtca ccatgtcatg taaatccagt    1200
caatccctct tgaactcagg caaccagaaa aattatctta cgtggtatct tcaaaagccg    1260
gggcaacccc caaaactcct gatctactgg gcatcaacca gggagtccgg cgtccccgac    1320
cgctttacgg gtagtggaag tggaaccgat tttacccta ctatcagcag cgtacaagcg    1380
gaagacttgg ctgtgtatta ttgtcaaaat gattattcat atccctatac tttcggtgga    1440
gggactaaac ttgaaattaa acgaggcgga ggaagcggag gtgggggcga agtccagttg    1500
caacaatctg gccctgagtt ggtaaagccc ggagcctctg tgaagatgag ttgtaaggct    1560
tcagggtata catttacaga ctattatatg aaatgggtca aacaatctca cggtaaatcc    1620
ttggagtgga ttggcgatat tatcccgagt aacggtgcca cgttctacaa ccagaagttc    1680
aagggcaagg caacactgac ggtagaccgc agcagcagca cggcgtatat gcacctgaac    1740
tcattgactt cagaggatag tgcagtttac tactgtactc ggagtcattt gctgagagcg    1800
agttggttcg cctattgggg tcagggcaca ctcgttaccg tatctgcagg atccgaactt    1860
cctactcagg ggactttctc aaacgttagc acaaacgtaa gtcccgcccc aagacccccc    1920
acacctgcgc cgaccattgc ttctcaaccc ctgagtttga cacccgaggc ctgccggcca    1980
gctgccggcg gggccgtgca tacaagagga ctcgatttcg cttgcgacat ctatatctgg    2040
gcacctctcg ctggcacctg tggagtcctt ctgctcagcc tggttattac tctgtactgt    2100
aatcaccgga atcgccgccg cgtttgtaag tgtcccaggg tcgacaaacg gggcagaaag    2160
aaactcctgt atatattcaa acaaccattt atgagaccag tacaaactac tcaagaggaa    2220
gatggctgta gctgccgatt ccagaagaa gaagaaggag gatgtgaact gagagtgaag    2280
ttcagcagga gcgcagacgc ccccgcgtac cagcagggcc agaaccagct ctataacgag    2340
ctcaatctag gacgaagaga ggagtacgat gtttttggaca agagacgtgg ccgggaccct    2400
gagatggggg gaaagccgag aaggaagaac cctcaggaag gcctgtacaa tgaactgcag    2460
aaagataaga tggcggaggc ctacagtgag attgggatga aggcgagcg ccggaggggc    2520 aagggcacg atggccttta ccagggtctc agtacagcca ccaaggacac ctacgacgcc    2580
cttcacatgc aggccctgcc ccctcgctag                                     2610
```

<210> SEQ ID NO 30
<211> LENGTH: 240

<212> TYPE: PRT
<213> ORGANISM: Artificial Sequence
<220> FEATURE:
<223> OTHER INFORMATION: scFv

<400> SEQUENCE: 30

```
Asp Phe Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys Arg Gly Gly Gly Ser Gly Gly Gly Gly Glu Val Gln Leu Gln Gln
        115                 120                 125

Ser Gly Pro Glu Leu Val Lys Pro Gly Ala Ser Val Lys Met Ser Cys
    130                 135                 140

Lys Ala Ser Gly Tyr Thr Phe Thr Asp Tyr Tyr Met Lys Trp Val Lys
145                 150                 155                 160

Gln Ser His Gly Lys Ser Leu Glu Trp Ile Gly Asp Ile Ile Pro Ser
                165                 170                 175

Asn Gly Ala Thr Phe Tyr Asn Gln Lys Phe Lys Gly Lys Ala Thr Leu
            180                 185                 190

Thr Val Asp Arg Ser Ser Ser Thr Ala Tyr Met His Leu Asn Ser Leu
            195                 200                 205

Thr Ser Glu Asp Ser Ala Val Tyr Tyr Cys Thr Arg Ser His Leu Leu
    210                 215                 220

Arg Ala Ser Trp Phe Ala Tyr Trp Gly Gln Gly Thr Leu Val Thr Val
225                 230                 235                 240
```

<210> SEQ ID NO 31
<211> LENGTH: 31
<212> TYPE: PRT
<213> ORGANISM: Artificial Sequence
<220> FEATURE:
<223> OTHER INFORMATION: aa. 12-42 of SEQ ID NO: 7

<400> SEQUENCE: 31

```
Ile Ala Ser Gln Pro Leu Ser Leu Arg Pro Glu Ala Cys Arg Pro Ala
1               5                   10                  15

Ala Gly Gly Ala Val His Thr Arg Gly Leu Asp Phe Ala Cys Asp
            20                  25                  30
```

<210> SEQ ID NO 32
<211> LENGTH: 11
<212> TYPE: PRT
<213> ORGANISM: Artificial Sequence
<220> FEATURE:
<223> OTHER INFORMATION: aa. 1-11 of SEQ ID NO:7

<400> SEQUENCE: 32

```
Pro Ala Pro Arg Pro Pro Thr Pro Ala Pro Thr
```

-continued

```
1               5               10
```

```
<210> SEQ ID NO 33
<211> LENGTH: 229
<212> TYPE: PRT
<213> ORGANISM: Mus musculus

<400> SEQUENCE: 33

Glu Ser Lys Tyr Gly Pro Pro Cys Pro Ser Cys Pro Ala Pro Glu Phe
1               5               10              15

Leu Gly Gly Pro Ser Val Phe Leu Phe Pro Pro Lys Pro Lys Asp Thr
                20              25              30

Leu Met Ile Ser Arg Thr Pro Glu Val Thr Cys Val Val Val Asp Val
            35              40              45

Ser Gln Glu Asp Pro Glu Val Gln Phe Asn Trp Tyr Val Asp Gly Val
        50              55              60

Glu Val His Asn Ala Lys Thr Lys Pro Arg Glu Glu Gln Phe Asn Ser
65              70              75              80

Thr Tyr Arg Val Val Ser Val Leu Thr Val Leu His Gln Asp Trp Leu
                85              90              95

Asn Gly Lys Glu Tyr Lys Cys Lys Val Ser Asn Lys Gly Leu Pro Ser
            100             105             110

Ser Ile Glu Lys Thr Ile Ser Lys Ala Lys Gly Gln Pro Arg Glu Pro
        115             120             125

Gln Val Tyr Thr Leu Pro Pro Ser Gln Glu Glu Met Thr Lys Asn Gln
    130             135             140

Val Ser Leu Thr Cys Leu Val Lys Gly Phe Tyr Pro Ser Asp Ile Ala
145             150             155             160

Val Glu Trp Glu Ser Asn Gly Gln Pro Glu Asn Asn Tyr Lys Thr Thr
                165             170             175

Pro Pro Val Leu Asp Ser Asp Gly Ser Phe Phe Leu Tyr Ser Arg Leu
            180             185             190

Thr Val Asp Lys Ser Arg Trp Gln Glu Gly Asn Val Phe Ser Cys Ser
        195             200             205

Val Met His Glu Ala Leu His Asn His Tyr Thr Gln Lys Ser Leu Ser
    210             215             220

Leu Ser Leu Gly Lys
225

<210> SEQ ID NO 34
<211> LENGTH: 222
<212> TYPE: PRT
<213> ORGANISM: Homo sapiens

<400> SEQUENCE: 34

Lys Glu Ala Cys Pro Thr Gly Leu Tyr Thr His Ser Gly Glu Cys Cys
1               5               10              15

Lys Ala Cys Asn Leu Gly Glu Gly Val Ala Gln Pro Cys Gly Ala Asn
                20              25              30

Gln Thr Val Cys Glu Pro Cys Leu Asp Ser Val Thr Phe Ser Asp Val
            35              40              45

Val Ser Ala Thr Glu Pro Cys Lys Pro Cys Thr Glu Cys Val Gly Leu
        50              55              60

Gln Ser Met Ser Ala Pro Cys Val Glu Ala Asp Asp Ala Val Cys Arg
65              70              75              80

Cys Ala Tyr Gly Tyr Tyr Gln Asp Glu Thr Thr Gly Arg Cys Glu Ala
```

-continued

```
                    85                    90                    95

Cys Arg Val Cys Glu Ala Gly Ser Gly Leu Val Phe Ser Cys Gln Asp
                100                   105                   110

Lys Gln Asn Thr Val Cys Glu Glu Cys Pro Asp Gly Thr Tyr Ser Asp
                115                   120                   125

Glu Ala Asn His Val Asp Pro Cys Leu Pro Cys Thr Val Cys Glu Asp
                130                   135                   140

Thr Glu Arg Gln Leu Arg Glu Cys Thr Arg Trp Ala Asp Ala Glu Cys
145                   150                   155                   160

Glu Glu Ile Pro Gly Arg Trp Ile Thr Arg Ser Thr Pro Pro Glu Gly
                165                   170                   175

Ser Asp Ser Thr Ala Pro Ser Thr Gln Glu Pro Glu Ala Pro Pro Glu
                180                   185                   190

Gln Asp Leu Ile Ala Ser Thr Val Ala Gly Val Val Thr Thr Val Met
                195                   200                   205

Gly Ser Ser Gln Pro Val Val Thr Arg Gly Thr Thr Asp Asn
    210                   215                   220
```

<210> SEQ ID NO 35
<211> LENGTH: 39
<212> TYPE: PRT
<213> ORGANISM: Homo sapiens

<400> SEQUENCE: 35

```
Ile Glu Val Met Tyr Pro Pro Pro Tyr Leu Asp Asn Glu Lys Ser Asn
1                   5                     10                    15

Gly Thr Ile Ile His Val Lys Gly Lys His Leu Cys Pro Ser Pro Leu
                20                    25                    30

Phe Pro Gly Pro Ser Lys Pro
        35
```

<210> SEQ ID NO 36
<211> LENGTH: 119
<212> TYPE: PRT
<213> ORGANISM: Artificial Sequence
<220> FEATURE:
<223> OTHER INFORMATION: hinge CH3

<400> SEQUENCE: 36

```
Glu Ser Lys Tyr Gly Pro Pro Cys Pro Ser Cys Pro Gly Gln Pro Arg
1                   5                     10                    15

Glu Pro Gln Val Tyr Thr Leu Pro Pro Ser Gln Glu Glu Met Thr Lys
                20                    25                    30

Asn Gln Val Ser Leu Thr Cys Leu Val Lys Gly Phe Tyr Pro Ser Asp
        35                    40                    45

Ile Ala Val Glu Trp Glu Ser Asn Gly Gln Pro Glu Asn Asn Tyr Lys
    50                    55                    60

Thr Thr Pro Pro Val Leu Asp Ser Asp Gly Ser Phe Phe Leu Tyr Ser
65                    70                    75                    80

Arg Leu Thr Val Asp Lys Ser Arg Trp Gln Glu Gly Asn Val Phe Ser
                85                    90                    95

Cys Ser Val Met His Glu Ala Leu His Asn His Tyr Thr Gln Lys Ser
                100                   105                   110

Leu Ser Leu Ser Leu Gly Lys
        115
```

<210> SEQ ID NO 37

```
<211> LENGTH: 27
<212> TYPE: PRT
<213> ORGANISM: Homo sapiens

<400> SEQUENCE: 37

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 38
<211> LENGTH: 41
<212> TYPE: PRT
<213> ORGANISM: Homo sapiens

<400> SEQUENCE: 38

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 39
<211> LENGTH: 36
<212> TYPE: PRT
<213> ORGANISM: Homo sapiens

<400> SEQUENCE: 39

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 40
<211> LENGTH: 8
<212> TYPE: PRT
<213> ORGANISM: Artificial Sequence
<220> FEATURE:
<223> OTHER INFORMATION: core sequence motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 40

Asp Xaa Glu Xaa Asn Pro Gly Pro
1               5

<210> SEQ ID NO 41
<211> LENGTH: 19
<212> TYPE: PRT
<213> ORGANISM: Artificial Sequence
<220> FEATURE:
<223> OTHER INFORMATION: peptide

<400> SEQUENCE: 41

Ala Glu Gly Arg Gly Ser Leu Leu Thr Cys Gly Asp Val Glu Glu Asn
1               5                   10                  15
```

-continued

Pro Gly Pro

<210> SEQ ID NO 42
<211> LENGTH: 19
<212> TYPE: PRT
<213> ORGANISM: Artificial Sequence
<220> FEATURE:
<223> OTHER INFORMATION: peptide

<400> SEQUENCE: 42

Ala Thr Asn Phe Ser Leu Leu Lys Gln Ala Gly Asp Val Glu Glu Asn
1               5                   10                  15

Pro Gly Pro

<210> SEQ ID NO 43
<211> LENGTH: 20
<212> TYPE: PRT
<213> ORGANISM: Artificial Sequence
<220> FEATURE:
<223> OTHER INFORMATION: peptide

<400> SEQUENCE: 43

Gln Cys Thr Asn Tyr Ala Leu Leu Lys Leu Ala Gly Asp Val Glu Ser
1               5                   10                  15

Asn Pro Gly Pro
            20

<210> SEQ ID NO 44
<211> LENGTH: 22
<212> TYPE: PRT
<213> ORGANISM: Artificial Sequence
<220> FEATURE:
<223> OTHER INFORMATION: peptide

<400> SEQUENCE: 44

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 45
<211> LENGTH: 21
<212> TYPE: PRT
<213> ORGANISM: Artificial Sequence
<220> FEATURE:
<223> OTHER INFORMATION: signal peptide

<400> SEQUENCE: 45

Met Ala Leu Pro Val Thr Ala Leu Leu Leu Pro Leu Ala Leu Leu Leu
1               5                   10                  15

His Ala Ala Arg Pro
            20

<210> SEQ ID NO 46
<211> LENGTH: 10
<212> TYPE: PRT
<213> ORGANISM: Artificial Sequence
<220> FEATURE:
<223> OTHER INFORMATION: linker

<400> SEQUENCE: 46

Pro Lys Pro Ser Thr Pro Pro Gly Ser Ser
1               5                   10

```
<210> SEQ ID NO 47
<211> LENGTH: 20
<212> TYPE: PRT
<213> ORGANISM: Artificial Sequence
<220> FEATURE:
<223> OTHER INFORMATION: linker

<400> SEQUENCE: 47

Pro Lys Pro Ser Thr Pro Pro Gly Ser Ser Pro Lys Pro Ser Thr Pro
1               5                   10                  15

Pro Gly Ser Ser
            20

<210> SEQ ID NO 48
<211> LENGTH: 9
<212> TYPE: PRT
<213> ORGANISM: Artificial Sequence
<220> FEATURE:
<223> OTHER INFORMATION: linker

<400> SEQUENCE: 48

Gly Gly Gly Gly Ser Gly Gly Gly Gly
1               5

<210> SEQ ID NO 49
<211> LENGTH: 20
<212> TYPE: PRT
<213> ORGANISM: Artificial Sequence
<220> FEATURE:
<223> OTHER INFORMATION: linker

<400> SEQUENCE: 49

Gly Gly Gly Gly Ser Gly Gly Gly Gly Ser Gly Gly Gly Gly Ser Gly
1               5                   10                  15

Gly Gly Gly Ser
            20

<210> SEQ ID NO 50
<211> LENGTH: 7
<212> TYPE: PRT
<213> ORGANISM: Artificial Sequence
<220> FEATURE:
<223> OTHER INFORMATION: linker

<400> SEQUENCE: 50

Gly Gly Gly Gly Ser Gly Gly
1               5

<210> SEQ ID NO 51
<211> LENGTH: 19
<212> TYPE: PRT
<213> ORGANISM: Artificial Sequence
<220> FEATURE:
<223> OTHER INFORMATION: signal peptide

<400> SEQUENCE: 51

Met Glu Phe Gly Leu Ser Trp Leu Phe Leu Val Ala Ile Leu Lys Gly
1               5                   10                  15

Val Gln Cys
```

CAR-CD123 VECTOR AND USES THEREOF

CROSS-REFERENCE TO RELATED APPLICATIONS

This application is a 371 of PCT/EP2020/071053, filed Jul. 24, 2020, which claims the benefit of European Patent Application No. 19188360.2, filed Jul. 25, 2019.

REFERENCE TO A SEQUENCE LISTING SUBMITTED ELECTRONICALLY VIA EFS-WEB

The content of the electronically submitted sequence listing, file name: 128-1254_SeqListing.txt; size: 37,760 bytes; and date of creation: Jan. 3, 2022, filed herewith, is incorporated herein by reference in its entirety.

TECHNICAL FIELD

The present invention concerns the generation of a novel chimeric antigen receptor (CAR)-CD123 vector for treatment of CD123+ tumors such as Acute Myeloid Leukemia (AML) [1], B-lymphoid leukaemia, blastic plasmacytoid dendritic neoplasms (BPDCN) [2], myelodysplastic syndrome [3] and hairy cell leukaemia [4].

BACKGROUND ART

Acute myeloid leukaemia (AML) is a heterogeneous clonal disorder characterized by the accumulation of abnormal immature blasts. The standard upfront chemotherapy AML treatment remains unchanged despite the advancement in understanding the leukemic biology. The current induction treatment—also called remission induction therapy— has the goal to clear the blood and bone marrow of immature blasts and bring about a complete remission. This treatment is usually given over 1 week and it can produce initial complete remission in almost 70% of young adult patients. However, 43% of patients will eventually relapse, and 18% never attain a complete remission at frontline induction treatment [5]. Immunotherapy with T-cells genetically modified to express CARs represents an innovative approach for AML.

In the last years, great interest has been focused in the identification of surface molecules that are preferentially expressed by AML cells and leukaemia stem cells (LSCs), in order to selectively target the tumor population while avoiding to affect the normal counterpart of hematopoietic stem/progenitor cells (HSPCs) [6].

CD123 is a glycoprotein of 360 amino acids also known as the transmembrane alpha subunit of the interleukin-3 receptor (IL-3Rα). Together with CD131, CD123 forms a high affinity IL-3R. Upon binding of IL-3, IL-3R promotes cell proliferation and survival [7].

The basal expression of CD123 is low to negligible in HSPCs, monocytes, a subset of dendritic cells (DC), named plasmacytoid DC-pDC [8] and endothelial cells [7] [9]. In contrast to the low expression on HSPCs, AML blasts widely overexpress CD123 [10] [11]. Moreover, CD123 overexpression on AML cells is associated with resistance to apoptosis, higher proliferating potential and poor prognosis [11] [12] [13].

Notably, CD123 is selectively overexpressed not only by AML blasts, but also by a quiescent population of AML LSCs, which has been shown to be one of the major players in chemotherapy drug resistance [14]. The differential expression of CD123 on normal HSCs and LSCs makes CD123 an attractive target for AML treatment.

Moreover, CD123 can be used to delineate MDS stem cells in patients at high risk for MDS and that the CD123-positive population is biologically distinct from normal hematopoietic stem cells [3].

Several antibody-based therapies have been developed targeting CD123 [15] [16] [14]. To date, the CD123 targeting therapies have been shown to be safe with no major adverse effects reported on hematopoiesis. Their anti-leukemic activities in humans are still being investigated.

An alternative AML therapeutic approach utilizes T cells expressing a CAR that redirects T cell specificity towards CD123 in an MHC-independent manner [16]. CAR T cells have the potential to proliferate and persist in humans for many years establishing a long-term tumor immunity. The first generation of CARs consist of a single-chain variable fragment (scFv) from a monoclonal antibody (e.g. anti-CD123) fused to the signaling domain of CD3ζ in the typical structure scFv-spacer-CD3z. In addition to the structure just described, the second-generation CARs have one co-stimulatory endodomain (e.g. CD28, or 41BB) that helps a) completing the T activation and b) avoiding apoptosis by promoting IL2 secretion.

Preclinical studies using second generation of CAR-T cells with anti-CD123-CD28ζ CAR and anti-CD123-41BBζ CAR T cells have demonstrated potent leukemia killing ability in vitro and in vivo however produced incongruous results regarding their myeloablative effect on healthy CD123+ cells [17] [18]. Multiple phase I trials (ClinicalTrials.gov number NCT03796390, NCT02937103, NCT03114670, NCT03672851) for CD123-directed CAR T cell therapy are currently underway to validate the effect and safety profiles.

Clearly, the anti-CD123 CAR T technology has great potential in the treatment of AML and other CD123+ tumors. While the benefits of incorporating at least one costimulatory domain to the CAR constructs are well established, the choice of scFv, and extracellular spacer domain, the T cell subsets, and the manufacturing process remain an area of intense research.

There is still the need for identifying a CAR T vector for the treatment of CD123+ tumors.

Moreover, CD123-redirected T cell treatment of mice engrafted with normal human hematopoietic cells resulted in profound myeloablation, raising concerns for hematologic toxicity in patients with AML who may be treated with such therapies.

Therefore it is still felt the need of an effective CAR therapy that does not present toxic effects on the patient.

DETAILED DESCRIPTION OF THE INVENTION

Inventors hypothesized that the incorporation of a novel suicide gene in the CAR.CD123 approach could minimize this bystander toxicity without impairing leukaemia control, thereby increasing the therapeutic window of anti-leukaemia CAR T cell or CAR Innate cell immunotherapy. In the light of the above, the present invention provides a novel second-generation CAR-CD123.

More specifically, the inventors constructed a CAR-CD123 structure (FIG. 1): ΔCD19-2A-CAR-CD123-ΔCD34.CD8.41BB.CD3ζ (Table 1: OPBG-242 vector) retroviral vector.

Inventors have designed a bicistronic vector, allowing the simultaneous expression of two transgenes, namely ΔCD19 and CARCD123 (ΔCD19-2A-CAR-CD123-ΔCD34. CD8.41BB. CD3ζ). Clonal retroviral producer cell line generates retroviral supernatant characterized by high titer (using PCR analysis for vector presence in the supernatant).

ΔCD19 represents the extracellular domain of human CD19 linked to the transmembrane portion. It has a triple function to help:

1) the selection of the genetically modified cells by clinical grade microbeads;

2) the phenotypic characterization of the genetically modified cells;

3) as inducible suicide gene, it can be targeted by FDA/ EMA approved anti-CD19 bite antibody (e.g. blinatumomab).

CAR molecule is based on the single chain of the fused VK-VL region of the monoclonal antibody 7G3 specific for the human antigen CD123, in frame with CD8 transmembrane domain and its endo domain, 4.1BB costimulatory domain and CD3ζ cytoplasmic domain for the transduction of the activator signal after antigen engagement. CAR construct was cloned in a retroviral vector after the gene cassette including the sequence of ΔCD19 through the use of a 2A sequence.

Thus, the functional and structural components important for ΔCD19-2A-CAR-CD123-ΔCD34.CD8.41BB.CD3 zeta (here after ΔCD19-2A-CAR.CD123-4.1BB-ζ) expression and activity are summarized in Table 1, and listed in the following:

5' LTR—Retroviral long terminal repeat at 5' end of vector (functions as promoter sequence)

ψ—Retroviral encapsidation signal (psi; necessary for packaging of RNA into virion particles)

SA—splice acceptor site

ΔCD19 consists of the optimized human (extracellular and transmembrane) domains of the CD19 marker 2A—encodes a synthetic 20 amino acid peptide from Thosea Asigna insect virus, which functions as a cleavable linker between the ΔCD19 protein and CAR proteins Signal peptide—short amino acid sequence to allow the correct translocation of the secretory proteins from the Endoplasmic Reticulum to the cellular membrane.

ΔCD34 consists of a short peptide derived from human CD34, helping to detect CAR+ cells after transduction CAR—CAR molecule based on the following elements indicated in the order of their location: single chain of the fused VL(k)-VH region of the monoclonal antibody 7G3 specific for the human antigen CD123, in frame with ΔCD34 domain, CD8 domains (spacer, TM, CD8Cyt), 4.1BB costimulatory domain and CD3ζ cytoplasmic domain.

3' LTR—Retroviral long terminal repeat at 3' end of vector (functions as terminator/polyadenylation sequences).

TABLE 1

| Functional Elements of OPBG-242 Plasmid | | |
| --- | --- | --- |
| Component | Start | End |
| 5'-LTR | 399 | 999 |
| ΔCD19 | 2282 | 3280 |
| 2A sequence | 3281 | 3340 |
| Signal Peptide | 3341 | 3403 |
| ScFv [VL(k)] 7G3 | 3404 | 3745 |
| Linker | 3746 | 3769 |
| ScFy [VH] 7G3 | 3770 | 4123 |

4

TABLE 1-continued

| Functional Elements of OPBG-242 Plasmid | | |
| --- | --- | --- |
| Component | Start | End |
| ΔCD34 | 4124 | 4183 |
| CD8 stalk (spacer) | 4184 | 4309 |
| CD8TM | 4310 | 4372 |
| CD8 Cyt | 4373 | 4420 |
| 4.1bb costimulation | 4427 | 4552 |
| CD3z | 4553 | 4891 |
| 3' LTR | 5069 | 5635 |
| $Amp^R$ promoter | 6848 | 6952 |
| $Amp^R$ | 6953 | 7813 |

Identity of the vector ΔCD19-2A-CAR.CD123-4.1BB-ζ:

A reference electronic vector sequence was assembled by combining the DNA sequence files for each component of the vector construct. Since the retroviral genome is RNA-based, sequence analysis was performed on the plasmid DNA used for transfection into the 293VEC cell line (initial step in retroviral product preparation). Bi-directional sequencing was performed by the inventors on the entire OPBG-242 vector. Sequencing runs were assembled using SnapGene software. No mismatched bases compared to the theoretical reference electronic sequence were identified. According to the present invention, a novel CD123-specific chimeric antigen receptor (ΔCD19-2A-CAR.CD123-4.1BB-ζ) of second generation is now provided. Particularly, the following clinical grade second generation of CAR CD123 SFG retroviral vectors is provided:

ΔCD19-2A-CAR.CD123-4.1BB-ζ (ΔCD19-2A-CAR-CD123-ΔCD34. CD8.41BB. CD3ζ) composed by:

ΔCD19 consists of the optimize human (extracellular and transmembrane) domains of the CD19 marker;

2A peptide—encodes a synthetic 20 amino acid peptide from Thosea Asigna insect virus, which functions as a cleavable linker between the ΔCD19 protein and CAR proteins;

A single chain variable fragment (scFv) from 7G3 hybridoma,

A trackable marker CD34 derived epitope (ΔCD34) of only 16 amino acid (aa) (as trackable marker) for a rapid identification by FACS (Fluorescence-activated cell sorting) System and/or selection by Cell Sorter System of gene modified cells;

A spacer represented by CD8 regions to avoid the immunogenic IgG4 Fc region.

a transmembrane domain from the transmembrane domain of CD8 to improve molecule stabilization A small portion of CD8 cytoplasmatic portion to facilitate the signal from to single chain to 4.1BB-CD3 zeta chain (4.1BB-ζ)

A costimulatory domain was added to the ΔCD19-2A-CAR.CD123-4.1BB-ζ vector: 4-1BB fused to CD3-ζ chain.

In ΔCD19-2A-CAR.CD123-4.1BB-ζ, the native nucleotide sequence of the trackable marker, the costimulatory domains and the CD3-ζ chain were modified to obtain a codon optimization to improve the efficient protein expression.

TABLE 2

Comparison among CD123 CARs. The table shows the differences between known
CD123 CARS and the one object of the present invention (Retroviral OPBG).

| Platform | CAR Generation | Single chain | Suicide gene/ selectable marker | trackable marker | Spacer | Transmembrane (TM) | Costimulatory domains | Reference |
|---|---|---|---|---|---|---|---|---|
| Lentiviral | 2 | 26292 or 32716 | none | EGFRt | IgG4 Fc region | CD28 | CD28 | [17] |
| Sleeping Beauty System | 2 | 26292, 32701, 32703 and 32716 | none | IgG4 Fc region | CD8α/IgG4 | CD28 | CD28 | [19] |
| Retroviral | 1 | 7G3 | none | IgG4 Fc region | IgG4 Fc region | CD28 | none | [14] |
| Retroviral (OPBG) | 2 | 7G3 | ΔCD19 (Codon optimized) | ΔCD34 (Codon optimized) | CD8 (Codon optimized) | CD8 (Codon optimized) | 4.1BB (Codon optimized) | non-applicable |

Figure 6:
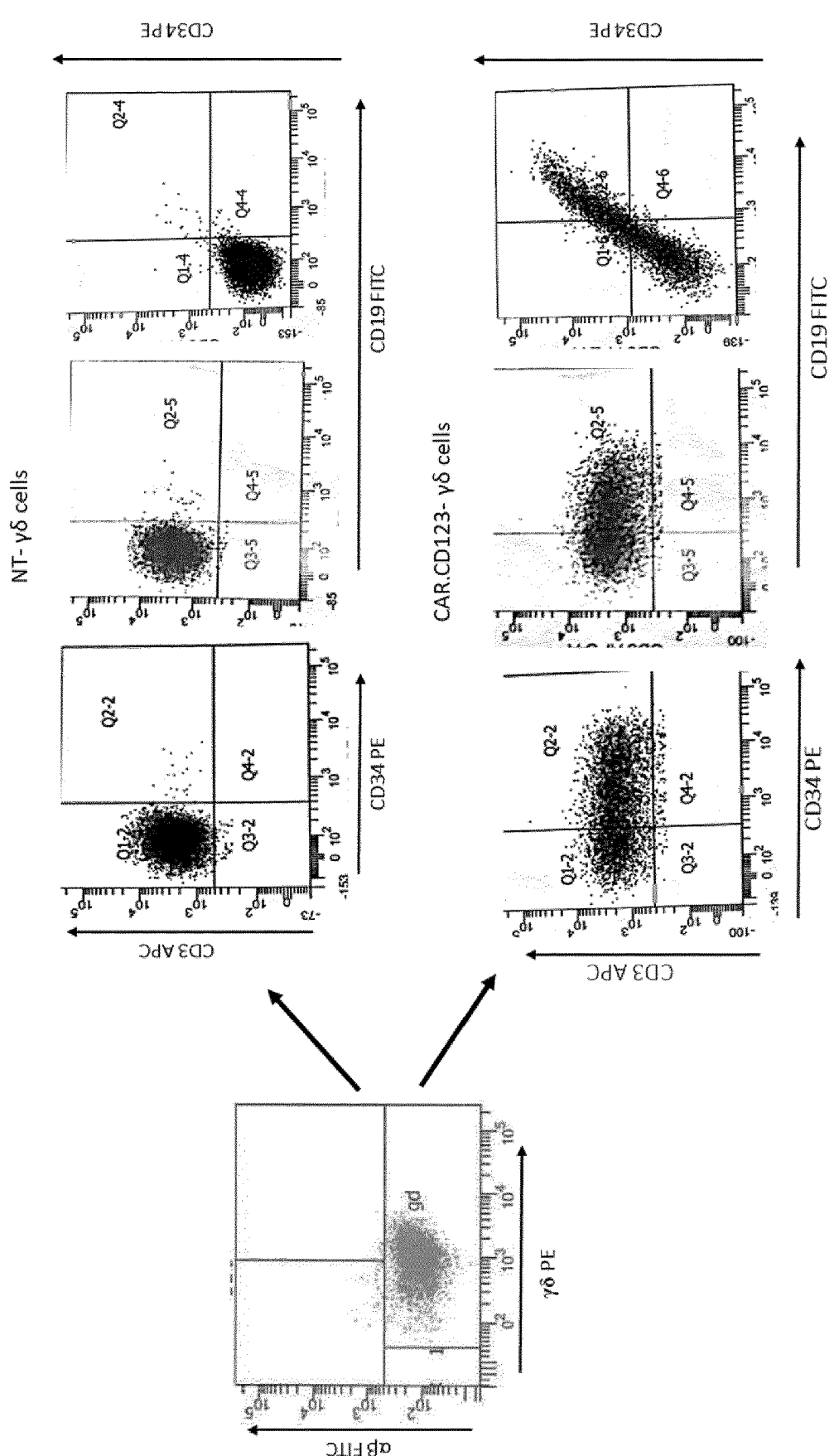

The present inventors herein report strong evidences about the retrovirus function anti-CD123 CAR to transduce different subpopulation: T cells (FIG. 2), NK cells (FIG. 4) and γδ cells (FIG. 6).

They clearly show that potent killing activity of gene modified CAR.CD123 T-cells (FIG. 8), CAR.CD123 NK cells (FIG. 9) CAR.CD123 γδ T cells (FIG. 11) in both in vitro model and in vivo model (described in detail in FIG. 14) on leukemia cell lines (THP-1).

Moreover, the present inventors herein show that ΔCD19 works as inducible suicide gene, after treatment of ΔCD19-2A-CAR.CD123-ΔCD34-CD8.4.1BB-ζ (CD123. CAR) T-cells (FIG. 15) or CAR.CD123 NK cells (FIG. 16) with anti-hCD19-CD3+bite antibodies. To note CD123.CAR T (FIG. 15C-D) and CD123.CAR NK cells (FIGS. 16B and 16E) were insensible to the negative control, namely bite anti-CD19B-Gal+ antibodies.

Therefore, the specificity of the suicide gene ΔCD19 in CD123 CAR NK cells is proved by the fact that the anti-hCD19-CD3+ bite is active only in presence of CD3 (T Cells) in the in vitro model (FIGS. 16C and 16F).

The introduction of two co-expressed markers (ΔCD34 and ΔCD19) (FIG. 1) in the present CAR allows the present inventors to study the genetically modified cells by considering a double approach, i.e. cytofluorimetric analysis based on the use of monoclonal antibody vs CD34 and/or CD19. This is particularly relevant in regard to the suicide gene approach. Indeed, if an anti-CD19 antibody is used to detect CAR.CD123 cells after anti-hCD19-CD3+ bite exposure, a masking effect related the bite engaging CD19 on CAR.CD123 modified cells may be encountered. Nevertheless, the inclusion of a double marker, represented by ΔCD34 represent a great advantage to analyzing the residual genetically modified cells after the treatment with the anti-hCD19-CD3+ bite.

Figure 17:
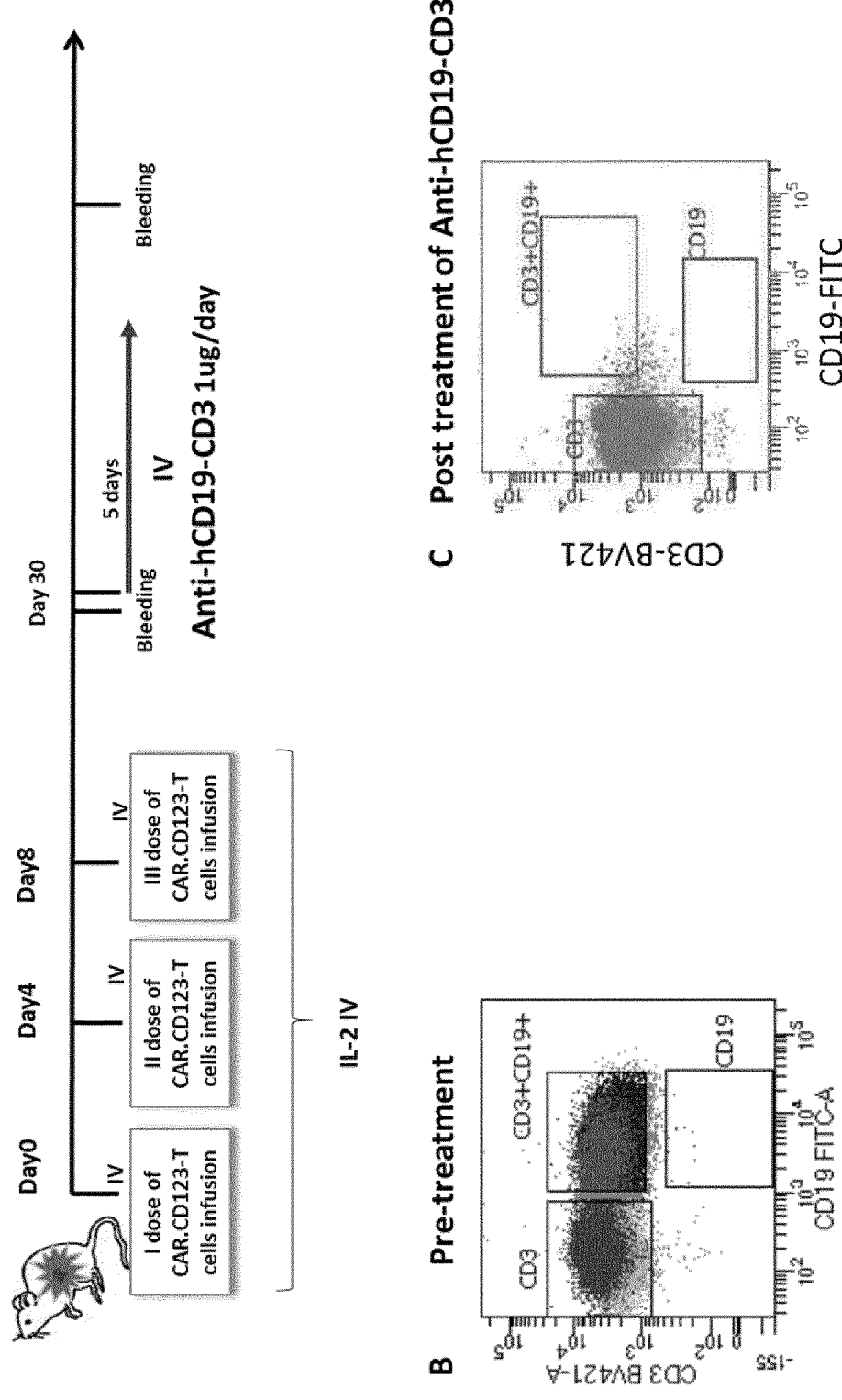

Data of the activity of the suicide gene was also proved in vivo, in NSG mice receiving ΔCD19-2A-CAR.CD123-4.1BB-ζ T cells (FIG. 17). As shown in FIG. 17A, mice received high number of ΔCD19-2A-CAR.CD123-4.1BB-ζ T cells (three consecutive infusions of $10 \times 10^6$/topo) also in the presence of IL2 administration (1000 U/mouse twice a week), to mimic the worst case of high expansion of genetically modified cells. After 30 days, when mice start to show clinical signs of sufferance, inventors performed blood bleeding to evaluate the level of expansion of ΔCD19-2A-CAR.CD123-4.1BB-ζ T cells (FIG. 17B). Then, mice were treated with bite anti-hCD19-CD3 for 5 consecutive days (1 ug/day). At day 40, inventors performed blood bleeding to evaluate the level of ΔCD19-2A-CAR.CD123-4.1BB-ζ T cells remaining after treatment. As shown in FIG. 17C, the amount of ΔCD19-2A-CAR.CD123-4.1BB-ζ T residual after bite anti-hCD19-CD3 treatment was negligible.

Therefore, it is an object of the present invention a CD123 chimeric antigen receptor molecule comprising or consisting of, from the N-terminus to the C-terminus:

a) ΔCD19 extracellular and transmembrane domains, such as: MPPPRLLFFLLFLTPMEVRPEE-PLVVKVEEGD-NAVLQCLKGTSDGPTQQLTWSRES PLKP-FLKLSLGLPGLGIHMRPLAIWLFIENVSQQM-GGFYLCQPGPPSEKAWQPGWT VNVEGSGEL-FRWNVSDLG-GLGCGLKNRSSEGPSSPSGKLMSPKLY-VWAKDRPEIW EGEPPCLPPRDSLNQSLSQDLTMAPG-STLWLSCGVPPDSVSRGPLSWTHVEIPKGPK SLLSLELKDDRPARDMVVVMETGLLL-PRATAQDAGKYYCHRGNLTMSFHLEITARP VLWHVVLLRTGGWKVSAVTLAYLIFCLCSLVG-ILEILQRALVLRRKRKRMTDPTRRF (SEQ ID NO:1) (Homo sapiens CD19 molecule (CD19), transcript variant 1, mRNA is disclosed in NCBI with the following Accession numbers: nucleotide NM_001178098.2 and Protein ID NO: NP_001171569.1);

b) 2A peptide—a synthetic 20 amino acid peptide derived from Thosea Asigna insect virus, such as RGR-GRGSLLTCGDVEENPGP (SEQ ID NO:2);

c) a signal peptide, such as MEFGLSWLFLVAILKGVQCSR (SEQ ID NO:3) (Homo sapiens mRNA for IgG H chain is disclosed in NCBI with the following Accession numbers nucleotide ID NO: AB776838.1 and Protein ID NO: BAN63131.1) which is in frame with:

d) an anti CD123 single chain antibody domain from 7G3 hybridoma comprising or consisting of the 7G3 VL$_{(K)}$ sequence: DFVMTQSPSSLTVTAGEKVTMSCK-SSQSLLNSGNQKNYLTWYLQKPGQPPKLLIY WASTRESGVPDRFTGSGSGTDFTLTISSVQAED-LAVYYCQNDYSYPYTFGGGTKLE IKR (SEQ ID NO:4) and linked by a second linker (GGGSGGGG (SEQ ID NO: 27)) to 7G3 VH sequence: EVQLQQSG-PELVKPGASVKMSCK- ASGYTFTDYYMKWVKQSHGKSLEWIGDIIPSN
GATFYNQKFKGKATLTVDRSSSTAYMHLNSLT-
SEDSAVYYCTRSHLLRASWFAY WGQGTLVTV
(SEQ ID NO:5) said 7G3 VL$_{(K)}$ and VH sequences
being linked by a third linker (SAGS (SEQ ID NO: 28))
to:

e) a trackable marker consisting of ΔCD34: ELPTQGTFSNVSTNVS (SEQ ID NO:6) (Homo sapiens CD34 gene for CD34 antigen is disclosed in NCBI with the following Accession numbers: nucleotide ID NO AB238231.1 and Protein ID NO: BAE46748.1);

f) a spacer consisting of extracellular portion (hinge) of CD8α: PAPRPPTPAPTIASQPLSLRPEACR-PAAGGAVHTRGLDFACD (SEQ ID NO: 7) (Homo sapiens T-cell surface glycoprotein CD8 alpha chain is disclosed in NCBI with the following Accession numbers: nucleotide ID NO: NM_001145873.1, also in NM_001768.6 and Protein ID NO: NP_001139345, also in NP_001759.3)

g) a trans-membrane domain consisting of CD8TM: IYI-WAPLAGTCGVLLLSLVIT (SEQ ID NO:8) (Homo sapiens CD8a molecule (CD8A) transcript variant 1, mRNA is disclosed in NCBI with the following Accession numbers: nucleotide NM_001145873.1, also in NM_001768.6 and Protein ID NO: NP_001139345, also in NP_001759.3)

h) a cytoplasmic domain consisting of CD8a cyt: LYCNHRNRRRVCKCPR (SEQ ID NO:9) (Homo sapiens CD8a molecule (CD8A) transcript variant 1, mRNA is disclosed in NCBI with the following Accession numbers: nucleotide ID NO NM_001768.6 and Protein ID NO: NP_001759.3) linked by short linker VD to:

i) a co-stimulatory signaling domain CD137 (4-1BB) sequence:

```
                                    (SEQ ID NO: 10)
KRGRKKLLYIFKQPFMRPVQTTQEEDGCSCRFPEEEEGGCEL
```

(Human receptor protein 4-1BB mRNA: nucleotide ID NO: U03397.1 and Protein NO: AAA53133.1);

j) and CD3-Zeta chain: RVKFSRSADAPA-YQQGQNQLYNELNLGRREEYDVLDKRR-GRDPEMGGKPRRKNP QEGLYNELQKDK-MAEAYSEIGMKGERRRGKGEIDGLYQGLSTATKD-TYDALHMQ ALPPR* (SEQ ID NO: 11) (Human T cell receptor zeta-chain mRNA, complete cds is disclosed in NCBI with the following Accession numbers: nucleotide ID NO: J04132.1 And Protein ID: AAA60394.1)

According to a preferred embodiment of the present invention ΔCD19-2A-CAR.CD123-4.1BB-ζ chimeric antigen receptor molecule is:

```
                                    (SEQ ID NO: 12)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL
```

```
                    -continued
IFCLCSLVGILHLQRALVLRRKRKRMTDPTRRFRGRGRGSLLTCGDVEEN

PGPMEFGLSWLFLVAILKGVQCSRDFVMTQSPSSLTVTAGEKVTMSCKSS

QSLLNSGNQKNYLTWYLQKPGQPPKLLIYWASTRESGVPDRFTGSGSGTD

FTLTISSVQAEDLAVYYCQNDYSYPYTFGGGTKLEIKRGGGSGGGGEVQL

QQSGPELVKPGASVKMSCKASGYTFTDYYMKWVKQSHGKSLEWIGDIIPS

NGATFYNQKFKGKATLTVDRSSSTAYMHLNSLTSEDSAVYYCTRSHLLRA

SWFAYWGQGTLVTVSAGSELPTQGTESNVSTNVSPAPRPPTPAPTIASQP

LSLRPEACRPAAGGAVHTRGLDFACDIYIWAPLAGTCGVLLLSLVITLYC

NHRNRRRVCKCPRVDKRGRKKLLYIFKQPFMRPVQTTQEEDGCSCRFPEE

EEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGL

STATKDTYDALHMQALPPR*
```

Namely, this sequence, herewith named also as ΔCD19-2A-CAR.CD123-4.1BB-ζ.

The present invention also provides a nucleotide sequence, which encodes CD123 chimeric antigen receptor described above.

According to an embodiment of the present invention, the nucleotide sequence is:

```
                                    (SEQ ID NO: 29)
ATGCCACCACCTCGCCTGCTGTTCTTTCTGCTGTTCCTGACACCTATGGA

GGTGCGACCTGAGGAACCACTGGTCGTGAAGGTCGAGGAAGGCGACAATG

CCGTGCTGCAGTGCCTGAAAGGCACTTCTGATGGGCCAACTCAGCAGCTG

ACCTGGTCCAGGGAGTCTCCCCTGAAGCCTTTTCTGAAACTGAGCCTGGG

ACTGCCAGGACTGGGAATCCACATGCGCCCTCTGGCTATCTGGCTGTTCA

TCTTCAACGTGAGCCAGCAGATGGGAGGATTCTACCTGTGCCAGCCAGGA

CCACCATCCGAGAAGGCCTGGCAGCCTGGATGGACCGTCAACGTGGAGGG

GTCTGGAGAACTGTTTAGGTGGAATGTGAGTGACCTGGGAGGACTGGGAT

GTGGGCTGAAGAACCGCTCCTCTGAAGGCCCAAGTTCACCCTCAGGGAAG

CTGATGAGCCCAAAACTGTACGTGTGGGCCAAAGATCGGCCCGAGATCTG

GGAGGGAGAACCTCCATGCCTGCCACCTAGAGACAGCCTGAATCAGAGTC

TGTCACAGGATCTGACAATGGCCCCCGGGTCCACTCTGTGGCTGTCTTGT

GGAGTCCCACCCGACAGCGTGTCCAGAGGCCCTCTGTCCTGGACCCACGT

GCATCCTAAGGGGCCAAAAAGTCTGCTGTCACTGGAACTGAAGGACGATC

GGCCTGCCAGAGACATGTGGGTCATGGAGACTGGACTGCTGCTGCCACGA

GCAACCGCACAGGATGCTGGAAAATACTATTGCCACCGGGGCAATCTGAC

AATGTCCTTCCATCTGGAGATCACTGCAAGGCCCGTGCTGTGGCACTGGC

TGCTGCGAACCGGAGGATGGAAGGTCAGTGCTGTGACACTGGCATATCTG

ATCTTTTGCCTGTGCTCCCTGGTGGGCATTCTGCATCTGCAGAGAGCCCT

GGTGCTGCGGAGAAAGAGAAAGAGAATGACTGACCCAACAAGAAGGTTTC

GCGGCCGCGGCCGAGGGAGCCTGCTGACATGTGGCGATGTGGAGGAAAAC

CCAGGACCAATGGAGTTTGGACTTTCTTGGTTGTTTTTGGTGGCAATTCT

GAAGGGTGTCCAGTGTAGCAGGGACTTTGTAATGACCCAATCTCCAAGCT
```

-continued

CTCTTACGGTAACGGCAGGAGAGAAAGTCACCATGTCATGTAAATCCAGT

CAATCCCTCTTGAACTCAGGCAACCAGAAAAATTATCTTACGTGGTATCT

TCAAAAGCCGGGGCAACCCCCAAAACTCCTGATCTACTGGGCATCAACCA

GGGAGTCCGGCGTCCCCGACCGCTTTACGGGTAGTGGAAGTGGAACCGAT

TTTACCCTTACTATCAGCAGCGTACAAGCGGAAGACTTGGCTGTGTATTA

TTGTCAAAATGATTATTCATATCCCTATACTTTCGGTGGAGGGACTAAAC

TTGAAATTAAACGAGGCGGAGGAAGCGGAGGTGGGGGCGAAGTCCAGTTG

CAACAATCTGGCCCTGAGTTGGTAAAGCCCGGAGCCTCTGTGAAGATGAG

TTGTAAGGCTTCAGGGTATACATTTACAGACTATTATATGAAATGGGTCA

AACAATCTCACGGTAAATCCTTGGAGTGGATTGGCGATATTATCCCGAGT

AACGGTGCCACGTTCTACAACCAGAAGTTCAAGGGCAAGGCAACACTGAC

GGTAGACCGCAGCAGCAGCACGGCGTATATGCACCTGAACTCATTGACTT

CAGAGGATAGTGCAGTTTACTACTGTACTCGGAGTCATTTGCTGAGAGCG

AGTTGGTTCGCCTATTGGGGTCAGGGCACACTCGTTACCGTATCTGCAGG

ATCCGAACTTCCTACTCAGGGGACTTTCTCAAACGTTAGCACAAACGTAA

GTCCCGCCCCAAGACCCCCCACACCTGCGCCGACCATTGCTTCTCAACCC

CTGAGTTTGAGACCCGAGGCCTGCCGGCCAGCTGCCGGCGGGGCCGTGCA

TACAAGAGGACTCGATTTCGCTTGCGACATCTATATCTGGGCACCTCTCG

CTGGCACCTGTGGAGTCCTTCTGCTCAGCCTGGTTATTACTCTGTACTGT

AATCACCGGAATCGCCGCCGCGTTTGTAAGTGTCCCAGGGTCGACAAACG

GGGCAGAAGAAaCTCCTGTATATATTCAAACAACCATTTATGAGACCAG

TACAAACTACTCAAGAGGAAGATGGCTGTAGCTGCCGATTTCCAGAAGAA

GAAGAAGGAGGATGTGAACTGAGAGTGAAGTTCAGCAGGAGCGCAGACGC

CCCCGCGTACCAGCAGGGCCAGAACCAGCTCTATAACGAGCTCAATCTAG

GACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAA

TGAACTGCAGAAAGATAAGATGGCGGAGGCCTACAGTGAGATTGGGATGA

AAGGCGAGCGCCGGAGGGGCAAGGGGCACGATGGCCTTTACCAGGGTCTC

AGTACAGCCACCAAGGACACCTACGACGCCCTTCACATGCAGGCCCTGCC

CCCTCGCTAG

Namely, this nucleotide sequence, which encodes the sequence named also as ΔCD19-2A-CAR.CD123-4.1BB-ζ, comprises the following sequences:

ΔCD19
(SEQ ID NO: 13)
ATGCCACCACCTCGCCTGCTGTTCTTTCTGCTGTTCCTGACACCTATGGA

GGTGCGACCTGAGGAACCACTGGTCGTGAAGGTCGAGGAAGGCGACAATG

CCGTGCTGCAGTGCCTGAAAGGCACTTCTGATGGGCCAACTCAGCAGCTG

ACCTGGTCCAGGGAGTCTCCCCTGAAGCCTTTTCTGAAACTGAGCCTGGG

ACTGCCAGGACTGGGAATCCACATGCGCCCTCTGGCTATCTGGCTGTTCA

TCTTCAACGTGAGCCAGCAGATGGGAGGATTCTACCTGTGCCAGCCAGGA

-continued

CCACCATCCGAGAAGGCCTGGCAGCCTGGATGGACCGTCAACGTGGAGGG

GTCTGGAGAACTGTTTAGGTGGAATGTGAGTGACCTGGGAGGACTGGGAT

GTGGGCTGAAGAACCGCTCCTCTGAAGGCCCAAGTTCACCCTCAGGGAAG

CTGATGAGCCCAAAACTGTACGTGTGGGCCAAAGATCGGCCCGAGATCTG

GGAGGGAGAACCTCCATGCCTGCCACCTAGAGACAGCCTGAATCAGAGTC

TGTCACAGGATCTGACAATGGCCCCCGGGTCCACTCTGTGGCTGTCTTGT

GGAGTCCCACCCGACAGCGTGTCCAGAGGCCCTCTGTCCTGGACCCACGT

GCATCCTAAGGGGCCAAAAAGTCTGCTGTCACTGGAACTGAAGGACGATC

GGCCTGCCAGAGACATGTGGGTCATGGAGACTGGACTGCTGCTGCCACGA

GCAACCGCACAGGATGCTGGAAAATACTATTGCCACCGGGGCAATCTGAC

AATGTCCTTCCATCTGGAGATCACTGCAAGGCCCGTGCTGTGGCACTGGC

TGCTGCGAACCGGAGGATGGAAGGTCAGTGCTGTGACACTGGCATATCTG

ATCTTTTGCCTGTGCTCCCTGGTGGGCATTCTGCATCTGCAGAGAGCCCT

GGTGCTGCGGAGAAAGAGAAAGAGAATGACTGACCCAACAAGAAGGTTT 2A peptide
(SEQ ID NO: 14)
CGCGGCCGCGGCCGAGGGAGCCTGCTGACATGTGGCGATGTGGAGGAAAA

CCCAGGACCA

Signal peptide
(SEQ ID NO: 15)
ATGGAGTTTGGACTTTCTTGGTTGTTTTTGGTGGCAATTCTGAAGGGTGT

CCAGTGTAGCAGG

VL (7G3)
(SEQ ID NO: 16)
GACTTTGTAATGACCCAATCTCCAAGCTCTCTTACGGTAACGGCAGGAGA

GAAAGTCACCATGTCATGTAAATCCAGTCAATCCCTCTTGAACTCAGGCA

ACCAGAAAAATTATCTTACGTGGTATCTTCAAAAGCCGGGGCAACCCCCA

AAACTCCTGATCTACTGGGCATCAACCAGGGAGTCCGGCGTCCCCGACCG

CTTTACGGGTAGTGGAAGTGGAACCGATTTTACCCTTACTATCAGCAGCG

TACAAGCGGAAGACTTGGCTGTGTATTATTGTCAAAATGATTATTCATAT

CCCTATACTTTCGGTGGAGGGACTAAACTTGAAATTAAACGA

Flex
(SEQ ID NO: 17)
GGCGGAGGAAGCGGAGGTGGGGGC

VH (7G3)
(SEQ ID NO: 18)
GAAGTCCAGTTGCAACAATCTGGCCCTGAGTTGGTAAAGCCCGGAGCCTC

TGTGAAGATGAGTTGTAAGGCTTCAGGGTATACATTTACAGACTATTATA

TGAAATGGGTCAAACAATCTCACGGTAAATCCTTGGAGTGGATTGGCGAT

ATTATCCCGAGTAACGGTGCCACGTTCTACAACCAGAAGTTCAAGGGCAA

GGCAACACTGACGGTAGACCGCAGCAGCAGCACGGCGTATATGCACCTGA

ACTCATTGACTTCAGAGGATAGTGCAGTTTACTACTGTACTCGGAGTCAT

TTGCTGAGAGCGAGTTGGTTCGCCTATTGGGGTCAGGGCACACTCGTTAC

CGTA

-continued

```
Link
(BamH1 restriction site and connection sequence)
                                     (SEQ ID NO: 19)
TCTGCAGGATCC ΔCD34
                                     (SEQ ID NO: 20)
GAACTTCCTACTCAGGGGACTTTCTCAAACGTTAGCACAAACGTAAGT Spacer (to ameliorate the recognition by using
anti-CD34 Ab)
                                     (SEQ ID NO: 21)
CCCGCCCCAAGACCCCCCACA Spacer (CD8a) extracellular
                                     (SEQ ID NO: 22)
CCCGCCCCAAGACCCCCCACACCTGCGCCGACCATTGCTTCTCAACCCT

GAGTTTGAGACCCGAGGCCTGCCGGCCAGCTGCCGGCGGGGCCGTGCATA

CAAGAGGACTCGATTTCGCTTGCGAC (ID NO: M12828.1)

CD8a (TM) transmembrane
                                     (SEQ ID NO: 23)
ATCTATATCTGGGCACCTCTCGCTGGCACCTGTGGAGTCCTTCTGCTCAG

CCTGGTTAT TACT (ID NO: M12828.1)

CD8a cytoplasmic (CD8a cyt)
                                     (SEQ ID NO: 24)
CTGTACTGTAATCACCGGAATCGCCGCCGCGTTTGTAAGTGTCCCAGG Link of connection
GTCGAC 4-1BB sequence (a co-stimulatory signaling domain)
                                     (SEQ ID NO: 25)
AAACGGGGCAGAAAGAAaCTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

CD3 Zeta chain
                                     (SEQ ID NO: 26)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAG
(nucleotide ID NO: J04132.1)
```

It is therefore an object of the invention a chimeric antigen receptor (CAR) molecule comprising, from the N-terminus to the C-terminus:
  a) an extracellular domain and transmembrane domain of human CD19 (ΔCD19),
  b) an antigen binding domain,
  c) a spacer domain,
  d) a transmembrane domain,
  e) a cytoplasmatic domain,
  It is included in the present invention also a CAR molecule comprising at least one of the above elements a)-e). It is also included in the present invention, a CAR molecule wherein said elements are present in any order.

Preferably the CAR molecule is a CD123 specific CAR (CD123 CAR) molecule and the antigen binding domain comprises VL (or VK) and/or VH from a monoclonal anti-CD123 antibody, more preferably the antigen binding domain comprises a single chain variable fragment (scFv) that specifically binds to CD123.

Preferably, the antigen binding domain comprises or consists of a sequence having at least 80% of identity to the 7G3 VK sequence: DFVMTQSPSSLTVTAGEKVTMSCK-SSQSLLNSGNQKNYLTWYLQKPGQPPKLLIYWASTR ESGVPDRFTGSGSGTDFTLTISSVQAEDLAVYYCQN-DYSYPYTFGGGTKLEIKR (SEQ ID NO:4) and/or of a sequence having at least 80% of identity to the 7G3 VH sequence: EVQLQQSGPELVKPGASVKMSCK-ASGYTFTDYYMKWVKQSHGKSLEWIGDIIPSN-GATFY NQKFKGKATLTVDRSSSTAYMHLNSLTSED-SAVYYCTRSHLLRASWFAYVVGQGTLVTV (SEQ ID NO:5), said VL and/or VK and/or VH being optionally humanized, wherein said VL(or VK) and VH are preferably separated by a first linker, more preferably said scFv comprises or consists of a VK comprising or consisting of SEQ ID NO: 4 and a VH comprising or consisting of SEQ ID NO: 5, more preferably the scFv comprises or consists of SEQ ID NO:30.

Preferably the above antigen binding domain may comprise antigen binding fragments of the sequence above disclosed, e.g. at least one of the CDR comprised in the VH and VL sequences. Said first linker preferably comprises or consists of the sequence GGGSGGGG (SEQ ID NO: 27) Preferably, the CAR molecule of the invention further comprises a trackable marker.

Said trackable marker is preferably comprised between the antigen binding domain and the spacer domain, preferably the the antigen binding domainand the trackable marker are separated by a second linker.

Preferably, said trackable marker comprises or consists of a CD34 derived epitope (ΔCD34) or of a peptide derived from murine Ig CH2CH3 region spacer (UNIPROTKB: P01861): ESKYGPPCPSCPAPE-FLGGPSVFLFPPKPKDTLMISRTPE-VTCVVVDVSQEDPEVQFNWYV DGVEVHNAKTKPREEQFN-STYRVVSVLTVLHQDWLNGKEYKCKVSNKGLPS-SIEKTISKA KGQPREPQVYTLPPSQEEMTKNQVSLT-CLVKGFYPSDIAVEWESNGQPENNYKTTPPVLD SDGSFFLYSRLTVDKSRWQEGNVFSCSVMHEALHN-HYTQKSLSLSLGK (SEQ ID NO: 33) or from Nerve Growth Factor Receptor (NGFR):

```
                                     (SEQ ID NO: 34)
KEACPTGLYTHSGECCKACNLGEGVAQPCGANQTVCEPCLDSVTFSDVVS

ATEPCKPCTECVGLQSMSAPCVEADDAVCRCAYGYYQDETTGRCEACRVC

EAGSGLVFSCQDKQNTVCEECPDGTYSDEANHVDPCLPCTVCEDTERQLR

ECTRWADAECEEIPGRWITRSTPPEGSDSTAPSTQEPEAPPEQDLIASTV

AGVVTTVMGSSQPVVTRGTTDN,
```

Preferably said trackable marker comprises or consist of a sequence having at least 80% of identity to SEQ ID NO:6 (ELPTQGTFSNVSTNVS), more preferably it comprises or consists of SEQ ID NO:6.

Preferably, the extracellular and transmembrane domains of human CD19 comprises or consist of a sequence having at least 80% of identity to SEQ ID NO: 1 (MPPPRLLF-FLLFLTPMEVRPEEPLVVKVEEGD-NAVLQCLKGTSDGPTQQLTWSRESPLKPF LKLSLGLPGLGIHMRPLAIWLFIFNVSQQMGGFYL-CQPGPPSEKAWQPGWTVNVEGSGEL FRWNVSDLG-GLGCGLKNRSSEGPSSPSGKLMSPKLYVWAKDRPEI-WEGEPPCLPPRDSLN QSLSQDLTMAPGSTLWLSCGVPPDSVSRG- PLSWTHVHPKGPKSLLSLELKDDRPARDMW
VMETGLLLPRATAQDAGKYYCHRGNLTMSFHLEIT-
ARPVLWHWLLRTGGWKVSAVTLA
YLIFCLCSLVGILHLQRALVLRRKRKRMTDPTRRF) or
functional fragments, derivatives and variants thereof.

Preferably the extracellular and transmembrane domains
of human CD19 comprises or consist of SEQ ID NO:1.

Preferably, the spacer domain comprises or consists of the
extacellular region of the CD8 alpha chain or of CD28 or the
hinge CH2-CH3 or the hinge CH3, preferably it comprises
or consists of a sequence having at least 80% of identity to
SEQ ID NO:7, or of a sequence having at least 80% of
identity to aa. 12-42 of SEQ ID NO: 7 corresponding to SEQ
ID NO:31 (IASQPLSLRPEACRPAAGGAVHTRGLD-
FACD) and/or of a sequence having at least 80% of identity
to aa. 1-11 of SEQ ID NO:7, corresponding to SEQ ID NO:
32 (PAPRPPTPAPT), or of a sequence having at least 80%
of identity to SEQ ID NO:7, or to IEVMYPPPYLD-
NEKSNGTIIHVKGKHLCPSPLFPGPSKP (SEQ ID NO:
35) or to ESKYGPPCPSCPAPE-
FLGGPSVFLEPPKPKDTLMISRTPE-
VTCVVVDVSQEDPEVQFNVVYV
DGVEVHNAKTKPREEQFN-
STYRVVSVLTVLHQDWLNGKEYKCKVSNKGLPS-
SIEKTISKA KGQPREPQVYTLPPSQEEMTKNQVSLT-
CLVKGFYPSDIAVEWESNGQPENNYKTTPPVLD
SDGSFFLYSRLTVDKSRWQEGNVFSCSVMHEALHN-
HYTQKSLSLSLGK, (SEQ ID NO:33); or to ESKY-
GPPCPSCPGQPREPQVYTLPPSQEEMTKNQVSLT-
CLVKGFYPSDIAVEWESNGQPEN
NYKTTPPVLDSDGSFFLY-
SRLTVDKSRWQEGNVFSCSVMHEALHN-
HYTQKSLSLSLGK (SEQ ID NO:36). More preferably the
spacer domain comprisises or consists of SEQ ID NO:7.

Preferably, the trans membrane domain comprises or
consists of a trasmembrane domain of a protein selected
from the group consisting of: CD8, alpha, beta or zeta chain
of the T-cell receptor, CD28, CD3 epsilon, CD45, CD4,
CD5, CD8, CD9, CD16, CD22, CD33, CD37, CD64, CD80,
CD86, CD134, CD137 and CD15, preferably it comprises
the trans membrane domain of a CD8 or CD28, more
preferably the trans membrane domain comprises or consists
of a sequence having at least 80% of identity to SEQ ID NO:
8 (IYIWAPLAGTCGVLLLSLVIT), or to FWVLVVVGGV-
LACYSLLVTVAFIIFWV (SEQ ID NO:37). More prefer-
ably the trans membrane domain comprises or consist of
SEQ ID NO: 8.

Preferably, the cytoplasmatic domain comprises or consist
of:
a) a region of CD8a cytoplasmatic portion and
b) a 4-1BB co-stimulatory domain (co-stimulatory sig-
nalling domain CD137) or a OX40 sequence or CD28
cytoplasmic sequence of and
c) a CD3-zeta chain.

Preferably, said cytoplasmatic domain comprises a region
of CD8a cytoplasmatic portion and/or a 4-1BB co-stimula-
tory domain and/or a CD3-zeta chain. More preferably the
cytoplasmatic domain comprises a region of CD8a cytoplas-
matic portion and a 4-1BB co-stimulatory domain and a
CD3-zeta chain.

Preferably said cytoplasmatic domain comprises a linker
between the CD8a cytoplasmic and the 4-1BB co-stimula-
tory domain.

Preferably the CD8a cytomplasmic portion comprises or
consists of a sequence having at least 80% of identity to SEQ
ID NO:9 (LYCNHRNRRRVCKCPR), even more preferably
it comprises SEQ ID NO:9.

Preferably, the co-stimulatory signalling domain CD137
(4-1BB) comprises or consists of a sequence having at least
80% of identity to SEQ ID NO:10 (KRGRKKLLY-
IFKQPFMRPVQTTQEEDGCSCRFPEEEEGGCEL), even
more preferably it comprises SEQ ID NO:10.

Preferably, the CD28 cytoplasmic sequence comprises or
consists of a sequence having at least 80% of identity to
RSKRSRLLHSDYMNMTPRRPGPTRKHYQPYAPPRD-
FAAYRS (SEQ ID NO:38).

Preferably, the OX40 sequence comprises or consists of a
sequence having at least 80% of identity to RDQRLPP-
DAHKPPGGGSFRTPIQEEQADAHSTLAKI (SEQ ID
NO:39).

Preferably, the CD3-Zeta chain comprises or consists of a
sequence having at least 80% of identity to SEQ ID NO: 11
(RVKFSRSADAPAYQQGQNQLYNELNLGRREEY-
DVLDKRRGRDPEMGGKPRRKNPQEGL YNELQKDK-
MAEAYSEIGMKGERRRGKGEDGLYQGLSTATKDTY-
DALEIMQALPPR*), even more preferably it comprises
SEQ ID NO:11.

Preferably, the sequence encoding the linker between the
CD8a cytomplasmic and the co-stimulatory signalling
domain CD137 (4-1BB) consists of 6 nucleotides. More
preferably it comprises or consists of a linker of two
aminoacid, preferably VD.

In this included in the present invention a CAR molecule
further comprising
a clevable linker, preferably a 2A peptide or an IRES,
and/or
a signal peptide and/or
a second linker, and/or
a trackable marker,
in any order.

Preferably, the CAR molecule according to any one of
previous claims further comprises between the extracellular
domain and transmembrane domain of human CD19 and the
antigen binding domain:
a cleavable linker, preferably a 2A peptide or an IRES,
and/or
a signal peptide.

Preferably the cleavable linker is a 2 A peptide comprising
or consisting of a sequence having at least 80% of identity
to SEQ ID NO:2 (RGRGRGSLLTCGDVEENPGP), more
preferably it comprises or consists of SEQ ID NO:2; or a 2A
self-cleaving peptide comprising a core sequence motif of
DxExNPGP (SEQ ID NO:40), preferably a peptide com-
prising or consisting of a sequence having at least 80% of
identity to: AEGRGSLLTCGDVEENPGP (SEQ ID NO:41);
ATNFSLLKQAGDVEENPGP (SEQ ID NO:42);
QCTNYALLKLAGDVESNPGP (SEQ ID NO:43) or to
VKQTLNFDLLKLAGDVESNPGP (SEQ ID NO:44).

Preferably, the signal peptide comprises or consist of a
sequence having at least 80% of identity to SEQ ID NO:3
(MEFGLSWLFLVAILKGVQCSR), more preferably it
comprises or consists of
SEQ ID NO:3; or it comprises or consist of a sequence
having at least 80% of identity to (SEQ ID NO: 45)
MALPVTALLLPLALLLHAARP.

Preferably, between the antigen binding domain and the
spacer domain there is:
a second linker and/or
a trackable marker.

Preferably the above cleavable linker, signal peptide and the first linker, and the second linker and the trackable marker are present in the CAR molecule from the N-terminus to the C-terminus.

Preferably the second linker between the antigen binding domain and the trackable marker comprises or consists of the sequence SAGS (SEQ ID NO: 28). Preferably the sequence coding for at least one of: the extracellular domain and transmembrane domain of human CD19, the trackable marker, the spacer domain, the transmembrane domain and the co-stimulatory domain is codon optimized.

Preferably, the CAR molecule according to the inventions comprises or consists of from the N-terminus to the C-terminus:

a) an extracellular domain and transmembrane domain of human CD19, b) a cleavable linker, c) a signal peptide, d) an antigen binding domain, e) a trackable marker, f) a spacer domain, g) a transmembrane domain, h) a cytoplasmatic domain.

In a preferred embodiment, the CAR molecule as above defined comprises or consists of from the N-terminus to the C-terminus:

a) an extracellular domain and transmembrane domain of human CD19, as above defined, b) a cleavable linker, as above defined c) a signal peptide, as above defined d) an antigen binding domain, as above defined e) a trackable marker, as above defined f) a spacer domain, as above defined g) a transmembrane domain, as above defined h) a cytoplasmatic domain, as above defined.

Preferably the CAR molecule comprises or consists of a sequence having at least 80% of identity to SEQ ID NO:12 (MPPPRLLFFLLFLTPMEVRPEEPLVVKVEEGD-NAVLQCLKGTSDGPTQQLTWSRESPLKPF LKLSLGLPGLGIHMRPLAIWLFIFNVSQQMGGFYL-CQPGPPSEKAWQPGWTVNVEGSGEL FRWNVSDLG-GLGCGLKNRSSEGPSSPSGKLMSPKLYVWAKDRPEI-WEGEPPCLPPRDSLN QSLSQDLTMAPGSTLWLSCGVPPDSVSRG-PLSWTHVEIPKGPKSLLSLELKDDRPARDMW VMETGLLLPRATAQDAGKYYCHRGNLTMSFHLEIT-ARPVLWHWLLRTGGWKVSAVTLA YLIFCLCSLVGILHLQRALVLRRKRKRMTDPTRRFR-GRGRGSLLTCGDVEENPGPMEFGLS WLFLVAILKGVQCSRDFVMTQSPSSLTVTAGEKV-TMSCKSSQSLLNSGNQKNYLTWYLQ KPGQPPKLLIYWAST-RESGVPDRFTGSGSGTDFTLTISSVQAED-LAVYYCQNDYSYPYTFG GGTKLEIKRGGGSGGG-GEVQLQQSGPELVKPGASVKMSCKASGYTFTDY-YMKWVKQSH GKSLEWIGDIIPSNGAT-FYNQKFKGKATLTVDRSSSTAYMHLNSLTSED-SAVYYCTRSHLL RASW-FAYWGQGTLVTVSAGSELPTQGTFSNVSTNVSPA-PRPPTPAPTIASQPLSLRPEACRP AAGGAVHTRGLD-FACDIYIWAPLAGTCGVLLLSLVITLYCNEI-RNRRRVCKCPRVDKRGRK KLLY-IFKQPFMRPVQTTQEEDGCSCRFPEEEEGGCELRVK-FSRSADAPAYQQGQNQLYNE LNLGRREEY-DVLDKRRGRDPEMGGKPRRKNP QEGLYNEL QKDK- MAEAYSEIGMKGERR RGKGHDGLYQGLSTATKDTY-DALHMQALPPR*), more preferably it comprises or consists of SEQ ID NO:12.

Another object of the invention is an isolated nucleic acid molecule encoding the chimeric antigen receptor molecule according to any one of the previous claims, wherein said isolated nuelcic acid molecule is preferably operatively linked to expression control sequences. Preferably said molecule comprises at least one sequence having at least 80% of identity to one the following sequence: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, even more preferably said molecule comprises or consists of a sequence having at least 80% of identity to SEQ ID NO: 29, more preferably said molecule comprises or consists SEQ ID NO: 29. A further object of the invention is a vector comprising the isolated nucleic acid molecule as above defined, preferably an expression vector, more preferably the vector comprises an exogenous promoter controlling the expression of the CAR, preferably said vector is a DNA, an RNA vector, a plasmid, a lentivirus vector, adenoviral vector, retrovirus vector or non-viral vector.

Another object of the invention is an engineered immune cell, preferably a T cell, more preferably an alfa/beta and/or gamma/delta T cell, or NK cells or NK-T cells or combinations thereof, even more preferably of human origin, comprising the vector as above defined or the isolated nucleic acid molecule as above defined or expressing, preferably at the cell surface, at least one CAR molecule as above defined. A further object of the invention is a pharmaceutical composition comprising the isolated nucleic acid molecule as above defined or the vector as above defined or the cell as above defined with at least one pharmaceutically acceptable excipiente and/or adjuvant.

Another object of the invention is a CAR molecule as above defined, the isolated nucleic acid molecule as above defined, the vector as above defined, the cell as above defined or the pharmaceutical composition as above defined for medical use, preferably for use in the treatment of CD123+ cancers, more preferably of acute myeloid or B-lymphoid leukemias, blastic plasmacytoid dendritic neoplasms (BPDCN), myelodispastic syndrome or hairy cell leukemia or for use before, after or during a haematopoietic stem cell transplantion.

An other object of the invention is an extracellular domain and transmembrane domain of human CD19, preferably as defined above, for medical use, preferably for use as inducer of death in a cell genetically modified with said extracellular domain and transmembrane domain of human CD19, preferably after the exposure of said cell to at least one agent that binds the extracellular and transmembrane domains of human CD19 on the transduced cell. Preferably the agent that binds the extracellular and transmembrane domains of human CD19 is an antibody, small molecule, polypeptide, nucleic acid, or combination thereof, more preferably a monoclonal antibody. More preferably the agent that binds the extracellular and transmembrane domains of human CD19 is an anti-CD19 antibody, including (Bi-specific T-cell engagers) bite antibodies, e.g. Blinatumomab.

Preferably the activity of the antibody is not relying on ADCC mechanism of action. In the context of the present invention, the ablation of the genetic modified cells is preferably carried out by a mechanism that is not based on ADCC.

Preferably the antibody is a bi-specific antibody engaging ΔCD19 and CD3 to activate cytotoxicity in ΔCD19+ cells.

Preferably the cell genetically modified is a transduced cell, such as is an immune cell or a stem cell, comprising a nucleic acid that encodes the extracellular domain and transmembrane domain of human CD19 and a nucleic acid that encodes one or more therapeutic gene products.

Preferably the therapeutic gene product is an engineered receptor, more preferably it is a T-cell receptor, chimeric antigen receptor (CAR), cytokine receptor, homing receptor, or chemokine receptor, preferably said engineered receptor targets a cancer antigen.

Preferably, the nucleic acid that encodes the extracellular domain and transmembrane domain of human CD19 and the nucleic acid that encodes the therapeutic gene product are the same nucleic acid molecule, preferably said nucleic acid molecule is a vector, more preferably it is a viral vector, such as a retroviral vector, lentiviral vector, adenoviral vector, or adeno-associated viral vector. Preferably the nucleic acid that encodes the extracellular domain and transmembrane domain of human CD19 is at N-terminal of the nucleic acid molecule, preferably it is at the N-terminal of a CAR molecule.

Preferably the CAR is the CAR according to the invention.

Another object of the invention is a composition comprising a transduced cell, such as is an immune cell or a stem cell, comprising a nucleic acid that encodes the extracellular domain and transmembrane domain of human CD19 and a nucleic acid that encodes one or more therapeutic gene products, preferably said therapeutic gene product is an engineered receptor, more preferably it is a T-cell receptor, chimeric antigen receptor (CAR), cytokine receptor, homing receptor, or chemokine receptor, preferably said engineered receptor targets a cancer antigen.

Preferably, the nucleic acid that encodes the extracellular domain and transmembrane domain of human CD19 and the nucleic acid that encodes the therapeutic gene product are the same nucleic acid molecule, preferably said nucleic acid molecule is a vector, more preferably it is a viral vector, such as a retroviral vector, lentiviral vector, adenoviral vector, or adeno-associated viral vector. Another object of the invention is a method of inducing death for a transduced cell expressing the extracellular and transmembrane domains of human CD19, comprising the step of providing an effective amount of at least one agent that binds the extracellular and transmembrane domains of human CD19 on the transduced cell, said agent being preferably an antibody, small molecule, polypeptide, nucleic acid, or combination thereof, more preferably a monoclonal antibody, more preferably an anti-CD19 antibody, including bite antibodies, e.g. Blinatumomab Preferably the cell further expresses an engineered receptor, preferably a T-cell receptor or a CAR, more preferably the engineered receptor targets a cancer antigen.

Preferably the CAR is the CAR according to the invention.

A further object of the invention is a vector comprising a sequence that encodes the extracellular domain and transmembrane domain of human CD19 and that encodes an engineered receptor. Preferably the sequence of the vector that encodes the extracellular domain and transmembrane domain of human CD19 and sequence of the vector that encodes the engineered receptor are separated on the vector by a cleavable linker, preferably as defined above. Preferably the sequence of the vector that encodes the extracellular domain and transmembrane domain of human CD19 is upstream respect of the sequence of the vector that encodes the engineered receptor.

Preferably the engineered receptor is a CAR, more preferably a CAR according to the invention. In the context of the present invention the extracellular domain and transmembrane domain of human CD19 comprises or consist of a sequence having at least 80% of identity to SEQ ID NO: 1 (MPPPRLLFFLLFLTPMEVRPEEPLVVKVEEGD-NAVLQCLKGTSDGPTQQLTWSRESPLKPF LKLSLGLPGLGIIIMRPLAIWLFIENVSQQMGGFYL-CQPGPPSEKAWQPGWTVNVEGSGEL FRWNVSDLG-GLGCGLKNRSSEGPSSPSGKLMSPKLYVWAKDRPEI-WEGEPPCLPPRDSLN QSLSQDLTMAPGSTLWLSCGVPPDSVSRG-PLSWTHVEIPKGPKSLLSLELKDDRPARDMW VMETGLLLPRATAQDAGKYYCHRGNLTMSFEILEIT-ARPVLWHVVLLRTGGWKVSAVTLA YLIFCLCSLVG-ILEILQRALVLRRKRKRMTDPTRRF) or functional fragments, derivatives and variants thereof, more preferably the extracellular and transmembrane domains of human CD19 comprise or consist of SEQ ID NO:1.

Preferably the method of the invention occurs in vivo in an individual with a medical condition and the individual has been provided a therapy for the medical condition that comprises a plurality of the transduced cells, preferably the medical condition is cancer. Preferably the agent is provided to the individual upon onset of one or more adverse events from the therapy.

It is another object of the invention a method of reducing the risk of toxicity of a cell therapy for an individual, comprising the step of modifying the cells of the cell therapy to express the extracellular and transmembrane domains of human CD19.

Preferably the therapy is for cancer.

Preferably the cell therapy comprises an engineered receptor that targets an antigen.

Another object of the invention is the extracellular domain and transmembrane domain of human CD19, in particular as defined above, for medical use, preferably for use as inducer of death in a cell genetically modified with said extracellular domain and transmembrane domain of human CD19, preferably after the exposure of said cell to anti-CD19 antibody, including bite antibodies, e.g. Blinatumomab.

In the context of the present invention, preferably the activity of the antibody is not relying on ADCC mechanism of action and/or the ablation of the genetic modified cells is preferably carried out by a mechanism that is not based on ADCC.

Preferably the antibody is a bi-specific antibody engaging ΔCD19 and CD3 to activate cytotoxicity in ΔCD19+ cells.

The cell genetically modified with said extracellular domain and transmembrane domain of human CD19 may be a cell comprising and/or and/or transformed and/or transduced and/or expressing the CAR molecule of the invention, e.g. a CAR-T cells or a CAR-NK cell or a cell as defined above, The choice of the linker depends to the cloning strategy (insertion of a restriction enzyme).

Preferably, the above nucleic acid is integrated into the genome of the cell.

The CAR-cells may be allogeneic cells or autologous cells and/or HLA matched to the subject. In the context of the present invention, the cancer or tumor preferably expresses CD123. Preferably the polynucleotide is under the control of an endogenous promoter. Preferably the extracellular and transmembrane domains of human CD19 is encoded by a sequence that comprises or consist of a sequence having at least 80% of identity with SEQ ID NO: 13, preferably by a sequence comprising or consisting of SEQ ID NO:13.

It is another object of the invention a viral particle comprising the isolated nuelcic acid molecule as above defined or the vector as above defined.

The antigen binding domain is preferably a chimeric antigen binding domain.

The chimeric antigen receptors (CAR) of the invention may comprise an antibody or antibody fragment engineered for specific binding to a CD123 protein or fragments thereof. In one aspect, the antigen binding domain of the CAR comprises a human or humanized CD123 antibody or antibody fragment thereof. Preferably, the antigen binding domain of the CAR comprises human CD123 antibody fragment comprising an scFv, preferably a human CD123 scFv.

Preferably, the antigen binding domain of the CAR comprises an anti CD123 single chain antibody domain from 7G3 hybridoma, preferably comprising or consisting of the 7G3 VL(or VK) sequence and 7G3 VH sequence, preferably linked by a linker.

In one aspect, the CAR123 binding domain comprises the scFv portion provided in SEQ ID NO: 30

(DFVMTQSPSSLTVTAGEKVTMSCKSSQSLLNSGNQKNYLTWYLQKPGQPP

KLLIYWASTRESGVPDRFTGSGSGTDFTLTISSVQAEDLAVYYCQNDYSYP

YTFGGGTKLEIKRGGGSGGGGEVQLQQSGPELVKPGASVKMSCKASGYTFT

DYYMKWVKQSHGKSLEWIGDIIPSNGATFYNQKFKGKATLTVDRSSSTAYM

HLNSLTSEDSAVYYCTRSHLLRASWFAYWGQGTLVTV).

In the context of the present invention, the element "extracellular domain and transmembrane domain" of human CD19, may be as defined above or it may be ΔCD19 extracellular and transmembrane domains from other transcript variants of Homo sapiens CD19 molecule (CD19) (e.g. those from the variants disclosed in NCBI with the following Accession numbers NM_001770 and NP_001761.3 (isoform 2), XM_017023893.1 and XP_016879382.1 (isoform X2), XM_011545981.2 and XP_011544283.1 (isoform X3)).

In the context of the present invention, the cleavable linker, may be the 2A peptide as defined above or it may be a 2A self-cleaving peptide having a core sequence motif of DxExNPGP (SEQ ID NO: 40), preferably a peptide selected from the group consisting of: T2A (derived from thosea asigna virus 2): AEGRGSLLTCGDVEENPGP (SEQ ID NO:41) (nucleotide ID NO: AF062037.1 and Protein ID NO: YP_009665206.1); P2A (derived from porcine teschovirus-1 2A): ATNFSLLKQAGDVEENPGP (SEQ ID NO:42) (nucleotide ID NO: AB038528.1 and Protein ID NO: BAB32828.1); E2A (derived from equine rhinitis A virus): QCTNYALLKLAGDVESNPGP (SEQ ID NO:43) (nucleotide ID NO: NC_039209.1 and Protein ID NO: YP_009513027.1) and F2A (derived from foot-and-mouth disease virus): VKQTLNFDLLKLAGDVESNPGP (SEQ ID NO:44) (nucleotide ID NO: AY593825.1 and Protein ID NO: AAT01768.1). Preferably it is used the modified polynucleotide T2A RGRGRGSLLTCGDVEENPGP (SEQ ID NO: 2) (nucleotide ID NO: AF062037.1 and Protein ID NO: YP_009665206.1).

Other standard signal peptides for CAR constructs may be used instead of the above signal peptide, included different signal peptides derived from protein characterized by high expression, e.g. CD8a signal peptide MALPVTALLLPLALLLHAARP (SEQ ID NO:45) (nucleotide ID NO: NM_001768; and Protein ID NO: NP_001759.3).

Other trackable markers may be used instead of the trackable markers above disclosed, e.g. a peptide derived from murine Ig CH2CH3 region spacer (UNIPROTKB: P01861): ESKYGPPCPSCPAPE-FLGGPSVFLFPPKPKDTLMISRTPE-VTCVVVDVSQEDPEVQFNWYV DGVEVHNAKTKPREEQFNS TYRVVSVLTVLHQDWLNGKEYKCKVSNKGLPSSI-EKTISKA KGQPREPQVYTLPPSQEEMTKNQVSLT-CLVKGFYPSDIAVEWESNGQPENNYKTTPPVLD SDGSFFLYSRLTVDKSRWQEGNVFSCSVMHEALHN-HYTQKSLSLSLGK (SEQ ID NO:33) or a peptide derived from NGFR: KEACPTGLYTHSGECCK-ACNLGEGVAQPCGANQTV-CEPCLDSVTFSDVVSATEPCKPCTE CVGLQSM-SAPCVEADDAVCRCAYGYYQDETTGRCEACRVC-EAGSGLVFSCQDKQNTVC EECPDGTYS-DEANHVDPCLPCTVCEDTERQLRECTRWADAECEE-IPGRWITRSTPPEGSDS TAPSTQEPEAPPEQDLI-ASTVAGVVTTVMGSSQPVVTRGTTDN (SEQ ID NO:34) (nucleotide ID NO: AK313654.1 and Protein ID NO: BAG36408.1).

Other spacer domains (or sequences) may be used instead of the spacer sequence disclosed above e.g. a spacer domain selected from the group consisting of stalk sequences from membrane bound proteins, including examples of CD28 stalk: CD28: IEVMYPPPYLD-NEKSNGTIIHVKGKHLCPSPLFPGPSKP (SEQ ID NO: 35) (nucleotide ID NO: AJ517504.1 and Protein ID NO: CAD57003.1); the hinge CH2-CH3 (UNIPROTKB: P01861): ESKYGPPCPSCPAPEP-FLGGPSVFLFPPKPKDTLMISRTPE-VTCVVVDVSQEDPEVQFNWYV DGVEVHNAKTKPREEQFN-STYRVVSVLTVLHQDWLNGKEYKCKVSNKGLPSSI-EKTISKA KGQPREPQVYTLPPSQEEMTKNQVSLT-CLVKGFYPSDIAVEWESNGQPENNYKTTPPVLD SDGSFFLYSRLTVDKSRWQEGNVFSCSVMHEALHN-HYTQKSLSLSLGK, (SEQ ID NO:33); the hinge CH3 (UNIPROTKB:P01861): ESKYGPPCP-SCPGQPREPQVYTLPPSQEEMTKNQVSLT-CLVKGFYPSDIAVEWESNGQPEN NYKTTPPVLDSDGSFFLY-SRLTVDKSRWQEGNVFSCSVMHEALHN-HYTQKSLSLSLGK (SEQ ID NO:36), preferably a CD 8stalk: PAPRPPTPAPTIASQPLSLRPEACR-PAAGGAVHTRGLDFACD (SEQ ID NO: 7) (nucleotide ID NO: M12828.1 and Protein ID NO: AAB04637.1).

Other transmembrane domains may be used instead of the those disclosed above, e.g. CD28TM: FWVLVVVGGVLA-CYSLLVTVAFIIFWV (SEQ ID NO:37) (nucleotide ID NO: J02988.1 and Protein ID AAA60581.1).

The above co-stimulatory signaling domain may be a peptide comprising or consisting of CD28 cytoplasmic sequence: RSKRSRLLHSDYMNMTPRRPGP-TRKHYQPYAPPRDFAAYRS (SEQ ID NO:38) (nucleotide ID NO: AF222341.1 and Protein ID NO: AAF33792.1) or CD137 (4-1BB) sequence: KRGRKKLLY-IFKQPFMRPVQTTQEEDGCSCRFPEEEEGGCEL (SEQ ID NO: 10) (nucleotide ID NO: U03397.1 and Protein NO: AAA53133.1) or OX40 sequence RDQRLPP-DAHKPPGGGSFRTPIQEEQADAHSTLAKI (SEQ ID NO:39) (nucleotide ID NO: NM 003327.3 and Protein NO: NP_003318.1).

The domains herein disclosed of the CAR are contiguous with and in the same reading frame to form a single fusion protein.

In the context of the present invention an immune cell may be a T cell, a NK cell, NKT cell, iNKT cell, B cell, regulatory T cell, monocyte, macrophage, dendritic cell, or mesenchymal stromal cell. The cells of the invention (e.g., an immune effector cell, e.g., a T cell or a NK cell) may be engineered to express a CAR, wherein the CAR-expressing cell (e.g., "CAR-T" or CAR-expressing NK cell) exhibits an antitumor property. In one aspect a cell is transformed with the CAR and the at least part of the CAR is expressed on the cell surface. In some embodiments, the cell (e.g., an immune cell, an immune effector cell, e.g., T cell or NK cell, engineered immune cell, such as T cell, more preferably an alfa/beta or gamma/delta T cell, or NK cells or NK-T cells or combinations thereof) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., immune effector cell, e.g., T cell or NK cell) is transfected with a nucleic acid, e.g., mRNA, cDNA, DNA, encoding a CAR. In some such embodiments, the cell may transiently express the CAR. Preferably, the CD123 binding domain, e.g., the human or humanized CD123 binding domain, of the CAR is a scFv antibody fragment. In one aspect, such antibody fragments are functional in that they retain the equivalent binding affinity, e.g., they bind the same antigen with comparable efficacy, as the IgG antibody having the same heavy and light chain variable regions. In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan. The antibodies of the invention may be incorporated into a chimeric antigen receptor (CAR). In one aspect, the CD123 binding domain, e.g., humanized or human CD123 binding domain, portion of a CAR of the invention is encoded by a transgene whose sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

"CD123" refers to an antigenic determinant known to be detectable on leukemia precursor cells. The human and murine amino acid and nucleic acid sequences can be found in a public database, such as GenBank, UniProt and Swiss-Prot. For example, the amino acid sequence of human CD123 can be found at Accession No. NP_002174.1 and the nucleotide sequence encoding of the human CD123 can be found at Accession No. NM_002183.4. In one aspect the antigen-binding portion of the CAR recognizes and binds an antigen within the extracellular domain of the CD 123 protein. In one aspect, the CD 123 protein is expressed on a cancer cell. As used herein, the term "Chimeric Antigen Receptor" or alternatively a "CAR" refers to a recombinant polypeptide construct comprising at least an antigen binding domain, a transmembrane domain and a cytoplasmic domain (also referred to herein as "an intracellular signaling domain") comprising a functional signaling domain derived from a stimulatory molecule as defined herein. In one aspect, the stimulatory molecule is the zeta chain associated with the T cell receptor complex. In one aspect, the intracellular signaling domain further comprises one or more functional signaling domains derived from at least one costimulatory molecule as defined below. In one aspect, the costimulatory molecule is chosen from 4-1BB (i.e., CD137), CD27, and/or CD28. In one aspect, the CAR comprises a chimeric fusion protein comprising an antigen recognition domain, a transmembrane domain and a cytoplasmic signaling domain comprising a functional signaling domain derived from a stimulatory molecule. In one aspect, the CAR comprises a chimeric fusion protein comprising an antigen recognition domain, a transmembrane domain and a cytoplasmic signaling domain comprising a functional signaling domain derived from a costimulatory molecule and a functional signaling domain derived from a stimulatory molecule. In one aspect, the CAR comprises a chimeric fusion protein comprising an antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain, e.g., a scFv) during cellular processing and localization of the CAR to the cellular membrane. As used herein, the terms intracellular, cytoplasmic and cytoplasmatic are used interchangeably. The term "signaling domain" refers to the functional portion of a protein which acts by transmitting information within the cell to regulate cellular activity via defined signaling pathways by generating second messengers or functioning as effectors by responding to such messengers. The term "antibody," as used herein, refers to a protein, or polypeptide sequence derived from an immunoglobulin molecule which specifically binds with an antigen, e.g., non-covalently, reversibly, and in a specific manner. An antibody can be polyclonal or monoclonal, multiple or single chain, or an intact immunoglobulin, and may be derived from natural sources or from recombinant sources. An antibody can be a tetramer of immunoglobulin molecule. For example, a naturally occurring IgG antibody is a tetramer comprising at least two heavy (H) chains and two light (L) chains (where the L chain can consist of either a κ or a λ chain)[20] inter-connected by disulfide bonds. Each heavy chain is comprised of a heavy chain variable region (abbreviated herein as VH) and a heavy chain constant region. The heavy chain constant region is comprised of three domains, CHI, CH2 and CH3. Each light chain is comprised of a light chain variable region (abbreviated herein as VL) and a light chain constant region. The light chain constant region is comprised of one domain, CL. In the context of the present invention the term VL include also VK. The VH and VL regions can be further subdivided into regions of hyper variability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes, but is not limited to, monoclonal antibodies, human antibodies, humanized antibodies, camelid antibodies, and chimeric antibodies. The antibodies can be of any isotype/class (e.g., IgG, IgE, IgM, IgD, IgA and IgY), or subclass (e.g., IgGl, IgG2, IgG3, IgG4, IgAl and IgA2). The term "antibody fragment" refers to at least one portion of an intact antibody, or recombinant variants thereof, and refers to the antigen binding domain, e.g., an antigenic determining variable regions of an intact antibody that is sufficient to confer recognition and specific binding of the antibody fragment to a target, such as an antigen. Examples of antibody fragments include, but are not limited to, Fab, Fab', F(ab')2, and Fv fragments, single chain or "scFv" antibody fragments, linear antibodies, single domain antibodies such as sdAb (either VL or VH), camelid VHHdomains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VK or VL and VH variable regions in either order, e.g., with respect to the N-terminal and C-terminal ends of the polypeptide, the scFv may comprise VL(or VK)-linker-VH or may comprise VH-linker-VL(or VK). The portion of the CAR composition of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York) [21, 22]. In one aspect, the antigen binding domain of a CAR composition of the invention comprises an antibody fragment. In a further aspect, the CAR comprises an antibody fragment that comprises a scFv. By the term "recombinant antibody" as used herein, is meant an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant or synthetic DNA or amino acid sequence technology which is available and well known in the art. The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

The phrase "disease associated with expression of CD 123" as used herein includes but is not limited to, a disease associated with expression of CD 123 or condition associated with cells which express CD123 including, e.g., a proliferative disease such as a cancer or malignancy or a precancerous condition such as a myelodysplasia, a myelodysplasia syndrome or a preleukemia; or a noncancer related indication associated with cells which express CD123. In one aspect, a cancer associated with expression of CD 123 is a hematological cancer. In one aspect, a hematological cancer includes but is not limited to AML, myelodysplasia syndrome, ALL, hairy cell leukemia, Prolymphocytic leukemia, Chronic myeloid leukemia, Hodgkin lymphoma, Blastic plasmacytoid dendritic cell neoplasm, and the like. Further disease associated with expression of CD 123 expression include, but are not limited to, e.g., atypical and/or non-classical cancers, malignancies, precancerous conditions or proliferative diseases associated with expression of CD123. Non-cancer related indications associated with expression of CD 123 may also be included.

In the present invention, one or more amino acid residues within a CAR of the invention can be replaced with other amino acid residues from the same side chain family and the altered CAR can be tested for the ability to bind CD 123 using functional assays known to the skilled man.

A "stimulatory molecule," as the term is used herein, means a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or IT AM. Examples of an IT AM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d. In a specific CAR molecule of the invention, the intracellular signaling domain in any one or more CAR molecules of the invention comprises an intracellular signaling sequence, e.g., a primary signaling sequence of CD3-zeta. In a specific CAR of the invention, the primary signaling sequence of CD3-zeta is the human sequence (SEQ ID NO:11), or the equivalent residues from a non-human species, e.g., mouse, rodent, monkey, ape and the like. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule. A primary intracellular signaling domain can comprise a signaling motif which is known as an immunoreceptor tyrosine-based activation motif or IT AM. Examples of IT AM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

As used herein "zeta" or alternatively "zeta chain", "CD3-zeta" or "TCR-zeta" is e.g. defined as the protein provided as NCBI Acc. No. J04132.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplamic domain of the zeta chain that are sufficient to functionally transmit an initial signal necessary for T cell activation. A "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to, an MHC class I molecule, BTLA and a Toll ligand receptor, as well as OX40, CD27, CD28, CDS, ICAM-1, LFA-1 (CD11a/CD18) and 4-1BB (CD137). A costimulatory intracellular signaling domain can be derived from the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like. The intracellular signaling domain can comprise the entire intracellular portion, or the entire native intracellular signaling domain, of the molecule from which it is derived, or a functional fragment thereof. As used herein "4-1BB" refers to a member of the TNFR superfamily with an amino acid sequence e.g. provided as NCBI No. AAA53133.1, or the equivalent residues from a non-human species, e.g., mouse, rodent, monkey, ape and the like. In one aspect, the "4-1BB costimulatory domain" is the human sequence or the equivalent residues from a non-human species, e.g., mouse, rodent, monkey, ape and the like. In one aspect, the "4-1BB costimulatory domain" is the sequence provided as SEQ ID NO:10 or the equivalent residues from a non-human species, e.g., mouse, rodent, monkey, ape and the like. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g. rRNA, tRNA and mRNA) or a defined sequence of amino acids and the biological properties resulting therefrom. Thus, a gene, cDNA, or RNA encodes a protein if transcription and translation of mRNA corresponding to that gene, cDNA, or RNA produces the protein in a cell or other biological system. Both the coding strand, the nucleotide sequence of which is identical to the mRNA sequence, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins or a RNA may also include introns to the extent that the nucleotide sequence encoding the protein may in some version contain an intron(s). The term "vector" or "transfer vector" refers to a polynucleotide which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to further include non-plasmid and non-viral compounds which facilitate transfer of nucleic acid into cells, such as, for example, a polylysine compound, a liposome, and the like. Examples of viral vectors include, but are not limited to, adenoviral vectors, adeno-associated virus vectors, retroviral vectors, lentiviral vectors, and the like. "Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g. naked or contained in liposomes) and viruses (e.g. lentiviruses, retroviruses, adenoviruses, and adeno-associated viruses) that incorporate the recombinant polynucleotide. The term "homologous" or "identity" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. A "lentiviral vector" is a vector derived from at least a portion of a lentivirus genome, including especially a self-inactivating lentiviral vector as provided in Milone et al [23]. Other Examples or lentivirus vectors that may be used in the clinic include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art. The term "operably linked" or alternatively "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame. The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues [24] [25] [26]. As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" (as the above domain, marker, peptide, linker, . . . ) include, for example, biologically active or functional fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, a synthetic peptide, or a combination thereof. The term "promoter" as used herein is defined as a DNA sequence recognized by the synthetic machinery of the cell, or introduced synthetic machinery, required to initiate the specific transcription of a polynucleotide sequence. As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. A "linker" as used in the context of an scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser-Gly-Gly-Gly-Gly)n (SEQ ID NO:27), where n is a positive integer equal to or greater than 1. For example, n=1, n=2, n=3. n=4, n=5 and n=6, n=7, n=8, n=9 and n=10. Also included within the scope of the invention are linkers described in WO2012/138475, incorporated herein by reference in its entirety.

The linker which links the VL (or VK) and the VH sequences is preferably chosen from the group consisting of a rigid linker prolines-rich, such as mouse IgG3 upper hinge (mIgG3UFl): PKPSTPPGSS (SEQ ID NO:46), (mIgG3UH)2: PKPSTPPGSSPKPSTPPGSS (SEQ ID NO:47), or a flexible linker glycines-rich, such as (G45)2 linker: GGGGSGGGG (SEQ ID NO:48), (G45)4 linker: GGGGSGGGGSGGGGSGGGGS (SEQ ID NO:49), G4SG2 linker GGGGSGG (SEQ ID NO:50) or G3SG4 linker: GGGSGGGG (SEQ ID NO:27), preferably GGGSGGGG (SEQ ID NO:27). The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny. The cells include an engineered immune cell, preferably a T cell, more preferably an alfa/beta or gamma/delta T cell, or NK cell or NK-T cell or combinations thereof. As used herein, "transient" refers to expression of a non-integrated transgene for a period of hours, days or weeks, wherein the period of time of expression is less than the period of time for expression of the gene if integrated into the genome or contained within a stable plasmid replicon in the host cell. The phrase "under transcriptional control" or "operatively linked" as used herein means that the promoter is in the correct location and orientation in relation to a polynucleotide to control the initiation of transcription by RNA polymerase and expression of the polynucleotide. By the term "specifically binds," as used herein, is meant an antibody or antigen binding fragment thereof, or a ligand, which recognizes and binds with a cognate binding partner (e.g. a stimulatory and/or costimulatory molecule present on a T cell) protein present in a sample, but which antibody, antigen binding fragment thereof or ligand does not substantially recognize or bind other molecules in the sample. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range. The term at least 80% identity, includes something with 80%, 81%, 82, 83%, 84%, 85%, 86%, 87%, 88%, 89%, 90%, 91%, 92%, 93%, 94%, 95%, 96%, 97%, 98% 99% or 100% identity.

Included in the present invention are also nucleic acid and amino acid sequences derived from the sequences shown above, e.g. functional fragments, mutants, derivatives, analogues, and sequences having a % of identity of at least 70% with the above sequences.

The herein disclosed domains, peptide, molecule, marker, region, portion, sequence and chain include functional derivatives, fragments, variants, the corresponding protein encoded from a corresponding orthologous or homologous genes, functional mutants, functional fragments or analogues, isoforms thereof.

The term polynucleotide and polypeptide also include derivatives and functional fragments thereof. The polynucleotide may be synthesized using oligonucleotide analogs or derivatives (e.g., inosine or phosphorothioate nucleotides).

In the context of the present invention, the genes/proteins as above defined are preferably characterized by the sequences identified by their NCBI Gene ID and Gen Bank Accession numbers. The term gene herein also includes corresponding orthologous or homologous genes, isoforms, variants, allelic variants, functional derivatives, functional fragments thereof. The expression "protein" is intended to include also the corresponding protein encoded from a corresponding orthologous or homologous genes, functional mutants, functional derivatives, functional fragments or analogues, isoforms thereof.

In the context of the present invention, the term "polypeptide" or "protein" includes:

i. the whole protein, allelic variants and orthologs thereof;
ii. any synthetic, recombinant or proteolytic functional fragment;
iii. any functional equivalent, such as, for example, synthetic or recombinant functional analogues.

For "functional" it is intended that it maintains its activity. For example a functional fragment, derivative or variant of the extracellular domain and transmembrane domain of human CD19 should maintain its activity as a suicide gene or of inducing death in a transduced cell expressing the extracellular and transmembrane domains of human CD19.

As used herein, the designation "functional derivative" or "functional variant" denotes, in the context of a functional derivative of a sequence whether a nucleic acid or amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid generally has chemico-physical properties which are similar to that of the substituted amino acid. The similar chemico-physical properties include, similarities in charge, bulkiness, hydrophobicity, hydrophilicity and the like. The term "functional derivatives" is intended to include "fragments", "segments", "variants", "analogs" or "chemical derivatives" of the subject matter of the present invention. In an embodiment, the above-mentioned derivative, variant or fragment is an "antigenic derivative, variant or fragment" (e.g., which has the capacity to induce/elicit an immune response against the parental antigen).

Thus, the term "variant" refers herein to a protein or nucleic acid molecule which is substantially similar in structure and biological activity to the protein or nucleic acid of the present invention but is not limited to a variant which retains all of the biological activities of the parental protein, for example.

The functional derivatives of the present invention can be synthesized chemically or produced through recombinant DNA technology. All these methods are well known in the art.

As used herein, "chemical derivatives" is meant to cover additional chemical moieties not normally part of the subject matter of the invention. Such moieties could affect the physico-chemical characteristic of the derivative (e.g. solubility, absorption, half-life, decrease of toxicity and the like). Such moieties are exemplified in Remington's Pharmaceutical Sciences (1980). Methods of coupling these chemical-physical moieties to a polypeptide or nucleic acid sequence are well known in the art. As used herein "fragments" refers to polypeptides having preferably a length of at least 10 amino acids, more preferably at least 15, at least 17 amino acids or at least 20 amino acids, even more preferably at least 25 amino acids or at least 37 or 40 amino acids, and more preferably of at least 50, or 100, or 150 or 200 or 250 or 300 or 350 or 400 or 450 or 500 amino acids.

The invention will be illustrated by means of non-limiting examples in reference to the following figures.

FIG. 1: Design of the ΔCD19-2A-CAR.CD123-ΔCD34-CD8.4.1BB-ζ (CAR.CD123-T) Retroviral Vector The expression cassette of CAR.CD123 shown in cartoon. The bicistronic vector is composed by two transgenes, namely ΔCD19 and CARCD123. ΔCD19 consists of (extracellular and transmembrane) domains of the CD19 marker. It is connected to CARCD123 by 2A peptide. The scFv of CD123 was cloned in frame with CD8a spacer-transmembrane domain and a costimulatory domain represented by 4-1BB, as well as the signaling domain CD3-zeta chain (ζ). As a trackable marker, ΔCD34 was added.

Figure 2:
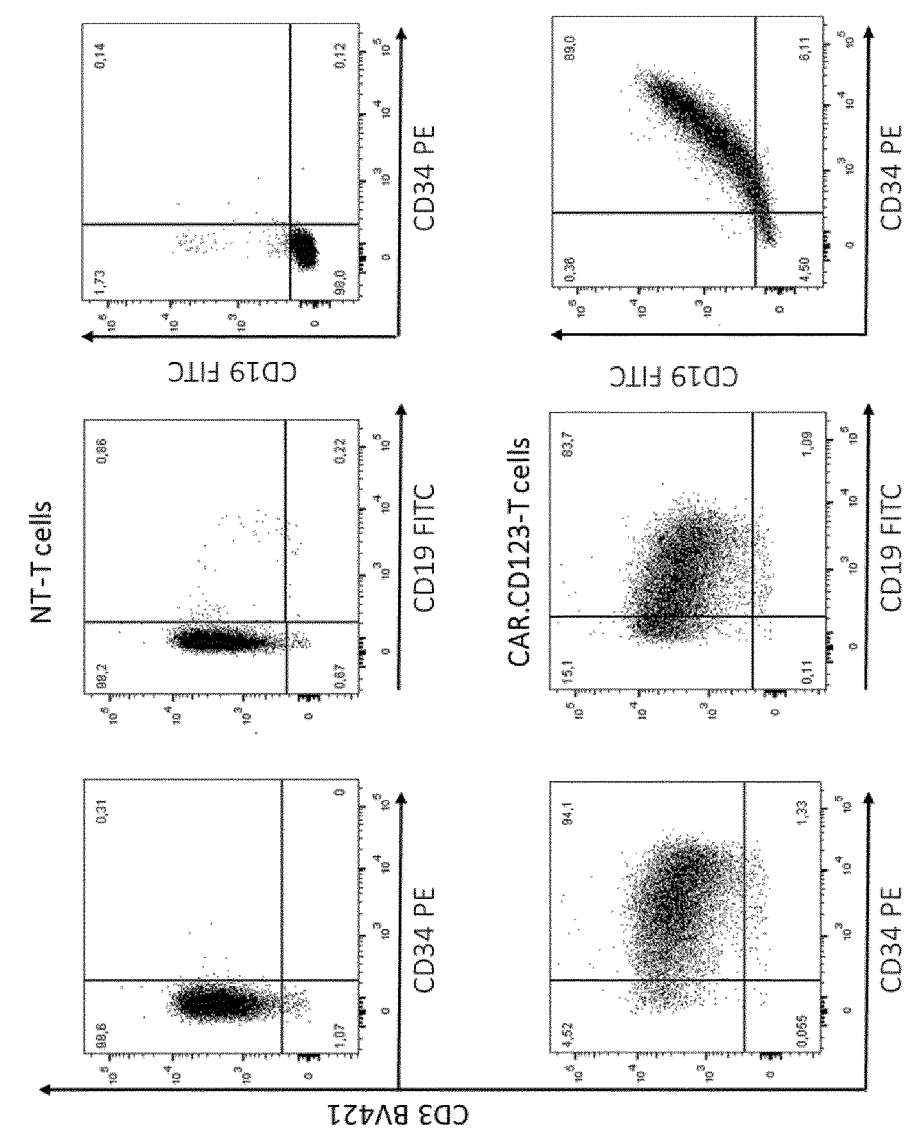
Figure 2:
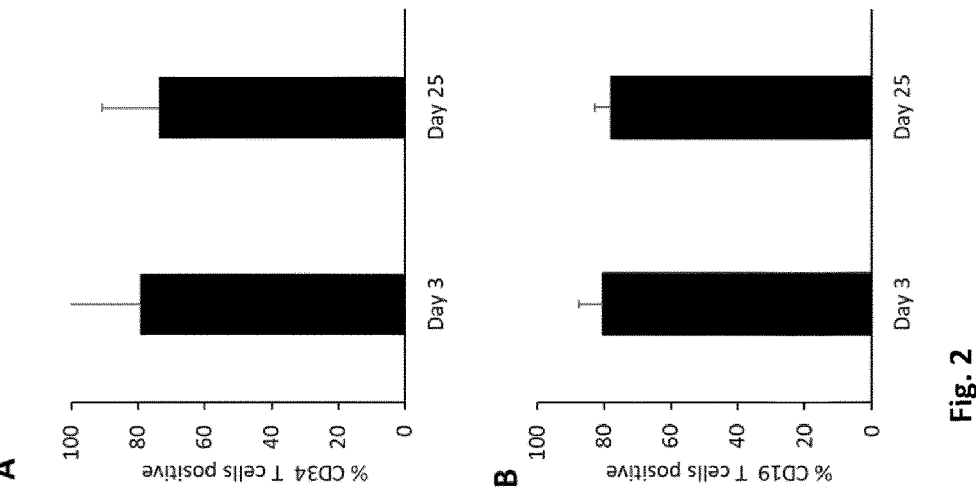

FIG. 2. ΔCD19-2A-CAR.CD123-ΔCD34-CD8.4.1BB-ζ stable expression on T cells. (A-B) A stable expression of CAR.CD123 on T cells was observed by flow cytometry analysis of ΔCD34 (A) or ΔCD19 expression (B) on T cells genetically modified with CAR.CD123, after long expansion in vitro culture (up to 25 days). The histograms (A-B) represent the average±standard deviation (SD) from 8 HDs for which CAR expression was monitored over time (at day+3 and day+25). (C) CAR.CD123 is efficiently expressed after retroviral transduction in T cells. Plots of a representative donor non transduced (NT) T cells (C, upper panel) and after transduction (C, lower panel) are shown. CAR expression was assessed by the use of anti-CD34 (PE) and CD19 (FITC) mAbs in combination with anti-CD3 (BV421).

Figure 3:
Figure 3:
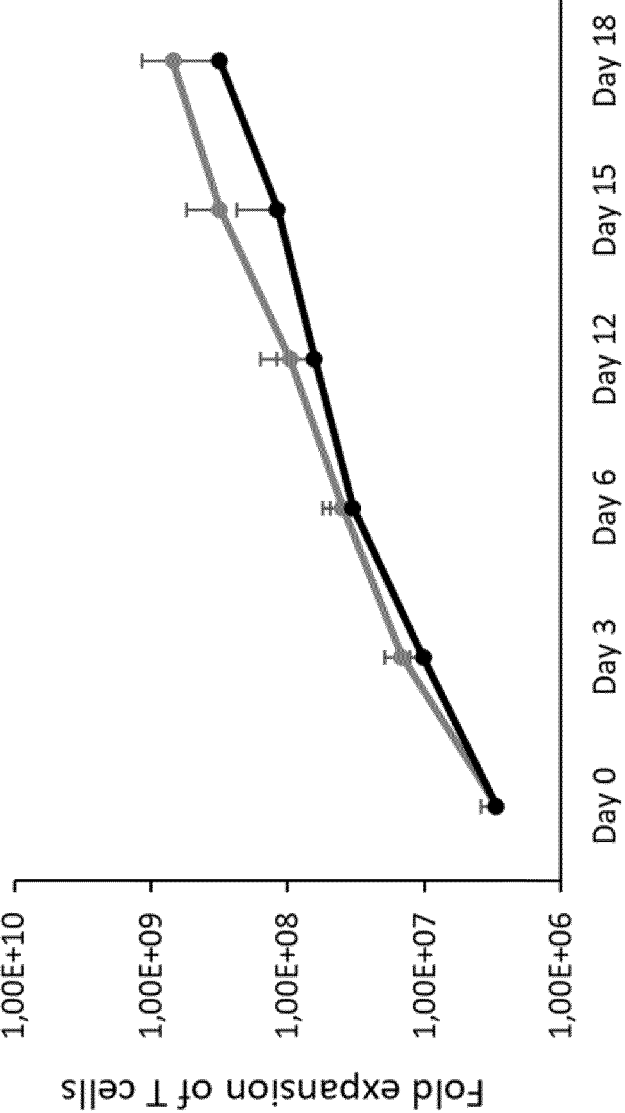

FIG. 3: T cells fold expansion overtime. T cells untransduced (NT-T) or genetically modified with ΔCD19-2A-CAR.CD123-ΔCD34-CD8.4.1BB-ζ (CAR. CD123-T) were counted on a weekly base to monitor cell expansion. Each dot is the average number of T cells from three donors ±SD.

Figure 4:
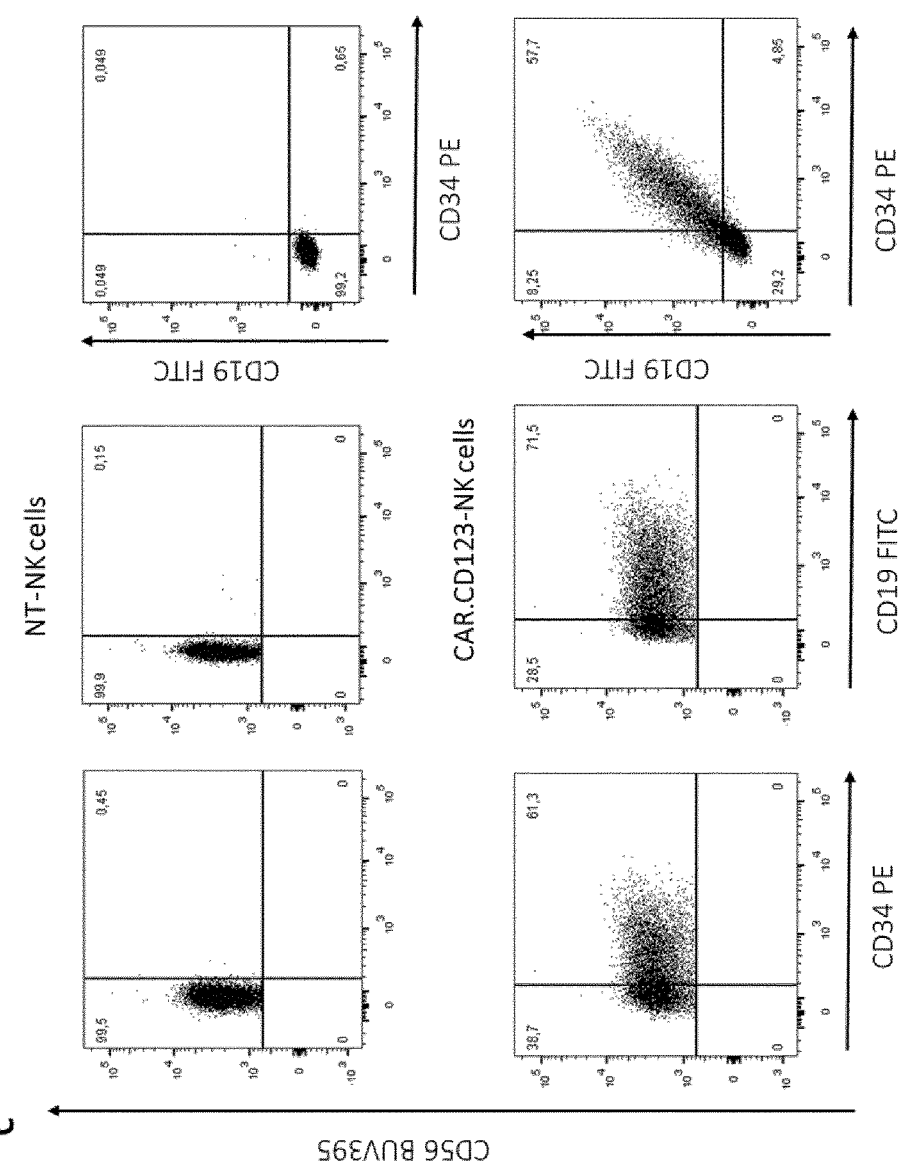
Figure 4:
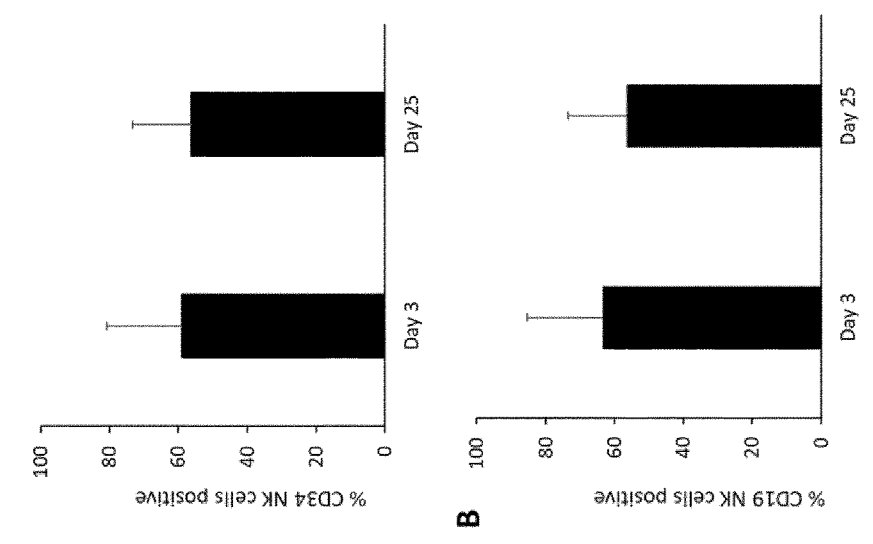

FIG. 4: ΔCD19-2A-CAR.CD123-ΔCD34-CD8.4.1BB-ζ stable expression on NK cells. (A-B) Flow cytometry analysis of ΔCD34 (A) or ΔCD19 (B) expression on genetically modified NK cells with CAR.CD123 after long expansion in vitro culture (up to 25 days). The histograms represent the average from 8 HDs+SD for which CAR expression was monitored. (C) CAR.CD123 is efficiently expressed after retroviral transduction in NK cells. Plots of a representative donor non transduced (NT) NK cells (C, upper panel) and after transduction (C, lower panel) are shown. CAR expression was assessed by the use of anti-CD34 (PE) and CD19 (FITC) mAbs in combination with anti-CD56 (BUV395).

Figure 5:
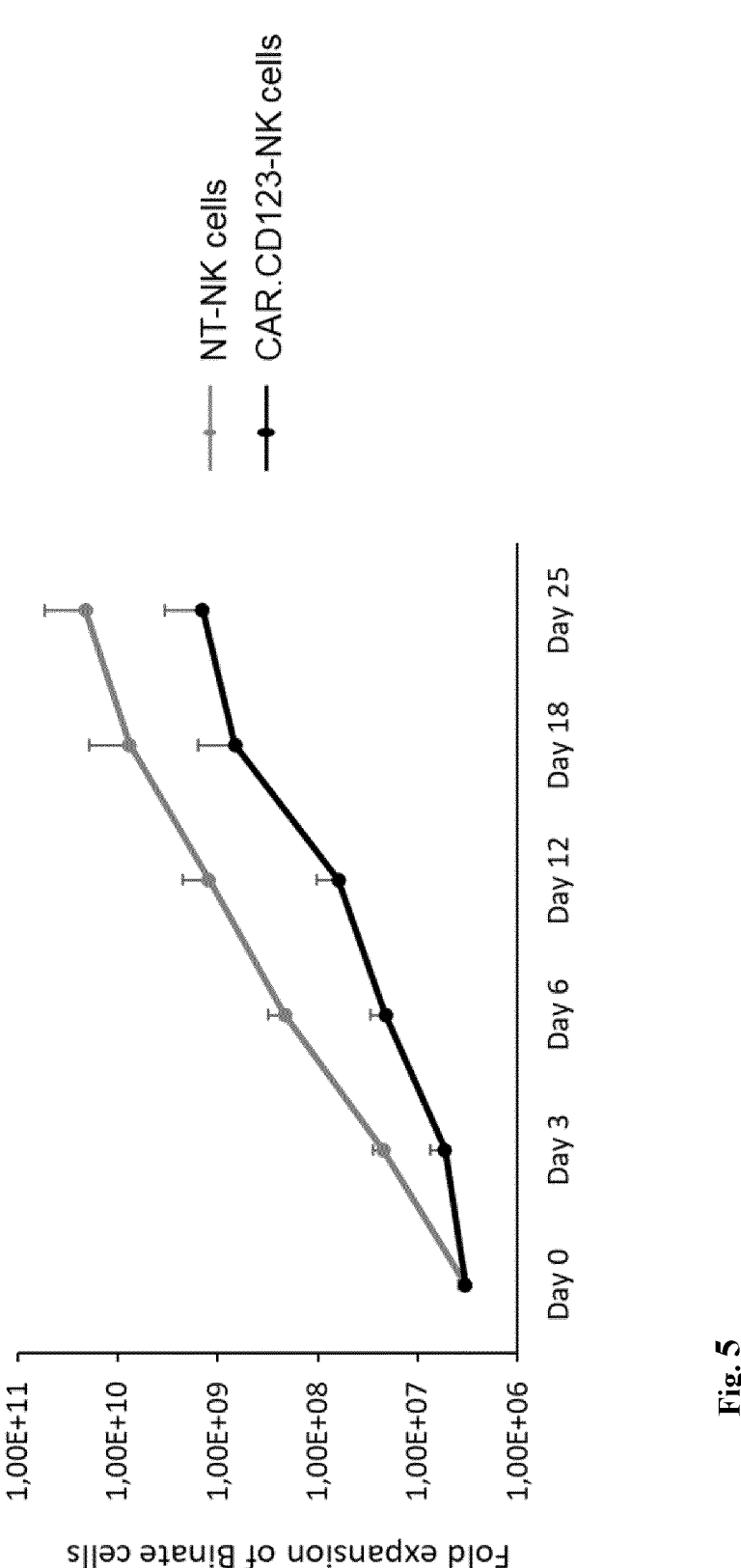

FIG. 5: Innate cells fold expansion overtime. Innate Cells un-transduced (NT-Innate Cells) or genetically modified with ΔCD19-2A-CAR. CD123-ΔCD34-CD 8.4.1BB-ζ

(CAR. CD123-Innate Cells) were counted on a weekly base to monitor cell expansion. Each dot is the average number of Innate Cells from three donors ±SD.

FIG. 6: ΔCD19-2A-CAR.CD123-ΔCD34-CD8.4.1BB-ζ stable expression on γδ T cells. Flow cytometry analysis of ΔCD34 or ΔCD19 expression on genetically modified γζ T cells with CAR.CD123. First panel show that the representative sample is represented by pure population of γδ T cells in the absence of αβ T cells. The immunophenotypic analysis was conducted by the use of anti-TCR αβ (FITC) and anti-TCR-γδ PE.CAR.CD123 is efficiently expressed after retroviral transduction in γδ T cells. Plots of a representative donor non transduced (NT) γδ T cells (upper panels) and after transduction (lower panels) are shown. CAR expression was assessed by the use of anti-CD34 (PE) and CD19 (FITC) mAbs in combination with anti-CD3 (APC).

Figure 7:
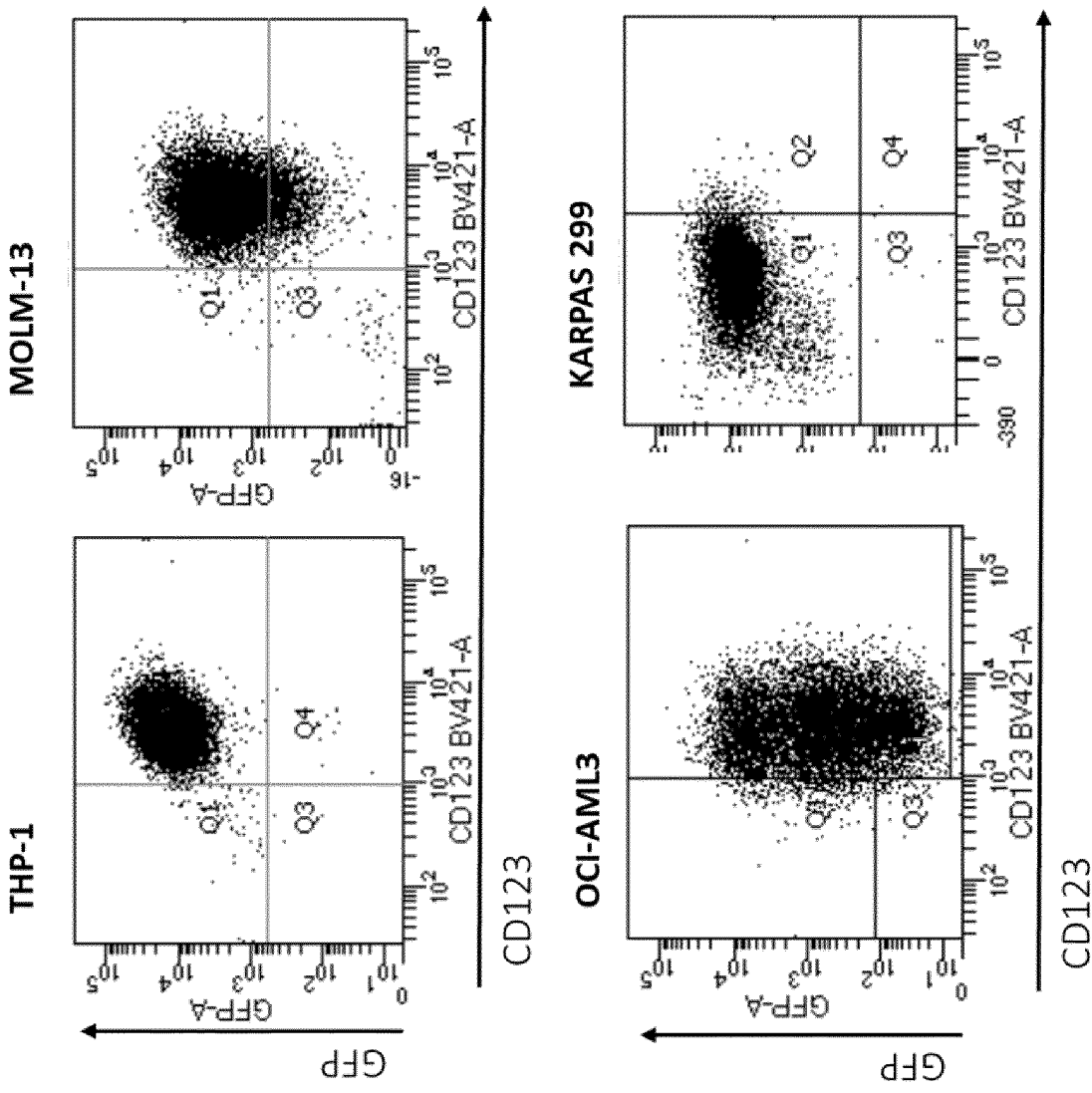

FIG. 7: Long-term anti-tumor activity of CAR.CD123-T cells. Three CD123+ cell lines (THP1, MOLM13, OCI AML3) and CD123-cells (KARPAS 299) have been co-cultured with un-transduced T cells (NT-T) or T cells genetically modified with ΔCD19-2A-CAR.CD123-ΔCD34-CD8.4.1BB-ζ (CAR.CD123-T). The histogram shows the % of remaining tumor cells after 5 days-coculture at the ratio 1:1 with either NT-T (light gray) or CAR.CD123-T cells (black bar). The experiment was performed in triplicate with T cells coming from three donors. The results are expressed as average of the biological replicates±SD. p-value≤0.01; *p-value≤0.001; ns=not significant.

Figure 8:
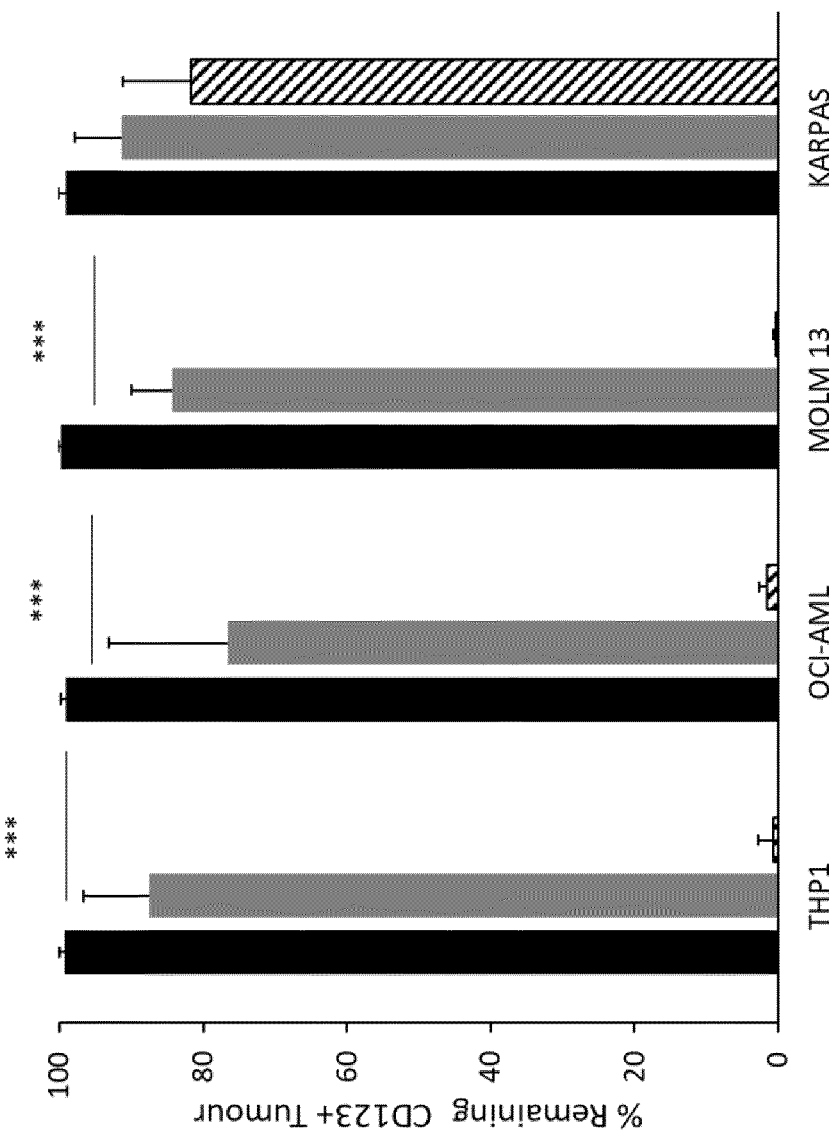

FIG. 8: Long-term anti-tumor activity of ΔCD19-2A-CAR.CD123-ΔCD34-CD8.4.1BB-ζ T cells. Three CD123+ cell lines (THP1, MOLM13, OCI AML3) and CD123-cells (KARPAS 299) have been co-cultured with un-transduced T cells (NT-T) or T cells genetically modified with ΔCD19-2A-CAR. CD123-ΔCD34-CD 8.4.1BB-ζ (CAR. CD123-T) from the same donors (n=8). The antitumor activity was evaluated using 6-days long-term co-culture assay. NT-T (light gray bar) and CAR.CD123-T (black bar), were co-incubated at the effector:target (E:T) ratio of 1:1. The histogram shows the % of remaining tumor cells after 6 days-coculture at the ratio 1:1 with either NT-T or CAR.CD123-T cells. Data from 8 donors are expressed as average±SD. p-value≤0.01; *p-value≤0.001; ns=not significant.

Figure 9:
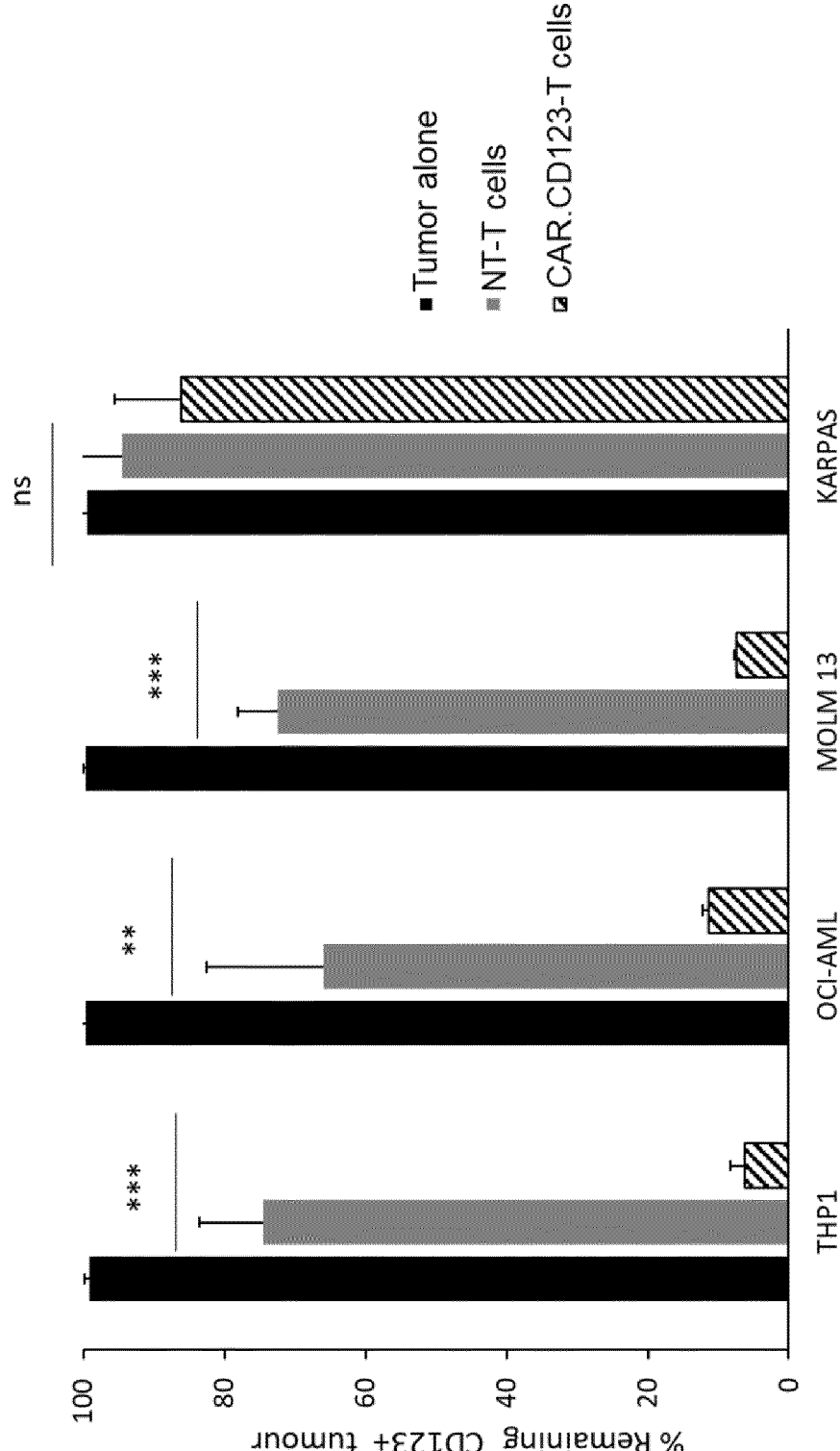

FIG. 9: Long-term anti-tumor activity of ΔCD19-2A-CAR.CD123-ΔCD34-CD8.4.1BB-ζ γδ NK cells. Three CD123+ cell lines (THP1, MOLM3, OCI AML3) and CD123-cells (KARPAS 299) have been co-cultured with un-transduced NK cells (NT-NK) or genetically modified NK (CAR.CD123-NK). The histograms show the % of remaining tumor cells after 6 days-coculture at the ratio 1:1 with either NT-NK (light gray) or CAR.CD123-NK (black bar). Data from 8 donors are expressed as average ±SD. p-value≤0.01; *p-value≤0.001; ns=not significant.

Figure 10:
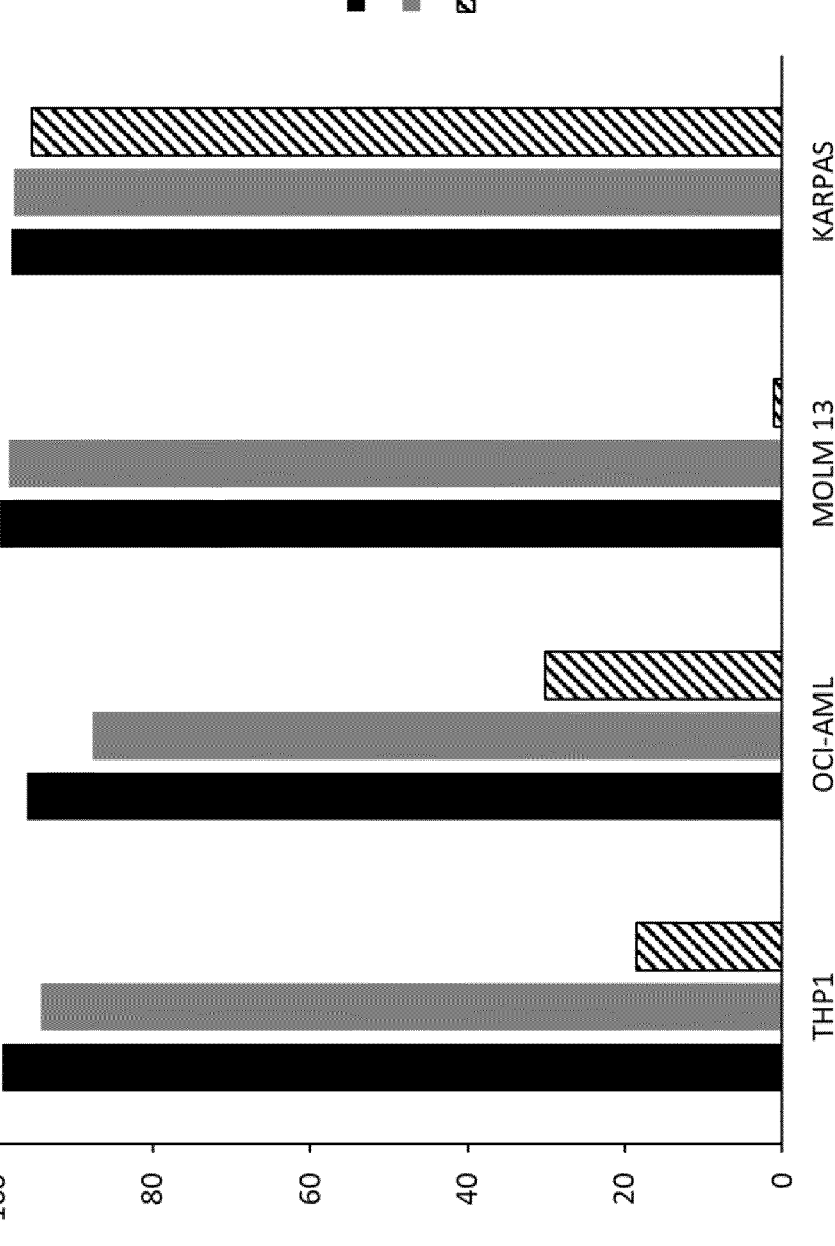

FIG. 10: Long-term anti-tumor activity of ΔCD19-2A-CAR.CD123-ΔCD34-CD8.4.1BB-ζ γδ cells. Three CD123+ tumor cell lines (THP1, MOLM3, OCI AML3) and CD123-cells (KARPAS 299) were co-cultured for 6 days with un-modified (NT-γδ) or γδ T cells genetically modified with ΔCD19-2A-CAR. CD123-ΔCD34-CD 8.4.1BB-ζ (CAR. CD123-γδ) at the E:T ratio 1:1. The histogram of a single donor shows the % of residual tumor cells (either CD123+ or CD123-) after 6 days of coculture with either NT-γδ (light gray) or CAR.CD123-γδ (black bar).

Figure 11:
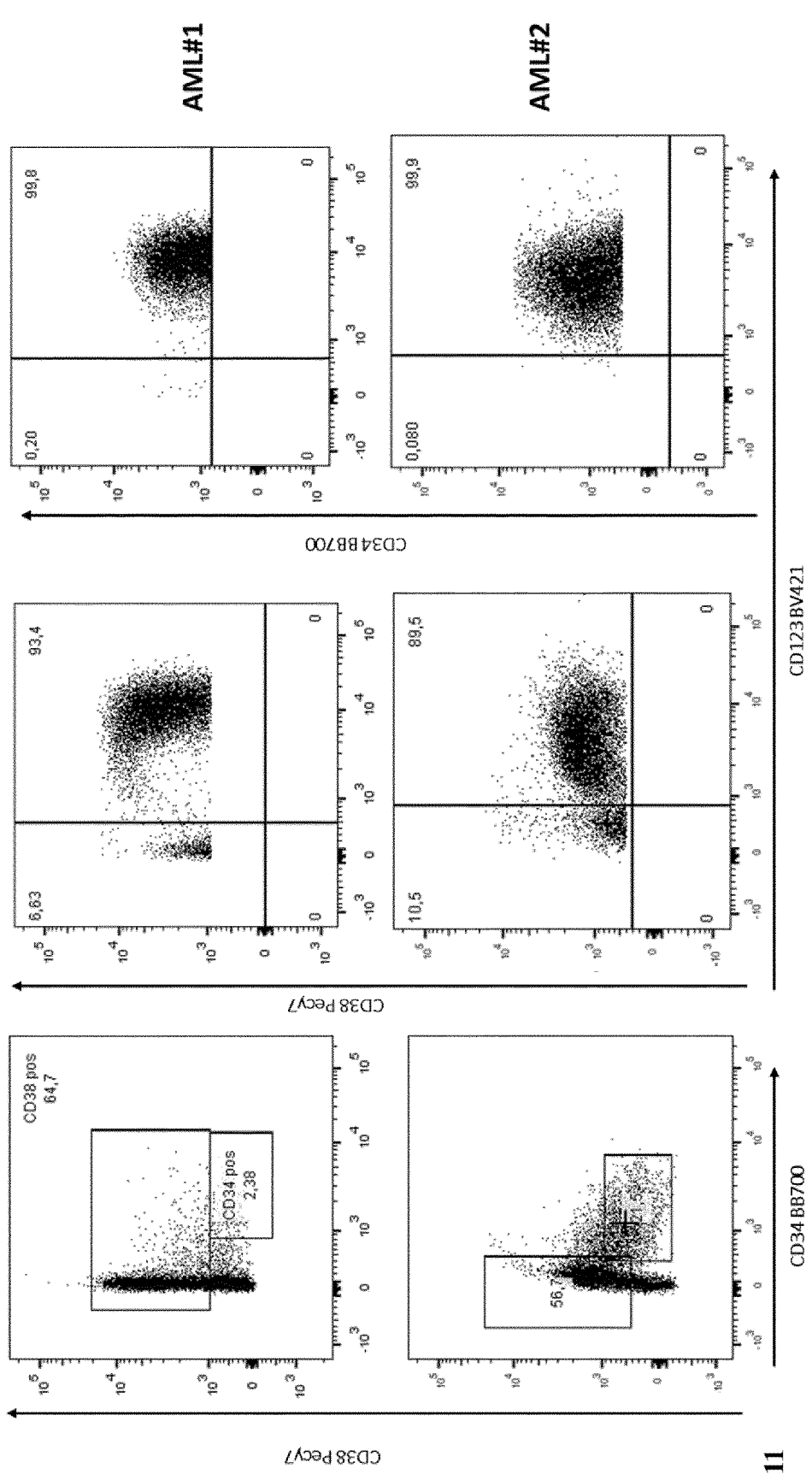

FIG. 11. Flow-cytometry analysis of CD123 expression on Bone marrow cells of Acute myeloid Leukaemia patients. The plots show the surface expression of CD123 on primary human Bone Marrow (BM) Acute myeloid Leukaemia (AML) patients at diagnosis (AML#1, AML#2). To perform flow cytometry analysis of CD123 expression anti-CD123 (BV421), CD34 (BB770) and CD38 (PeCy7) were used.

Figure 12:
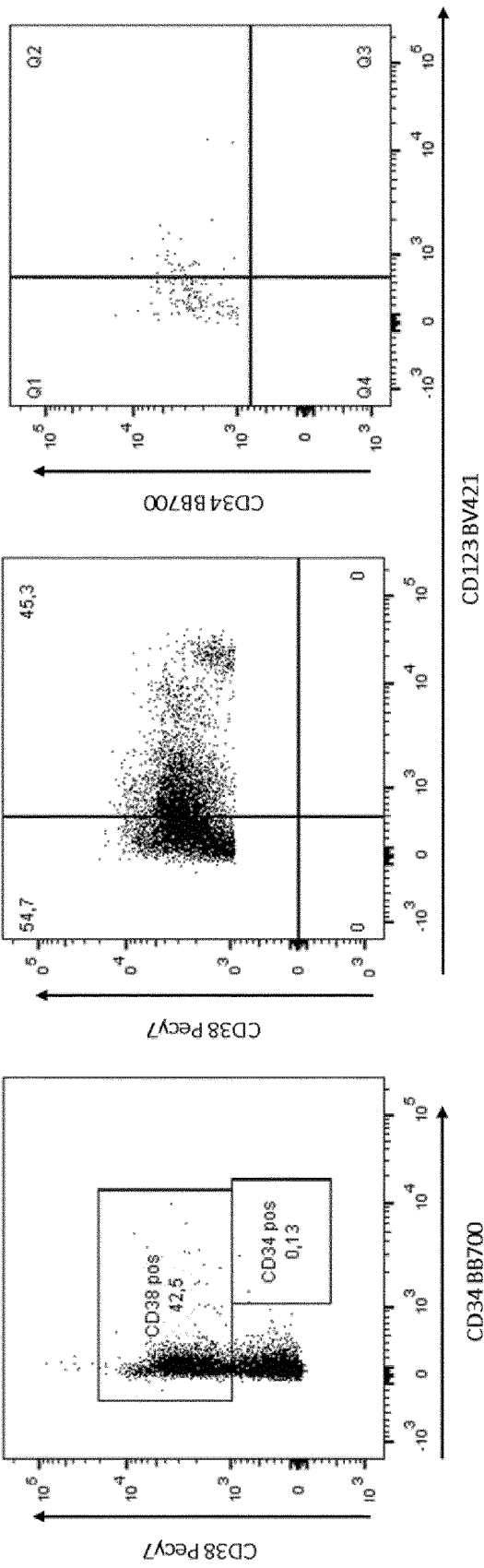

FIG. 12 Flow-cytometry analysis of CD123 expression on Bone marrow cells of Healthy Donor. The plots show the surface low/negligible expression of CD123 on primary human Bone Marrow (BM) Healthy donor (HD) sample. To perform flow cytometry analysis of CD123 expression anti-CD123 (BV421), CD34 (BB770) and CD38 (PeCy7) were used.

Figure 13:
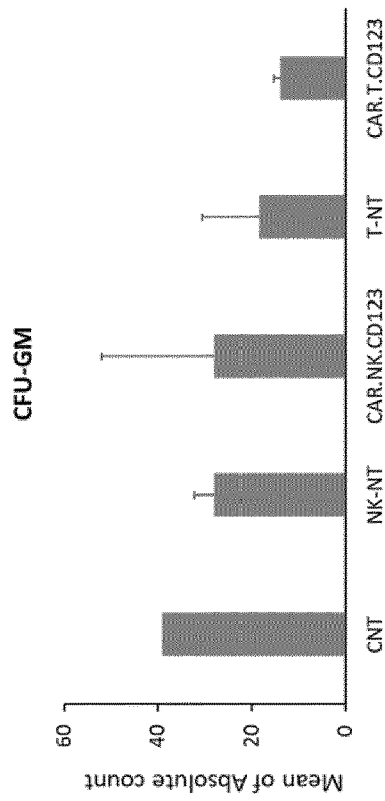
Figure 13:
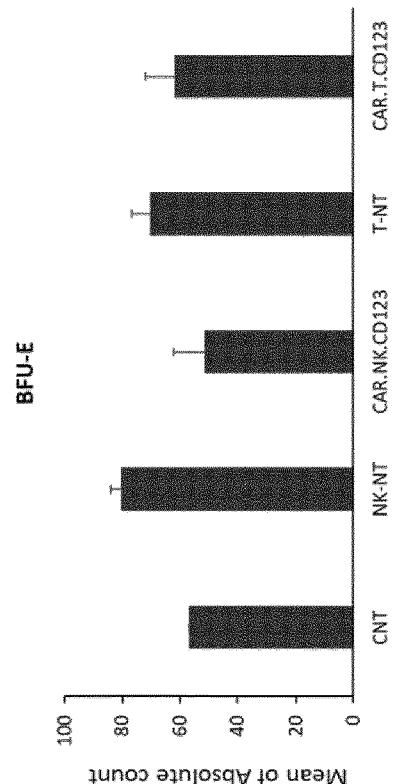

FIG. 13. Negligible off-tumour on-target effect of ΔCD19-2A-CAR.CD123-ΔCD34-CD8.4.1BB-ζ cells. The histograms show the comparison of the number of Colony Forming Unit (CFUs) in different experimental groups. Purified CD34+ cells from BM of an Healthy Donor (HD) were co-cultured at the effector:target ratio 1:1 with either un-modified T and NK (NT-T, NT-NK) cells and modified T and NK cells (CAR.CD123-T, CAR.CD123-NK) for 4 hours. Co-cultured assays were plated in biological triplicate and hematopoietic colonies were scored after 14 days. (A) Score of absolute counting of BFU-E; (B) Score of absolute counting of GM-CFU. Data from 2 donors are expressed as average ±SD.

Figure 14:
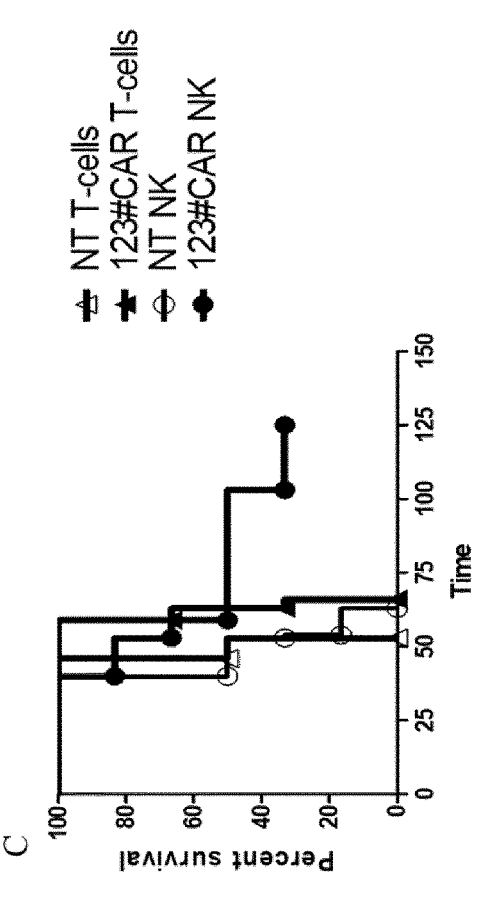
Figure 14:
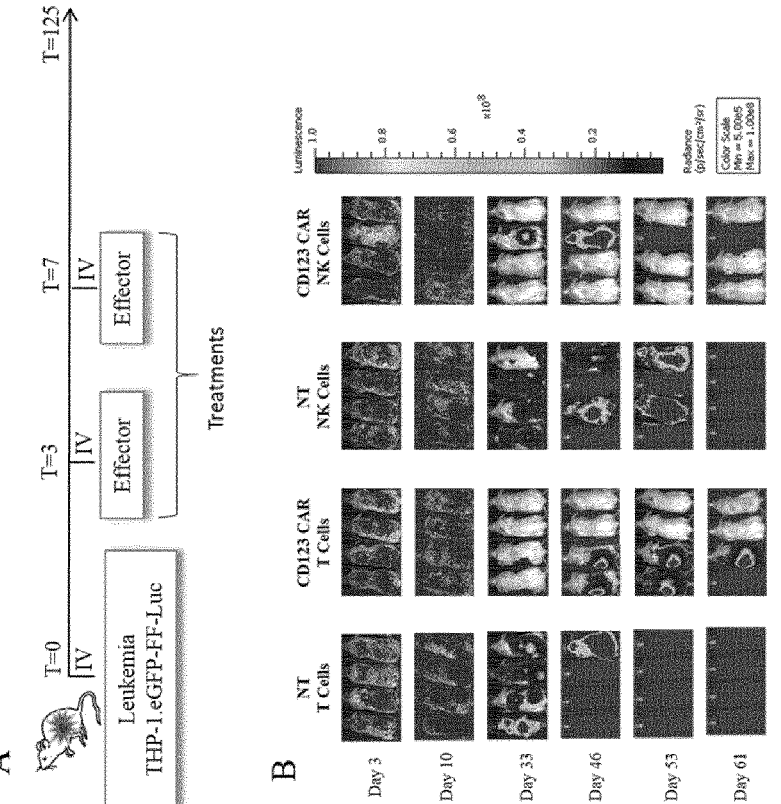

FIG. 14. In vivo model of ΔCD19-2A-CAR.CD123-ΔCD34-CD8.4.1BB-ζ cells showing activity in both T and NK cells. (A) The cartoon shows xenograft immunodeficient mouse model systemically infused with THP-1-FF-Luc.GFP cells (0.01×10⁶ cell/mouse). At the time of tumor establishment (Day3), mice were infused i.v. (Day +3 and Day+7). (B) Time course of in vivo bioluminescence imaging of the treated NSG mice from day 3 to day 61. (C) 80-day probability of overall survival (OS) of leukemia bearing mice treated with two consecutive adoptive transfer of NT-T (red line; 4 mice), CAR.CD1213-T (black line; 4 mice), NT-NK (green line; 4 mice) and CAR.CD123-NK (blue line; 4 mice) cells. (D) Statistical analysis of 80 days overall survival of leukemia bearing mice treated with two consecutive adoptive transfer of NT-T, CAR.CD123-T, NT-NK and CAR.CD1123-NK cells.

Figure 15:
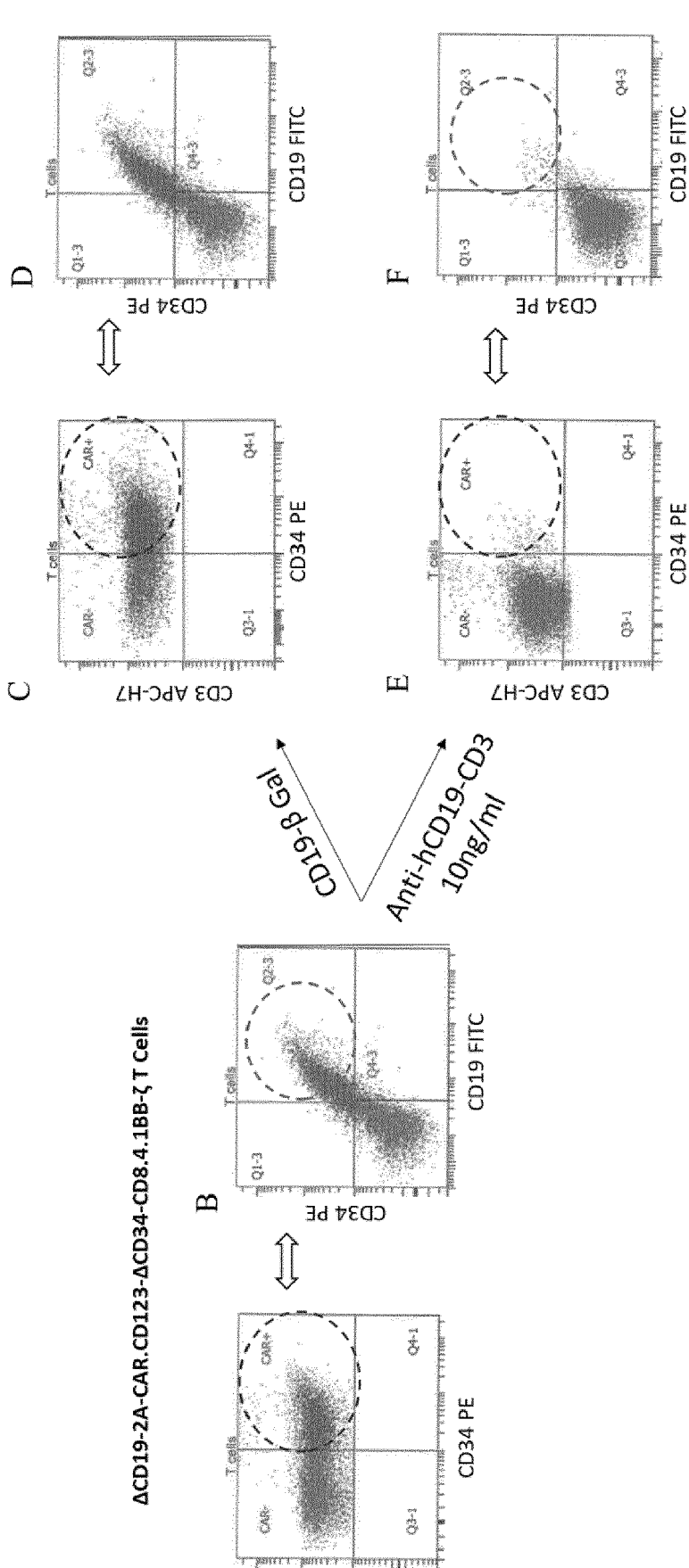

FIG. 15. In vitro model of CD19 suicide gene activity in ΔCD19-2A-CAR.CD123-ΔCD34-CD8.4.1BB-ζ T cells. Flow-cytometry analysis of ΔCD19-2A-CAR.CD123-ΔCD34-CD8.4.1BB-ζ T cells upon CD19 selective engagement with anti-hCD19-CD3 bite antibody. T cells from an exemplificative donor were genetically modified with ΔCD19-2A-CAR.CD123-ΔCD34-CD8.4.1BB-ζ. (A-B) ΔCD19-2A-CAR.CD123-ΔCD34-CD8.4.1BB-ζ T cells were characterized for the CAR expression by Ab CD34-PE (A) and Ab CD19-FITC (B). ΔCD19-2A-CAR.CD123-ΔCD34-CD8.4.1BB-ζ T cells were exposed to one dose of 10 ng/ml of negative control, namely Ab CD19-13 Gal bite or one dose of 10 ng/ml anti-hCD19-CD3 bite for 24 hours. (C-D) ΔCD19-2A-CAR.CD123-ΔCD34-CD8.4.1BB-ζ T cells were not affected by negative control, namely Ab CD19-β Gal bite engagement, as demonstrated by the flow-cytometric analysis of CD34 (C) and CD19 (D). (E-F) ΔCD19-2A-CAR.CD123-ΔCD34-CD8.4.1BB-ζ T cells were selectively eliminated by anti-hCD19-CD3 bite engagement at the first evaluated time point of 24 hours, as demonstrated by the flow-cytometric analysis of CD34 (E) and CD19 (F).

Figure 16:
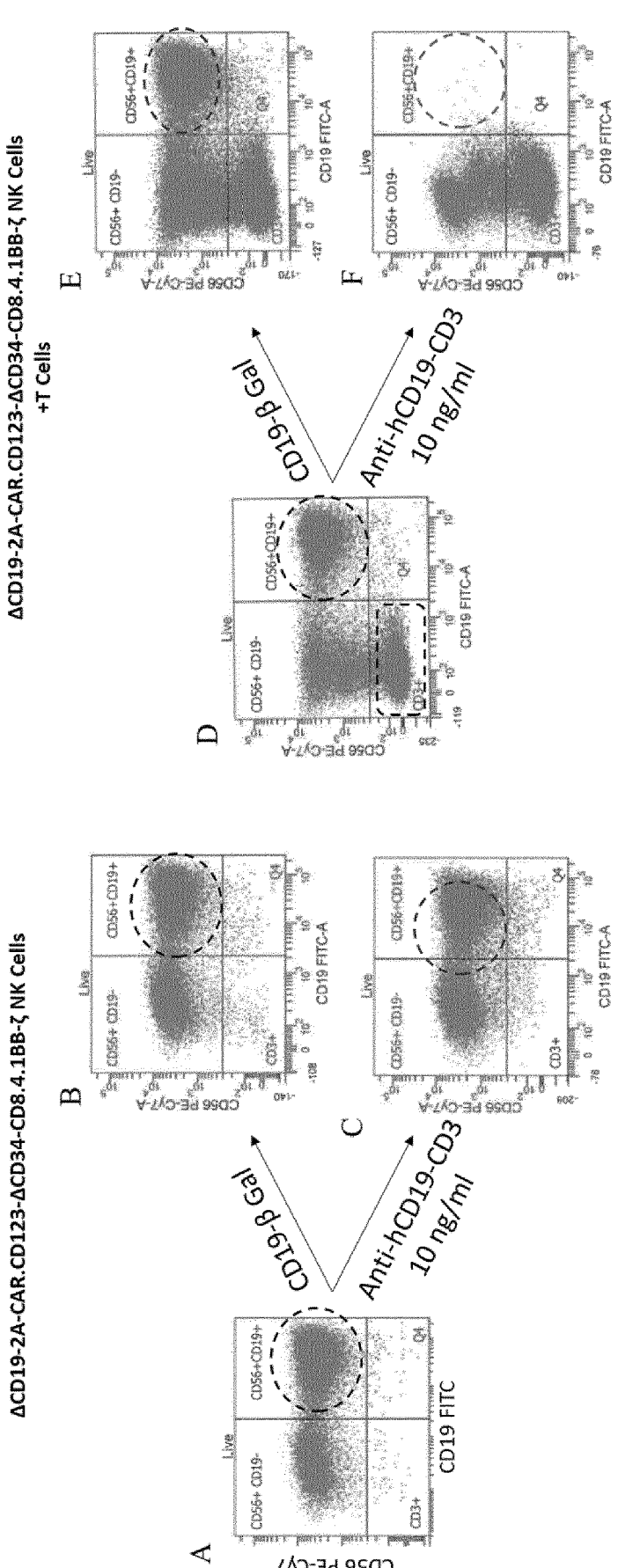

FIG. 16. In vitro model of CD19 suicide gene activity in ΔCD19-2A-CAR.CD123-ΔCD34-CD8.4.1BB-ζ NK cells. Flow-cytometry analysis of ΔCD19-2A-CAR.CD123-ΔCD34-CD8.4.1BB-ζ NK cells upon CD19 selective engagement with anti-hCD19-CD3 bite antibody in the presence of CD3+ T cells. (A-C) NK cells from an exemplificative donor were genetically modified with ΔCD19-2A-CAR CD123-ΔCD34-CD8.4.1BB-ζ. ΔCD19-2A-CAR CD123-ΔCD34-CD8.4.1BB-ζ NK cells were characterized for the CAR expression by Ab CD56 PE-Cy7 and Ab CD19-FITC (A). ΔCD19-2A-CAR.CD123-ΔCD34-CD8.4.1BB-ζ NK cells were exposed for 24 hours to one dose of 10 ng/ml of negative control, namely Ab CD19-0 Gal bite (B) or one dose of 10 ng/ml anti-hCD19-CD3 bite (C) in the absence of CD3+ T cells (control negative experimental condition). (D-F) NK cells from an exemplificative donor were genetically modified with ΔCD19-2A-CAR.CD123-ΔCD34-CD8.4.1BB-ζ. ΔCD19-2A-CAR CD123-ΔCD34-CD8.4.1BB-ζ NK cells were characterized for the CAR expression by Ab CD56 PE-Cy7 and Ab CD19-FITC (D). ΔCD19-2A-CAR.CD123-ΔCD34-CD8.4.1BB-ζ NK cells were exposed for 24 hours to one dose of 10 ng/ml of negative control, namely Ab CD19-β Gal bite (E) or one dose of 10 ng/ml anti-hCD19-CD3 bite (F) in the presence of CD3+ T cells. ΔCD19-2A-CAR.CD123-ΔCD34-CD8.4.1BB-ζ NK cells were selectively eliminated by anti-hCD19-CD3 bite engagement in the presence of CD3+ T cells.

FIG. 17. In vivo model of CD19 suicide gene activity in ΔCD19-2A-CAR.CD123-ΔCD34-CD8.4.1BB-ζ T cells. (A) The cartoon shows xenograft immunodeficient mouse model systemically infused with ΔCD19-2A-CAR.CD123-ΔCD34-CD8.4.1BB-ζ T cells (CAR.CD123-T cells; dose: 10×10$^6$/mouse). Effector cells were infused i.v. on Day0 (I dose), Day4 (II dose) and Day8 (III dose) in concomitance to the administration of subcutaneous administration of IL2 (twice a week; 1000 U/mouse). 30 days after the first dose, when T-cells show a significant in vivo expansion, NSG mice were treated for 5 consecutive days with Anti-hCD19-CD3 bite (5 μg/mouse). (B-C) FACS analysis of ΔCD19-2A-CAR.CD123-ΔCD34-CD8.4.1BB-ζ T cells before (B) and after Anti-hCD19-CD3 bite administration (C) in one exemplificative blood bleeding of NSG mouse. CD19 expression analysis shows CAR+ Cells (CD3+CD19+) before (B) and after Anti-hCD19-CD3 bite administration (C).

MATERIAL AND METHODS

Design of CAR-CD123 Plasmid (Constructs)

A clinical grade "second" generation of retrovirus bicistronic vector SFG have been designed, allowing the simultaneous expression of two transgenes, namely ΔCD19 and the cassette anti-CD123 single-chain variable fragment (scFv), derived from a murine antibody of IgG (7G3) class, linked via a codon optimized human CD8 spacer-transmembrane domain, to the codon optimized signaling costimulatory domain 4-1BB (CD137) and CD3-ζ (FIG. 1).

In particular a ΔCD19 represents the extracellular domain of human CD19 linked to the transmembrane portion. The single chain variable fragment (scFv)—specific for CD123—is a fusion protein of 114 amino acid (aa) of the variable regions of the light chains (VL) of immunoglobulins connected by flex (a short linker peptide) of 8 amino acids to 118 aa of heavy chains (VH) of immunoglobulins.

In particular, the scFv 7G3 is cloned in frame with codon optimized CD34 derived epitope of 16 aa (as trackable marker), linked by spacer of 42 aa (11 aa as spacer plus 31 aa of codon optimized CD8 extracellular domain) to bind the codon optimized human CD8-transmembrane domain (CD8aTM) of 21aa. The signal run from extracellular portion of CD123 scFv 7G3 to intracellular portion of CD3-ζ chain (113aa) through costimulatory molecule: 4-1BB endodomain (42aa) for the SFG: ΔCD19-2A-CAR.CD123-ΔCD34-CD8.4.1BB-ζ (CAR.CD123-T) retroviral vector.
Generation of eGFP-Firefly-Luciferase cell lines.

The retroviral vector encoding eGFP-Firefly-Luciferase (eGFP-FFLuc) was used in selected experiments to label CD123 positive (CD123$^+$) or CD123 negative (CD123$^-$) tumor cells:

CD123$^+$:

Acute Monocytic Leukemia cell line THP-1

Acute Myeloid Leukemia cell line MOLM-13

Acute Myeloid Leukemia cell line OCI-AML-3

CD123$^-$:

Non-Hodgkin's Lymphoma (NHL) Karpas 299

Cell Lines.

Acute Monocytic Leukemia cell line THP-1 cell was obtained from LGC Standards-ATCC. Acute Myeloid Leukemia cell line MOLM-13 and OCI-AML-3 were obtained from DSMZ. Non-Hodgkin's Lymphoma (NHL) Karpas 299 was obtained from Sigma-Aldrich.

The THP-1, MOLM-13 and the Karpas 299 cell lines were maintained in culture with RPMI 1640 medium. The OCI-AML-3 were maintained in culture with IMDM. Cell lines were supplemented with 10% fetal bovine serum (FBS, Hyclone, Thermo Scientific, Pittsburgh, PA) and 2 mM GlutaMax (Invitrogen, California, USA). Cells were maintained a humidified atmosphere containing 5% CO2 at 37° C. All cell lines were routinely tested for mycoplasma and for surface expression of target antigen CD123. All cell lines have been authenticated by STR analysis in the certificated lab "BMR Genomics s.r.l."

Retroviral Supernatant

Transient retroviral supernatant was produced by cotransfection of 293T with the MoMLV gag/pol expression plasmid PeqPam3(-env), the RD114 env expression plasmid RDF, and SFG vectors at a ratio of 2:3:3, respectively, with a total of 10 μg DNA. The transfection was facilitated with GeneJuice reagent (Calbiochem). The supernatant was harvested 2 and 3 days after transfection, filtered (using a 0.45-mm filter), snap-frozen, and stored at −80° C. in 5-ml aliquots [27].

Isolation, Generation and Transduction of Effector Cells.

Peripheral blood mononuclear cells (PBMC) were isolated from peripheral blood (PB) or buffy coat obtained from healthy donors (OPBG Hospital, Rome, Italy) after that signed informed consent was obtained, in accordance with rules set by Institutional Review Board (IRB) of OPBG (Approval of Ethical Committee N° 969/2015 prot. N° 669LB), using Lymphocytes separation medium (Eurobio; France). T lymphocytes were activated with immobilized OKT3 (1 μg/ml, e-Bioscience Inc.; San Diego, CA, USA) and anti-CD28 (1 μg/ml, BD Biosciences, Europe) antibodies in the presence of combination of recombinant human interleukin-7 (IL7, 10 ng/ml; R&D; USA) [28] and recombinant human interleukin-15 (IL15, 5 ng/ml; R&D) [29] [30]. Activated T cells were transduced on day 3 in 24-well plates pre-coated with recombinant human RetroNectin (Takara-Bio. Inc; Japan) using a specific retroviral supernatant and the specific above-described cytokines. At day 5 from transduction the T cells are expanded in "CTL complete medium" containing 45% RPMI1640 and 45% Click's medium (Sigma-Aldrich,Co.; Usa) supplemented with 10% FBS and 2 mM Glutamax, and fed twice a week with the specific above described cytokines [31].

Isolation, Generation and Transduction of NK or γδ-T Cells.

Peripheral blood mononuclear cells (PBMC) were isolated from healthy donor's buffy coat or leukapheresis by a density-gradient technique (Ficool-Histopaque (Eurobio; France); the healthy donors had signed a written informed consent, in accordance with rules set by the Institutional Review Board of OPBG (Approval of Ethical Committee N_969/201515 prot. N_669LB). CD56+ CD3– NK cells, isolated with an NK isolation Kit (Miltenyi Biotec, Inc., San Diego, CA, USA), and expanded with NK Cell Activation/Expansion Kit (Miltenyi Biotec, Inc., San Diego, CA, USA) and recombinant human interleukin 2 (IL2, 500 U/ml; R&D; USA) or recombinant interleukin 15 (IL15 10 U/ml; R&D; USA). Activated NK cells were transduced in 24-well plates pre-coated with recombinant human RetroNectin (Takara-Bio. Inc; Japan) using retroviral supernatant. Enriched NK cells were cultured in GMP-compliant media (NK MACS Miltenyi Biotec, Inc., San Diego, CA, USA).

γδ-T cells were obtained from αβ and CD19 depleted donors after cryopreservation in CryoStor® cell cryopreservation media (Sigma-Aldrich) and expanded in NK MACS media after activation with Activation/Expansion Kit (Miltenyi Biotec, Inc., San Diego, CA, USA) as described above.

Patients Details

For in vitro studies, primary BM samples were collected at diagnosis from 2 pediatric patients with Acute Myeloid Leukemia (AML). Moreover, a BM sample was collected from one HD donor (OPBG Hospital, Rome, Italy). The signed informed consent was obtained in accordance with rules set by Institutional Review Board (IRB) of OPBG (Approval of Ethical Committee N° 969/2015 prot. N° 669LB)

Phenotypic Analysis

The following mAbs were used: CD3, CD123, CD45, CD56, CD34, CD19, (All from BD Pharmigen, USA). The expression of CAR.CD123 on T cells was evaluated using anti-CD34 Ab (R&D, USA) or the Pierce Recombinant Biotinylated Protein L [32] (Thermo Fisher Scientific, USA). Samples were analyzed with a BD LSRFortessa X-20 and Diva software (BD Biosciences). For each sample, a minimum of 20,000 events have been analyzed.

Fold Expansion

Cells were count one time for week by Counting Chambers using a trypan blue method.

In Vitro Anti-Leukemia Activity

For co-culture experiments, effector T lymphocytes and leukemia cell lines were plated in 24-well plates. Following 5 days of incubation at 37° C., tumor cells and T cells were collected and analyzed by FACS.

Positive Selection of Bone Marrow CD34+ Cells

CD34+ cells were isolated from healthy donors bone marrow samples. First, the CD34+ cells were magnetically labelled with CD34 MicroBeads (Miltenyi Biotec, Inc., San Diego, CA, USA). A flow cytometry analysis was conducted whit anti-CD34 (PE) to evaluate the purity of CD34 positive fraction (CD34+).

Colony-Forming Unit (CFU) Assay

CD34+ were co-cultured either un-modified T and NK cells and T or NK cells genetically modified with ΔCD19-2A-CAR.CD123-ΔCD34-CD8.4.1BB-ζ at the E:T ratio 1:1. After 4 hours of incubation CD34+ were seeded in the MethoCult GF H4434 medium. The cells were seeded at a 500 cells/dish density following the manufacturer's instructions for the CFU assay. Each cell co-cultured group was plated in 3 replicate wells and cultures were maintained at 37° C. in a humidified atmosphere with 5% $CO_2$ and 20% $O_2$. Following 14 days culture, the number and type of CFUs were determined.

Induction of Apoptosis of CAR-123 Cells

Bispecific antibody against human CD19 and human CD3 (Anti-hCD19-CD3 [Aurogene , catalog number: BIMAB-HCD19CD3) was added at the indicated concentrations to the NT or CAR.CD123 T cells and in co-culture condition with un-modified T cells and CAR.CD123-NK cells. The elimination of genetically modified CAR+ cells were evaluated at 72 hours by FACS analysis of viable cells.

Xenogenic In Vivo Leukemia Models

NOD/SCID IL-2Rγnull (NSG) xenograft mice were infused with THP-1 cells to assess in vivo the antitumor effect of CAR-transduced NK or T cells. Mouse experiment was conducted in compliance with the ethical international, EU and national requirements and were approved by the Italian Health Ministry (N° 88/2016-PR). NGS mice (5 weeks old; The Jackson Laboratory, USA) were inoculated with Firefly Luciferase-labeled THP-1 cells (THP-1 FF-Luc) $(0.01\times10^6)$. On day-3 and day 7 mice were injected with two doses of $10\times10^6$NT-NK or CAR.CD123-NK and $5\times10^6$ NT-T or CAR.CD123 T cells through i. v. injection, and subjected to weekly bioluminescence imaging (IVIS System, Perkin Elmer, USA). Signal quantitation of photons/second was performed as previously described.

In Vivo Apoptosis Induction by Bispecific Antibody Against Human CD19 and Human CD3 in CAR.CD123-T Cells The activity of bispecific antibody against human CD19 and human CD3 (Anti-hCD19-CD3) was evaluated in in vivo model on CAR.CD123 T cells. NGS mice were systemically infused (i.v.) with 3 doses of $20\times10^6$ of NT or CAR.CD123 T-cells in combination with IL-2 (1000U). After T cells expansions, mice were treated with daily of infusion anti-hCD19-CD3 for 5 consecutively days. Mice underwent periodical blood collection for FACS analysis before and after treatment and the CAR.CD123 T cells expansion was monitored by anti-human-CD19 (FITC).

Statistical Analysis

Statistical evaluation was performed using GraphPad Prism (GraphPad Software). Differences between groups generating p-values <0.05 were considered significantly. The mouse survival data were analyzed using the Kaplan-Meier survival curve and Log-rank (Mantel-Cox) test was used to measure statistically significant differences. No valuable samples were excluded from the analyses. Animals were excluded only in the event of their death after tumor implant, but before T or NK cell infusion. Neither randomization nor blinding were done during the in vivo study. However, mice were matched based on the tumor signal for control and treatment groups before infusion of control or gene modified T (NK) cells. To compare the growth of tumors over time, bioluminescence signal intensity was collected in a blind fashion. Bioluminescence signal intensity was log transformed and then compared using a two-sample t-test.

Results

The CAR.CD123-4.1BB-ζ sequence mentioned above according to the present invention provides unexpected advantages in comparison with the known CARs-CD123 (Table 2) such as: the introduction of ΔCD19 as selectable marker and inducible suicide gene (FIG. 1); furthermore, inventors show a high level of stable CAR-CD123 expression in both T cells and in Innate cells (NK cells or and gamma/delta T cells) (FIGS. 2, 4 and 6).

ΔCD19-2A-CAR.CD123-4.1BB-ζ retroviral vector did not induce any significant proliferative change in genetically modified cells as compared to control non-transduced (NT) T-cells (FIG. 3) or NK cells (FIG. 5), providing the proof of no toxicity or fratricide activity of the construct in the cellular platform of abT, NK and gdT cells.

The in vitro results herewith described show that modified polyclonal ΔCD19-2A-CAR.CD123-ζ T cells/NK cells or and gamma/delta T cells, according to the present invention were able to eliminate very efficiently CD123+ tumors (FIG. 7), in long-term co-culture for CAR-CD123 T cells (FIG. 8), NK cells (FIG. 9) and gamma/delta T cells (FIG. 10).

More in detail, the supernatants obtained by SFG retroviral vector were able to transduce efficiently activated T cells (FIG. 2), NK cells (FIG. 4) or gamma/delta T cells (FIG. 6), with very high level of transduction. Furthermore, the retroviral vector expression is stable over time in both T cells (FIG. 2A-B) or NK cells (FIG. 4A-B) without interfering with the cell expansion (FIGS. 3 and 5). The introduction in the construct of CD34 derived epitope as trackable marker let easily to track the genetically modified T cells (alpha/beta CD3+CD34+), NK cells (CD56+CD34+), in gamma/delta T cells (gamma/delta CD3+CD34+), in vitro model (FIGS. 2C, FIG. 4C and FIG. 6). In vivo model of AML xenograft mice confirmed in vitro results of CARs-CD123 potency (FIG. 14). FACS analysis confirmed that only leukemia stem cells from AML patients express high level of CD123 (FIG. 1) respect to progenitor cells derived from bone marrow of healthy donors (FIG. 12). Moreover, we confirm that the invention is characterized by high degree of specificity to targeting leukemia cells with a negligible off-tumor on-target effect of CAR-CD123 cell towards hematopoietic stem cells derived from bone marrow of healthy donors, by performing absolute counting of Colony Forming Unit (FIG. 13).

Moreover, we demonstrated the efficacy of induction of CD19 suicide gene activity for both CAR-CD123 T cells (FIG. 15) and CAR-CD123 NK cells (FIG. 16), in in vitro models. To note CAR-CD123 NK cells can be eliminated by anti-hCD19-CD3 bite treatment only in the presence of T cells (FIG. 16D-F), proving the high specificity and selectivity of the approach. The suicide gene activity was also confirmed in vivo model (FIG. 17A), as shown by FACS analysis, by analysing the circulating CAR.CD123 T cells (CD3+CD19) before and after treatment of mice with Anti-hCD19-CD3 bite administration (FIG. 17 B-C).

The present disclosure also discloses the following items:

1. A chimeric antigen receptor (CAR) molecule comprising, from the N-terminus to the C-terminus:
   a) an extracellular domain and transmembrane domain of human CD19,
   b) an antigen binding domain,
   c) a spacer domain,
   d) a transmembrane domain,
   e) a cytoplasmatic domain,
   preferably wherein the CAR is a CD123 specific CAR (CD123 CAR) and the antigen binding domain comprises VH and/or VL from a monoclonal anti-CD123 antibody, more preferably the antigen binding domain comprises a single chain variable fragment (scFv) that specifically binds to CD123.

2. The CAR molecule according to item 1 wherein the extracellular and transmembrane domains of human CD19 comprises or consist of a sequence having at least 80% of identity to SEQ ID NO: 1 (MPPPRLLF-FLLFLTPMEVRPEEPLVVKVEEGD-NAVLQCLKGTSDGPTQQLTWSRESPLKPF LKLSLGLPGLGIHMR-PLAIWLFIFNVSQQMGGFYL-CQPGPPSEKAWQPGWTVNVEGSGEL FRWNVSDLG-GLGCGLKNRSSEGPSSPSGKLMSPKLY-VWAKDRPEIWEGEPPCLPPRDSLN QSLSQDLT- MAPGSTLWLSCGVPPDSVSRGPLSWTHVEIPK-GPKSLLSLELKDDRPARDMW VMETGLLL-PRATAQDAGKYYCHRGNLTMSFHLEIT-ARPVLWHVVLLRTGGWKVSAVTLA YLIFCLCSLVGILHLQRALVLRRKRKRMTDP-TRRF), preferably it comprises or consists of SEQ ID NO:1.

3. The CAR molecule according to item 1 or 2 wherein the the antigen binding domain comprises comprises a sequence having at least 80% of identity to the 7G3 VL sequence: DFVMTQSPSSLTVTAGEKVTMSCK-SSQSLLNSGNQKNYLTWYLQKPGQPPKLLIY-WASTR ESGVPDRFTGSGSGTDFTLTISSVQAED-LAVYYCQNDYSYPYTFGGGTKLEIKR (SEQ ID NO:4) and/or a sequence having at least 80% of identity to the 7G3: EVQLQQSGPELVKPGASVKMSCK-ASGYTFTDYYMKWVKQSHGKSLEWIGDIIPSN-GATFY NQKFKGKATLTVDRSSSTAYMHLNSLTSED-SAVYYCTRSEILLRASWFAYVVGQGTLVTV (SEQ ID NO:5), said VH and/or VL being optionally humanized, wherein said VH and VL are preferably separated by a first linker, more preferably said scFv comprises a VL comprising SEQ ID NO: 4 and a VH comprising SEQ ID NO: 5.

4. The CAR molecule according to any one of previous items wherein the spacer comprises the extacellular region of the CD8 alpha chain, preferably it comprises or consists of a sequence having at least 80% of identity to aa. 12-42 of SEQ ID NO: 7 (IASQPLSLRPEACR-PAAGGAVHTRGLDFACD) and/or the spacer comprises or consists of a sequence having at least 80% of identity to aa. 1-11 of SEQ ID NO:7 (PAPRPPTPAPT), more preferably the spacer comprisises SEQ ID NO:7.

5. The CAR molecule according to any one of previous items wherein the trans membrane domain comprises a trasmembrane domain of a protein selected from the group consisting of CD8, alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD15, preferably it comprises the trans membrane domain of a CD8, more preferably it comprises or consists of a sequence having at least 80% of identity to SEQ ID NO: 8 (IYI-WAPLAGTCGVLLLSLVIT), even more preferably it comprises SEQ ID NO: 8.

6. The CAR molecule according to any one of previous items, wherein said cytoplasmatic domain comprises a region of CD8a cytoplasmatic portion, a 4-1BB co-stimulatory domain and a CD3-zeta chain, preferably said cytoplasmatic domain comprises a linker between the CD8a cytoplasmic and the 4-1BB co-stimulatory domain, more preferably:
   the CD8a cytomplasmic comprises or consists of a sequence having at least 80% of identity to SEQ ID NO:9 (LYCNHRNRRRVCKCPR), even more preferably it comprises SEQ ID NO:9, and/or
   the co-stimulatory signalling domain CD137 (4-1BB) comprises or consists of a sequence having at least 80% of identity to SEQ ID NO:10 (KRGRKKLLY-IFKQPFMRPVQTTQEEDGCSCRFPEEEGG-CEL), even more preferably it comprises SEQ ID NO:10, and/or
   the CD3-Zeta chain comprises or consists of a sequence having at least 80% of identity to SEQ ID NO: 11 (RVKFSRSADAPAYQQGQNQLYNELNLGR- REEYDVLDKRRGRDPEMGGKPRRKNPQEGL
YNELQKDKMAEAYSEI-
GMKGERRRGKGEIDGLYQGLSTATKDTY-
DALHMQALPPR*), even more preferably it com-
prises SEQ ID NO:11, and/or the sequence encoding the linker between the CD8a
cytomplasmic and the co-stimulatory signalling
domain CD137 (4-1BB) consists of 6 nucleotides.

7. The CAR molecule according to any one of previous
items further comprising:
i. between the extracellular domain and transmembrane
domain of human CD19 and the antigen binding
domain:
a clevable linker, preferably a 2A peptide or an IRES,
and/or
a signal peptide and/or
a linker, and/or
ii. between the antigen binding domain and the spacer
domain.
a linker and/or
a trackable marker, preferably:
the 2 A peptide comprises or consists of a sequence
having at least 80% of identity to SEQ ID NO:2
(RGRGRGSLLTCGDVEENPGP), more preferably
it comprises SEQ ID NO:2, and/or
the signal peptide comprises or consist of a sequence
having at least 80% of identity to SEQ ID NO:51
(MEFGLSWLFLVAILKGVQC), more preferably it
comprises SEQ ID NO:3, and/or
the trackable marker comprises or consist of a sequence
having at least 80% of identity to SEQ ID NO:6
(ELPTQGTFSNVSTNVS), more preferably it com-
prises SEQ ID NO:6.

8. The CAR molecule according to any one of previous
items wherein the sequence encoding for at least one
of: the extracellular domain and transmembrane
domain of human CD19, the trackable marker, the
spacer domain, the transmembrane domain and the
co-stimulatory domain is codon optimized.

9. The CAR molecule according to any one of previous
items wherein said molecule comprises: from the N-ter-
minus to the C-terminus:
a) an extracellular domain and transmembrane domain
of human CD19, as defined in any one of item 1-2
and 8,
b) a clevable linker, as defined in item 7,
c) a signal peptide, as defined in item 7,
d) an antigen binding domain, as defined in any one of
items 1 and 3
e) a trackable marker, as defined in items 7-8.
f) a spacer domain, as defined in any one of items 1 and
4 and 8
g) a transmembrane domain, as defined in any one of
items 1 and 5 and 8
h) a cytoplasmatic domain, as defined in any one of
items 1 and 6 and 8, preferably the CAR molecule
comprises or consists of a sequence having at least
80% of identity to SEQ ID NO:12, more preferably
it comprises a sequence of SEQ ID NO:12.

10. An isolated nucleic acid molecule encoding the chi-
meric antigen receptor molecule according to any one
of the previous items, wherein said isolated nuelcic
acid molecule is preferably operatively linked to
expression control sequences, more preferably said
molecule comprises at least one sequence having at
least 80% of identity to one the following sequence:
SEQ ID NO:13, SEQ ID NO:14, SEQ ID NO:15, SEQ ID NO:16, SEQ ID NO:17, SEQ ID NO:18, SEQ ID
NO:19, SEQ ID NO:20, SEQ ID NO:21, SEQ ID
NO:22, SEQ ID NO:23, SEQ ID NO:24, SEQ ID
NO:25, SEQ ID NO:26, even more preferably said
molecule comprises or consists of a sequence having at
least 80% of identity to SEQ ID NO: 29.

11. A vector comprising the isolated nucleic acid molecule
according to item 10, preferably an expression vector,
more preferably the vector comprises an exogenous
promoter controlling the expression of the CAR, pref-
erably said vector is a DNA, an RNA vector, a plasmid,
a lentivirus vector, adenoviral vector, retrovirus vector
or non-viral vector.

12. An engineered immune cell, preferably a T cell, more
preferably an alfa/beta and gamma/delta T cell, or NK
cells or NK-T cells or combinations thereof, even more
preferably of human origin, comprising the vector
according to item 11 or the isolated nucleic acid mol-
ecule according to item 10 or expressing at the cell
surface a CAR according to any one of items 1-9.

13. A pharmaceutical composition comprising the the
isolated nucleic acid molecule according to item 10 or
the vector according to item 11 or the cell according to
item 12 with at least one pharmaceutically acceptable
excipiente and/or adjuvant.

14. The CAR molecule according to any one of items 1-9,
the isolated nucleic acid molecule according to item 10,
the vector according to item 11, the cell according to
item 12 or the pharmaceutical composition of item 13
for medical use, preferably for use in the treatment of
CD123+ cancers, more preferably of acute myeloid or
B-lymphoid leukemias, blastic plasmacytoid dendritic
neoplasms (BPDCN), myelodispastic syndrome or
hairy cell leukemia or for use before, after or during a
haematopoietic stem cell transplantion.

15. The extracellular domain and transmembrane domain
of human CD19 as defined in any one of items 1-2 and
8, for use as inducer of death in a cell genetically
modified with said extracellular domain and transmem-
brane domain of human CD19, after the exposure of
said cell to anti-CD19 antibody, including bite antibod-
ies, e.g. Blinatumomab.

REFERENCES

1. Shi, M., et al., CD123 a novel biomaker for diagnosis and
treatment of leukemia. Cardiovasc Hematol Disord Drug
Targets, 2019.
2. Sapienza, M. R., et al., Blastic Plasmacytoid Dendritic
Cell Neoplasm: State of the Art and Prospects. Cancers
(Basel), 2019. 11(5).
3. Stevens, B. M., et al., CD123 CAR T cells for the
treatment of myelodysplastic syndrome. Exp Hematol,
2019. 74: p. 52-63 e3.
4. Salem, D. A., et al., Differential Expression of CD43,
CD81, and CD200 in Classic Versus Variant Hairy Cell
Leukemia. Cytometry B Clin Cytom, 2019.
5. Forman, S. J. and J. M. Rowe, The myth of the second
remission of acute leukemia in the adult. Blood, 2013.
121(7): p. 1077-82.
6. Majeti, R., Monoclonal antibody therapy directed against
human acute myeloid leukemia stem cells. Oncogene,
2011. 30(9): p. 1009-19.
7. Korpelainen, E. I., et al., Interferon-gamma upregulates
interleukin-3 (IL-3)receptor expression in human
endothelial cells and synergizes with IL-3 in stimulating

*major histocompatibility complex class II expression and cytokine production.* Blood, 1995. 86(1): p. 176-82.

8. Li, K., et al., *Expression of complement components, receptors and regulators by human dendritic cells.* Mol Immunol, 2011. 48(9-10): p. 1121-7.

9. Taussig, D. C., et al., *Hematopoietic stem cells express multiple myeloid markers: implications for the origin and targeted therapy of acute myeloid leukemia.* Blood, 2005. 106(13): p. 4086-92.

10. Munoz, L., et al., *Interleukin-3 receptor alpha chain (CD123) widely expressed in hematologic malignancies.* Haematologica, 2001. 86(12): p. 1261-9.

11. Testa, U., et al., *Elevated expression of IL-3Ralpha in acute myelogenous leukemia is associated with enhanced blast proliferation, increased cellularity, and poor prognosis.* Blood, 2002. 100(8): p. 2980-8.

12. Graf, M., et al., *Expression and prognostic value of hemopoietic cytokine receptors in acute myeloid leukemia (AML): implications for future therapeutical strategies.* Eur J Haematol, 2004. 72(2): p. 89-106.

13. Vergez, F., et al., *High levels of CD34+CD38low/-CD123+ blasts are predictive of an adverse outcome in acute myeloid leukemia: a Groupe Ouest-Est des Leucemies Aigues et Maladies du Sang (GOELAMS) study.* Haematologica, 2011. 96(12): p. 1792-8.

14. Tettamanti, S., et al., *Targeting of acute myeloid leukaemia by cytokine-induced killer cells redirected with a novel CD123-specific chimeric antigen receptor.* Br J Haematol, 2013. 161(3): p. 389-401.

15. Smith, B. D., et al., *First-in Man, Phase 1 Study of CSL362 (Anti-IL3Rα/Anti-CD123 Monoclonal Antibody) in Patients with CD123+ Acute Myeloid Leukemia (AML) in CR at High Risk for Early Relapse.* Blood, 2014. 124(21): p. 120-120.

16. Testa, U., E. Pelosi, and A. Frankel, *CD 123 is a membrane biomarker and a therapeutic target in hematologic malignancies.* Biomark Res, 2014. 2(1): p. 4.

17. Mardiros, A., et al., *T cells expressing CD123-specific chimeric antigen receptors exhibit specific cytolytic effector functions and antitumor effects against human acute myeloid leukemia.* Blood, 2013. 122(18): p. 3138-48.

18. Gill, S., et al., *Preclinical targeting of human acute myeloid leukemia and myeloablation using chimeric antigen receptor-modified T cells.* Blood, 2014. 123(15): p. 2343-54.

19. Thokala, R., et al., *Redirecting Specificity of T cells Using the Sleeping Beauty System to Express Chimeric Antigen Receptors by Mix-and-Matching of VL and VH Domains Targeting CD123+ Tumors.* PLoS One, 2016. 11(8): p. e0159477.

20. Schroeder, H. W., Jr. and L. Cavacini, *Structure and function of immunoglobulins.* J Allergy Clin Immunol, 2010. 125(2 Suppl 2): p. S41-52.

21. Huston, J. S., et al., *Protein engineering of antibody binding sites: recovery of specific activity in an anti-digoxin single-chain Fv analogue produced in Escherichia coli.* Proc Natl Acad Sci U S A, 1988. 85(16): p. 5879-83.

22. Bird, R. E., et al., *Single-chain antigen-binding proteins.* Science, 1988. 242(4877): p. 423-6.

23. Milone, M. C., et al., *Chimeric receptors containing CD137 signal transduction domains mediate enhanced survival of T cells and increased antileukemic efficacy in vivo.* Mol Ther, 2009. 17(8): p. 1453-64.

24. Batzer, M. A., J. E. Carlton, and P. L. Deininger, *Enhanced evolutionary PCR using oligonucleotides with inosine at the 3'-terminus.* Nucleic Acids Res, 1991. 19(18): p. 5081.

25. Ohtsuka, E., et al., *An alternative approach to deoxyoligonucleotides as hybridization probes by insertion of deoxyinosine at ambiguous codon positions.* J Biol Chem, 1985. 260(5): p. 2605-8.

26. Rossolini, G. M., et al., *Use of deoxyinosine-containing primers vs degenerate primers for polymerase chain reaction based on ambiguous sequence information.* Mol Cell Probes, 1994. 8(2): p. 91-8.

27. Pule, M. A., et al., *A chimeric T cell antigen receptor that augments cytokine release and supports clonal expansion of primary human T cells.* Mol Ther, 2005. 12(5): p. 933-41.

28. Perna, S. K., et al., *Interleukin-7 mediates selective expansion of tumor-redirected cytotoxic T lymphocytes (CTLs) without enhancement of regulatory T-cell inhibition.* Clin Cancer Res, 2014. 20(1): p. 131-9.

29. Perna, S. K., et al., *Interleukin 15 provides relief to CTLs from regulatory T cell-mediated inhibition: implications for adoptive T cell-based therapies for lymphoma.* Clin Cancer Res, 2013. 19(1): p. 106-17.

30. Cieri, N., et al., *IL-7 and IL-15 instruct the generation of human memory stem T cells from naive precursors.* Blood, 2013. 121(4): p. 573-84.

31. Zheng, Z., N. Chinnasamy, and R. A. Morgan, *Protein L: a novel reagent for the detection of chimeric antigen receptor (CAR) expression by flow cytometry.* J Transl Med, 2012. 10: p. 29.

32. Klement, M., et al., *Effect of linker flexibility and length on the functionality of a cytotoxic engineered antibody fragment.* J Biotechnol, 2015. 199: p. 90-7.

The invention claimed is:

1. A chimeric antigen receptor (CAR) molecule comprising, the sequence of SEQ ID NO: 12.

2. The CAR molecule according to claim 1, that consists of the sequence of SEQ ID NO: 12.

3. An isolated nucleic acid molecule encoding the chimeric antigen receptor molecule according to claim 1, wherein said isolated nucleic acid molecule is operatively linked to expression control sequences.

4. A vector comprising the isolated nucleic acid molecule according to claim 3.

5. An isolated engineered immune cell, comprising the vector according to claim 4.

6. A composition comprising the isolated nucleic acid molecule according to claim 3, and a pharmaceutically acceptable excipient and/or adjuvant.

7. A composition comprising a transduced cell comprising the CAR molecule of claim 1.

*     *     *     *     *